US012753177B2

(12) United States Patent
Nielsen et al.

(10) Patent No.: US 12,753,177 B2
(45) Date of Patent: Oct. 6, 2026

(54) SUBSTITUTED 1,2,3-TRIAZOLES AS ANTIBACTERIAL AND ANTIFUNGAL PLEUROMUTILIN CONJUGATES

(71) Applicant: SYDDANSK UNIVERSITET, Odense M (DK)

(72) Inventors: Poul Nielsen, Odense SV (DK); Christoffer Vogsen Heidtmann, Odense M (DK)

(73) Assignee: SYDDANSK UNIVERSITTET (DK)

( * ) Notice: Subject to any disclaimer, the term of this patent is extended or adjusted under 35 U.S.C. 154(b) by 910 days.

(21) Appl. No.: 17/997,642

(22) PCT Filed: Apr. 29, 2021

(86) PCT No.: PCT/EP2021/061318
§ 371 (c)(1),
(2) Date: Oct. 31, 2022

(87) PCT Pub. No.: WO2021/219813
PCT Pub. Date: Nov. 4, 2021

(65) Prior Publication Data

US 2023/0219964 A1 Jul. 13, 2023

(30) Foreign Application Priority Data

May 1, 2020 (EP) .................................... 20172580

(51) Int. Cl.

| | |
|---|---|
| ***A61K 31/4192*** | (2006.01) |
| ***A61P 31/04*** | (2006.01) |
| ***C07D 249/04*** | (2006.01) |
| ***C07D 403/10*** | (2006.01) |
| ***C07D 487/04*** | (2006.01) |

(52) U.S. Cl.
CPC ............ *C07D 487/04* (2013.01); *A61P 31/04* (2018.01); *C07D 249/04* (2013.01); *C07D 403/10* (2013.01)

(58) Field of Classification Search
CPC .......................... A61K 31/4192; C07D 487/04
USPC ........................................... 514/241; 548/255
See application file for complete search history.

(56) References Cited

FOREIGN PATENT DOCUMENTS

| | | |
|---|---|---|
| CN | 110818648 A | 2/2020 |
| WO | 2000/37074 A1 | 12/1999 |
| WO | 2000/73287 A1 | 12/2000 |

OTHER PUBLICATIONS

Dreier, I. et al., A click chemistry approach to pleuromutilin derivatives. Part 3: Extended footprinting analysis and excellent MRSA inhibition for a derivative with an adenine phenyl side chain, Bioorg. Med. Chem. Lett., 24: 1043-1046, 2014.
Lolk, L. et al., A Click Chemistry Approach to Pleuromutilin Conjugates with Nucleosides or Acyclic Nucleoside Derivatives and Their Binding to the Bacterial Ribosome, J. Med. Chem., 51: 4957-4967, 2008.
Dreier, I et al., A Click Chemistry Approach to Pleuromutilin Derivatives, Part 2: Conjugates with Acyclic Nucleosides and Their Ribosomal Binding and Antibacterial Activity, J. Med. Chem., 55: 2067-2077, 2012.
International Search Report/Written Opinion for PCT/EP2021/061318, May 25, 2021.
International Preliminary Report on Patentability for PCT/EP2021/061318, Nov. 10, 2022.

*Primary Examiner* — Douglas M Willis
(74) *Attorney, Agent, or Firm* — Dinsmore & Shohl LLP

(57) ABSTRACT

Compounds of formula (1) comprising a pleuromutilin backbone with a triazole based side-group at C22 are provided. The compounds can be used for treatment of bacterial infections and fungal infections. Importantly, infections caused by multidrug-resistant bacteria, such as methicillin-resistant *Staphylococcus aureus* (MRSA) may be treated effectively.

(1)

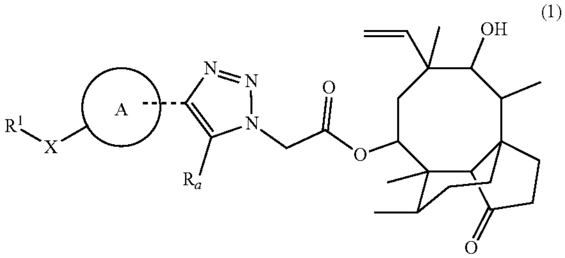

29 Claims, 3 Drawing Sheets

SUBSTITUTED 1,2,3-TRIAZOLES AS ANTIBACTERIAL AND ANTIFUNGAL PLEUROMUTILIN CONJUGATES

CROSS-REFERENCE TO RELATED APPLICATION

This application claims priority to co-pending PCT Application No. PCT/EP2021/061318 filed Apr. 29, 2021, which claims priority to EP Application No. 20172580.1 filed on May 1, 2020, both of which are hereby incorporated by reference in their entirety.

TECHNICAL FIELD OF THE INVENTION

The present invention relates to the provision of pleuromutilin conjugates, which mediate antibacterial and antifungal effects. In particular, the present invention relates to the treatment of infections caused by multidrug-resistant bacteria, such as methicillin-resistant *Staphylococcus aureus* (MRSA), *Streptococcus pneumonia, Enterococcus faecalis* and vancomycin-resistant enterococci (VRE).

BACKGROUND OF THE INVENTION

Antibiotic resistance is an eminent threat to global health. The evolutionary ability of bacteria to develop resistance towards small-molecules is a world-wide problem. Thus, development of new antibiotics with low inherent rates of resistance and cross-resistance is needed. As such, the antibiotic class of pleuromutilins has proven to possess these resilient properties. The diterpene natural product (+)-pleuromutilin, which the class is based upon, was first isolated in 1951 from the fungi *Pleurotus mutilus* and *Pleurotis passeckerianus*. Since then, many synthetic pleuromutilin conjugates have been synthesised which are potent against pathogens of the *Staphylococci, Mycoplasmas* and *Streptococci* species. Especially important is the methicillin-resistant *Staphylococcus aureus* (MRSA). A bacteria which is responsible for skin and soft tissue infections (SSTIs), as well as more severe infections like bacteraemia (blood), endocarditis (heart), osteomyelitis (bone), necrotizing fasciitis (flesh eating) and necrotizing pneumonia (lung) infections.

Synthetic pleuromutilin conjugates have been synthesized by derivatisation at the C14 side chain or at the tricyclic mutilin core of (+)-pleuromutilin. However, so far only four C22 sulfanylacetyl conjugates have reached the market as antibacterial drugs. These are the two veterinary drugs Tiamulin and Valnemulin, and the clinical agents Lefamulin and Retapamulin.

A particularly interesting pathway to obtain pleuromutilin conjugates is to exchange the C22 hydroxy of (+)-pleuromutilin with an azido group. This allows for effective click-chemistry, wherein the azido group reacts with an alkyne species to form a pleuromutilin conjugate with a substituted triazole at the C22 carbon. The prior art discloses several pleuromutilin conjugates, which are synthesized by Cu(I)-catalysed alkyne-azide [3+2] cycloaddition (CuAAC).

As such, Ida Dreier et al., *Bioorg. Med. Chem. Lett.*, 2014, 24, 1043-1046, and Ida Dreier et al., *J. Med. Chem.*, 2012, 55, 2067-2077, disclose pleuromutilin compounds comprising a pleuromutilin backbone and a triazole part further connected to an aromatic ring substituted with a bicyclic ring system. However, the aromatic and bicyclic rings are directly bonded to one another, which may delimit the antibiotic effects of the compounds.

Line Lolk et al., *J. Med. Chem.*, 2008, 51, 4957-4967, discloses compounds having a pleuromutilin backbone which is substituted at C22 with a triazole. The triazole moiety being directly connected to a mono- or bicyclic ring system by a chain of $CH_2$ groups. Thus, the compounds do not comprise an aromatic ring between the triazole moiety and said ring system, which may lower their physicochemical properties.

WO00/37074, discloses pleuromutilin conjugates possibly substituted at C22 with a triazole moiety further attached to a terminating aromatic ring either directly or through a linker unit. However, the document does not provide sufficient details on the synthesis procedures to obtain these conjugates.

Thus, although several examples and synthetic routes for provision of pleuromutilin conjugates are disclosed in the prior art, further development of such compounds is required to keep up with the evolutionary bacteria, especially in regard of development of chemical resistances.

Hence, an improved pleuromutilin compound for treatment of infections would be advantageous, and in particular a more efficient and/or reliable pleuromutilin compound for treatment of methicillin-resistant bacteria would be advantageous.

SUMMARY OF THE INVENTION

Compounds comprising of a pleuromutilin backbone with a triazole based side-group at C22 are provided herein. The side-group comprises a triazole moiety attached by a single bond to an aromatic ring (A) which is further connected to a terminal substituent group ($R^1$) by linker (X). In the following, the compounds may also be regarded as pleuromutilin conjugates and derivatives of pleuromutilin.

Thus, one aspect of the present invention relates to a compound according to Formula (1)

(1)

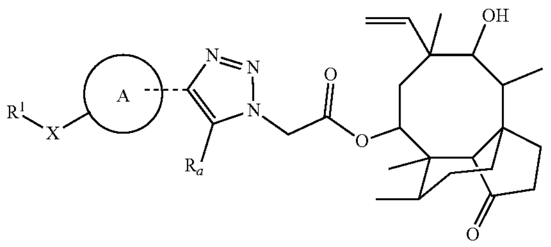

wherein, A is an optionally substituted aromatic ring;

the dotted line (-----) denotes a single bond connected to any position of said aromatic ring by substitution of one of the hydrogen atoms of the aromatic ring;

$R_a$ is selected from the group consisting of hydrogen, hydroxy, hydroxy($C_1$-$C_5$)alkyl, amino, amino($C_1$-$C_5$)alkyl, ($C_1$-$C_5$)alkyl, methoxy, and ethoxy, preferably hydrogen, X is selected from the group consisting of —O—, —NH—, —S—, optionally substituted ($C_2$-$C_5$)alkenediyl, optionally substituted ($C_2$-$C_5$)alkynediyl, and optionally substituted ($C_1$-$C_5$)alkanediyl, $R^1$ is a radical of an optionally substituted mono- or bicyclic ring system, or $R^1$ is an optionally substituted acyclic system comprising a number of q carbon atoms and q is selected from the group consisting of 0, 1, 2, 3, 4, 5, 6, 7, 8, 9, and 10; or $R^1$—X is cyano.

The disclosed compounds have been found to mediate strong antibiotic and antifungal effects. Thus, an object of the present invention relates to the provision of compounds suitable for treatment of bacterial infections and/or fungal infections.

In particular, it is an object of the present invention to provide antibiotics and antifungal drugs that solve the above mentioned problems of the prior art with treating infections of species that are resistant to commonly known drugs. Important targets are the methicillin-resistant *Staphylococcus aureus* (MRSA), *Streptococcus pneumonia, Enterococcus faecalis* and vancomycin-resistant enterococci (VRE) towards which the compounds are effective.

Thus, another aspect of the present invention relates to a pharmaceutical composition comprising a compound as described herein or a pharmaceutically acceptable salt thereof.

Yet another aspect of the present invention is to provide a compound as described herein or a pharmaceutical composition as described herein for use as a medicament.

Still another aspect of the present invention is to provide a compound as described herein or a pharmaceutical composition as described herein for use in the treatment or prevention of a bacterial infection and/or a fungal infection.

An additional aspect of the present invention is to provide a kit comprising:

i) a compound as described herein or a pharmaceutical composition as described herein,
ii) one or more additional therapeutic agents, and
iii) optionally, instructions for use.

Figure 1:
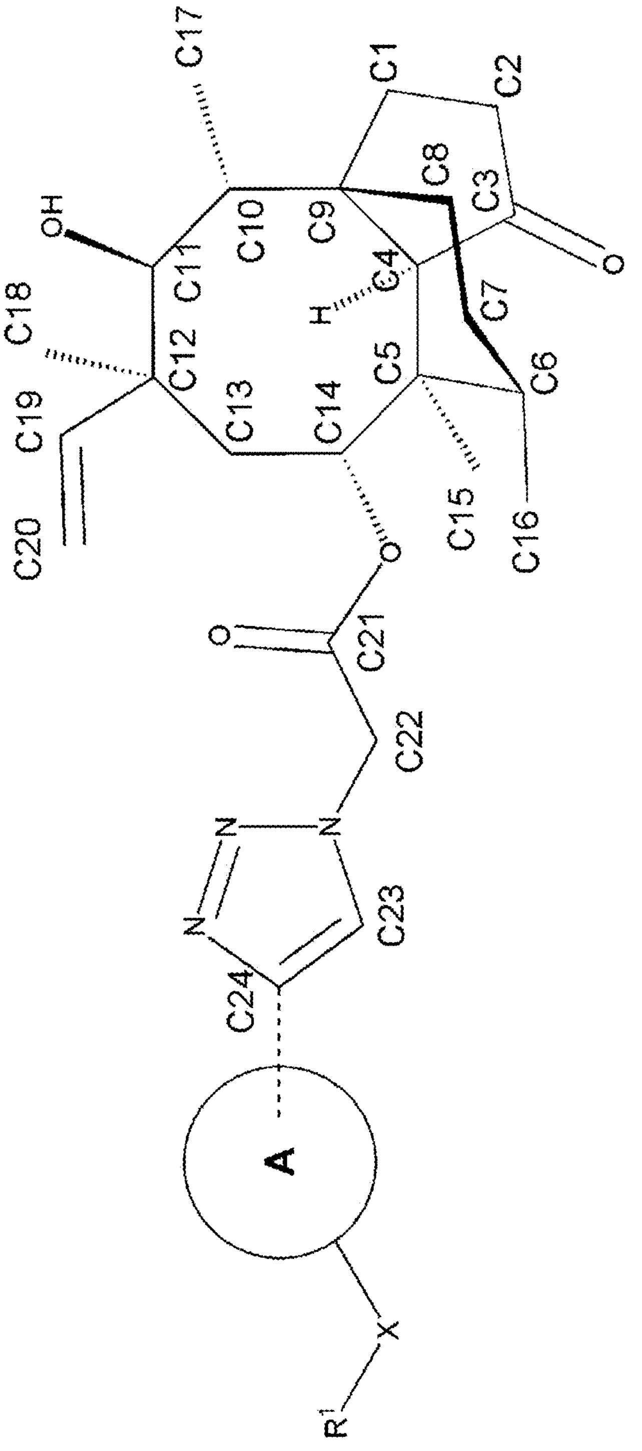
FIG. 1 shows, a schematic overview of the pleuromutilin conjugates with the carbon numbering for the pleuromutilin backbone and triazole moiety.
Figure 2:
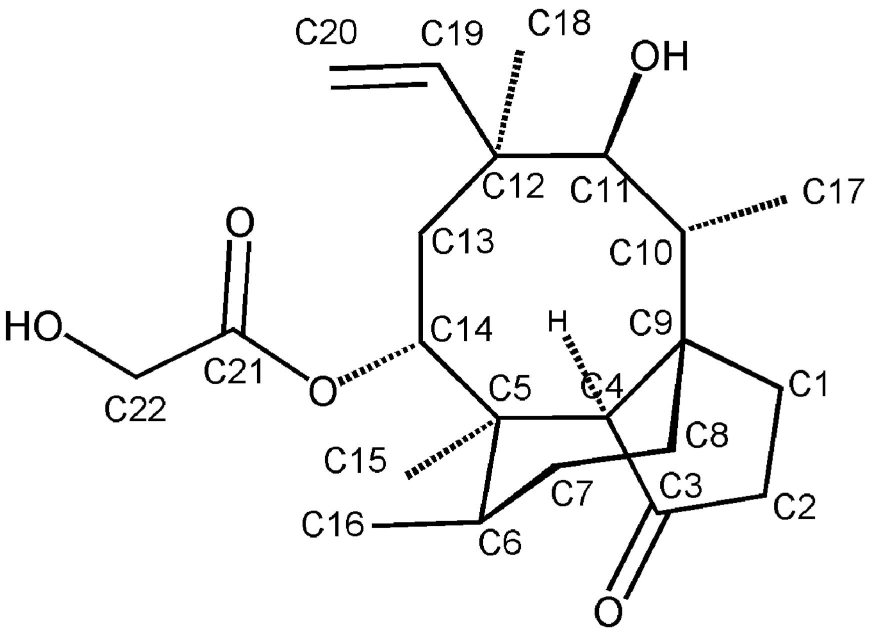
FIG. 2 shows, natural (+)-pleuromutilin with the carbon numbering for the pleuromutilin backbone.

The present invention will now be described in more detail in the following.

DETAILED DESCRIPTION OF THE INVENTION

Definitions

Prior to discussing the present invention in further details, the following terms and conventions will first be defined:

Acyclic System

In the present context, the term "acyclic system" refers to a structure wherein the atoms do not form a ring. Thus, exemplary acyclic systems include, but are not limited to linear and branched aliphatic structures optionally comprising heteroatoms, and functional groups such as hydroxy, amine, and thiol.

Adjuvant

In the present context, the term "adjuvant" refers to a compound or mixture that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response.

Alkanediyl

In the present context, the term "alkanediyl" refers to the diradical of an alkane. Without being restricted to theory, such a diradical may also be referred to as an "alkylene".

Alkenediyl

In the present context, the term "alkenediyl" refers to the diradical of an alkene. Without being restricted to theory, such a diradical may also be referred to as an "alkenylene".

Alkynediyl

In the present context, the term "alkynediyl" refers to the diradical of an alkyne. Without being restricted to theory, such a diradical may also be referred to as an "alkynylene".

Aromatic Ring

In the present context, the term "aromatic ring" refers to a carbocyclic or heterocyclic ring-shaped structure wherein the atoms forming the ring are connected by a conjugated system. The number of atoms forming the ring may be, but is not limited to, 5 (i.e. 5-membered rings) or 6 (i.e. 6-membered rings).

Bacterial Infection

In the present context, the term "bacterial infection" refers to an infection caused by any type of bacteria.

Antibacterial Activity

In the present context, the term "antibacterial activity" refers to a compound or agent that prevent bacterial growth and/or reproduction, however not necessarily killing the bacteria. The antibacterial activity mediated by a chemical compound may be determined, for example, by measuring the minimal inhibitory concentration (MIC) at which the compound inhibits visible growth of the bacteria.

Carrier

In the present context, the term "carrier" refers to any solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Diluent

In the present context, the term "diluent" refers to a substance that serves as a vehicle or medium for a drug or other active substance.

Diradical

In the present context, a diradical is a chemical moiety obtained by removing a first H and a second H from the chemical structure of a compound whereby two covalent bonds are broken. Two out of the four electrons that originally formed the bonds are removed together with the first and second H, whereas the other two electrons stays with the newly formed diradical. The diradical may subsequently form two new covalent bonds at the locations within the chemical structure, where the first H and second H were removed, thus connecting the diradical with two other chemical groups, molecules, moieties, units, compounds, radicals, diradicals, species, substances, or similar.

Excipient

In the present context, the term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Fungal Infection

In the present context, the term "fungal infection" refers to an infection caused by any type of fungi.

Gram-Negative Bacteria

In the present context, the term "gram-negative bacteria" refers to prokaryotic cells, whose cell wall comprises relatively little peptidoglycans and give a gram-negative result when contacted with gram stain.

Gram-Positive Bacteria

In the present context, the term "gram-positive bacteria" refers to prokaryotic cells, whose cell wall comprises mainly peptidoglycans and give a gram-positive result when contacted with gram stain.

Methicillin-Resistant *Staphylococcus aureus* (MRSA)

In the present context, the term "methicillin-resistant" refers to bacteria that are resistant to treatment with Methicillin and possibly also resistant to treatment with other antibiotics such as Oxacillin.

Multidrug-Resistant

In the present context, the term "multidrug-resistant" refers to bacteria that are resistant to treatment with at least one antimicrobial drug, such as methicillin, Oxacillin, and Vancomycin.

Mono- or Bicyclic Ring System

In the present context, the term "mono- or bicyclic ring system" refers to monocyclic ring systems and bicyclic ring systems. A monocyclic ring system may be an aromatic, saturated, or unsaturated carbocyclic or heterocyclic structure comprising one ring of atoms, such as in furan or uracil. A bicyclic ring system may be an aromatic, saturated, or unsaturated carbocyclic or heterocyclic structure comprising two fused rings of atoms, such as in purine or guanine, or the rings may be separate, such as in biphenyl.

Optionally Substituted

In the present context, the term "optionally substituted" refers to a chemical structure wherein one or more of the hydrogen atoms may, optionally, be exchanged with substituents (e.g. hydroxy, oxo, etc.). The possible substituents may be any one chemical group or moiety useful for investigating the effects of substitutions patterns.

Pharmaceutical Composition

In the present context, the term "pharmaceutical composition" refers to a composition suspended in a suitable amount of a pharmaceutical acceptable diluent or excipient.

Pharmaceutically Acceptable Salt

In the present context, the term "pharmaceutically acceptable salt" refers to a salt that can be formulated into a composition for pharmaceutical use including, e.g., metal salts (sodium, potassium, magnesium, calcium, etc.) and salts of ammonium or organic amines.

Single Bond

In the present context, the term "single bond" refers to a σ-bond connecting two atoms.

Subject in Need Thereof

In the present context, the term "subject in need thereof" refers to a human or non-human species including primates, livestock animals e.g. sheep, cows, pigs, horses, donkey, goats, laboratory test animals e.g. mice, rats, rabbits, guinea pigs, hamsters, companion animals e.g. dogs, cats, avian species e.g. poultry birds, aviary birds, reptiles and amphibians.

Therapeutic Agents

In the present context, a "therapeutic agent" refers to a compound capable of causing a therapeutic effect in the body. Examples of therapeutic agents include, but are not limited to, proteins, peptides, small molecule drugs, anticancer agents and pharmaceutically acceptable salts thereof.

Radical

In the present context, a radical is a chemical moiety obtained by removing a H from the chemical structure of a compound whereby a covalent bond is broken and a first electron and a second electron (the electrons originally forming the bond) are divided such that the first electron is removed together with the H, whereas the second electron stays with the newly formed radical. The radical may subsequently form a new covalent bond at the location within the chemical structure where the H was removed, thus connecting the radical with another chemical group, molecule, moiety, unit, compound, radical, diradical, species, substance, or similar.

Vancomycin-Resistant

In the present context, the term "vancomycin-resistant" refers to bacteria that are resistant to treatment with Vancomycin and possibly also resistant to treatment with other antibiotics.

$(C_x-C_y)$

In the present context, the nomenclature "$(C_x-C_y)$", wherein x and y are integers, refers to any chemical structure or substructure which comprises a number of carbon atoms in the range of x to y in the part following the nomenclature. For example, the nomenclature "$(C_1-C_4)$" (i.e. x=1 and y=4) refers to all chemical structures or substructures comprising a number of carbon atoms selected from the group consisting of 1, 2, 3, and 4. As a further example, "$(C_1-C_4)$ alkylamino" refers to radicals such as, but not limited to, methylamino, ethylamino, propylamino, butylamino, and 2-methyl-propylamino.

The provided compounds comprise an active pleuromutilin backbone similar to that of naturally occurring (+)-pleuromutilin. Thus, the compounds are able to delimit the proliferation of bacteria, yet also to inhibit fungal infections. The effect of substituting the hydroxy group at C22 of natural (+)-pleuromutilin with different triazole based side-groups revealed that compounds may be designed such that their antibiotic and antifungal properties are similar or increased in comparison to commercial drugs and drug candidates. Furthermore, the compounds possess good physicochemical properties and are thus relevant for medications.

Thus, one aspect of the present invention relates a compound according to Formula (1)

(1)

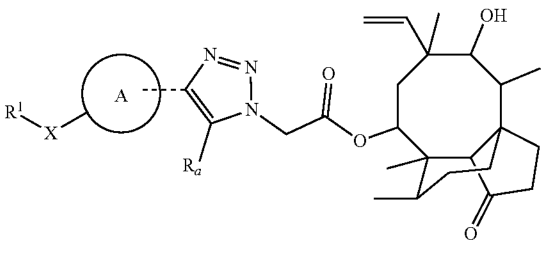

wherein, A is an optionally substituted aromatic ring;

the dotted line (-----) denotes a single bond connected to any position of said aromatic ring by substitution of one of the hydrogen atoms of the aromatic ring;

$R_a$ is selected from the group consisting of hydrogen, hydroxy, hydroxy($C_1$-$C_5$)alkyl, amino, amino($C_1$-$C_5$)alkyl, ($C_1$-$C_5$)alkyl, methoxy, and ethoxy, preferably hydrogen, X is selected from the group consisting of —O—, —NH—, —S—, optionally substituted ($C_2$-$C_5$)alkenediyl, optionally substituted ($C_2$-$C_5$)alkynediyl, and optionally substituted ($C_1$-$C_5$)alkanediyl, $R^1$ is a radical of an optionally substituted mono- or bicyclic ring system, or $R^1$ is an optionally substituted acyclic system comprising a number of q carbon atoms and q is selected from the group consisting of 0, 1, 2, 3, 4, 5, 6, 7, 8, 9, and 10; or $R^1$—X is cyano.

A moiety falling within the scope of "($C_2$-$C_5$)alkenediyl" is a diradical of an aliphatic compound comprising at least one double bond. Examples include, but are not limited to —CH═CH—, —$CH_2$CH═CH—, and —$CH_2C(CH_3)$═CH—.

A moiety falling within the scope of "($C_2$-$C_5$)alkynediyl" is a diradical of an aliphatic compound comprising at least one triple bond. Examples include, but are not limited to —C≡H—, —$CH_2$C≡C—, and —$CH_2CH(CH_3)$C≡C—.

A moiety falling within the scope of "($C_1$-$C_5$)alkanediyl" is a diradical of an aliphatic compound comprising no double bonds or triple bonds. Examples include, but are not limited to —$CH_2$—, —$CH_2CH_2$—, and —$CH_2CH(CH_3)CH_2$—.

An embodiment of the present invention relates to the compound as described herein, wherein the acyclic system is selected from the group consisting of fluoro, chloro, bromo, iodo, ($C_1$-$C_6$)alkyl, ($C_2$-$C_6$)alkenyl, ($C_2$-$C_6$)alkynyl, hydroxyl, sulfanyl, formyl, amino, imino, cyano, nitro, carboxy, carbamoyl, thiocarboxy, sulfo, sulfino, phosphono, ($C_1$-$C_6$)alkyloxycarbonyl, ($C_2$-$C_6$)alkenyloxycarbonyl, ($C_2$-$C_6$)alkynyloxycarbonyl, ($C_1$-$C_6$)alkylamino, di($C_1$-$C_6$)alkylamino, hydrazinocarbonyl, ($C_1$-$C_6$)alkoxy, ($C_1$-$C_3$)alkylpiperazino, amino($C_1$-$C_6$)alkylamino, guanidino, cyclo($C_3$-$C_8$)alkyl, aryl, benzoyl, hydroxybenzoyl, aminobenzoyl, methoxybenzoyl, picolinoyl, hydroxypicolinoyl, aminopicolinoyl, methoxypicolinoyl, nicotinoyl, hydroxynicotinoyl, aminonicotinoyl, methoxynicotinoyl, isonicotinoyl, hydroxyisonicotinoyl, aminoisonicotinoyl, methoxyisonicotinoyl, pyrimidincarbonyl, hydroxypyrimidincarbonyl, aminopyrimidincarbonyl, methoxypyrimidincarbonyl, pyridazincarbonyl, hydroxypyridazincarbonyl, aminopyridazincarbonyl, methoxypyrimdazincarbonyl, pyrazincarbonyl, hydroxypyrazincarbonyl, aminopyrazincarbonyl and methoxypyrazincarbonyl.

The absolute configuration of the pleuromutilin backbone is preferably the same as that of natural (+)-pleuromutilin. A preferred embodiment of the present invention therefore relates to the compound as described herein, wherein the compound is represented by Formula (1a)

(1a)

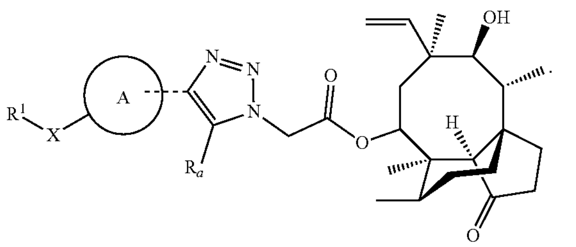

The aromatic ring (A) connects the triazole moiety to the terminal substituent group ($R^1$) through linker (X). Preferably, the aromatic ring-shape is formed by 6 atoms whereby a specific embodiment of the present invention relates to the compound as described herein, wherein A is a 6-membered optionally substituted aromatic ring.

Notably, such a 6-membered aromatic ring may be formed either by carbon atoms or heteroatoms such as N, O, or S. Thus, an embodiment of the present invention relates to the compound as described herein, wherein A is a 6-membered optionally substituted aromatic hydrocarbon or a 6-membered optionally substituted aromatic heterocycle having one or more nitrogen atoms in the ring.

Apart from being connected to the triazole moiety and to the linker, said aromatic ring may also bear a number of different substituent groups. Preferably, but not limited thereto, these are selected from a specific group of substituents which may be especially relevant for obtaining compounds with the desired properties. Therefore, an embodiment of the present invention relates to the compound as described herein, wherein the optional substituents of A are selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$)alkoxy, oxo, cyano, carboxy, carbamoyl, fluoro, chloro, bromo, iodo, and deuterium.

Herein, the term "cyclo($C_3$-$C_8$)alkyl" refers to a radical of a cycloalkane, such as cyclopropane, cyclobutane, cyclopentane, cyclohexane, cycloheptane, and cyclooctane. Also, the term "aryl" refers to a radical of an aromatic ring, such as phenyl, benzyl, and pyridine.

The position of the linker and terminal substituent group on the aromatic ring is considered an important feature for obtaining compounds mediating strong antibacterial and antifungal effects. Preferably, said position is para to the single bond connecting the triazole moiety and the aromatic ring.

Thus, a particular embodiment of the present invention relates to the compound as described herein, wherein the compound is represented by Formula (2)

(2)

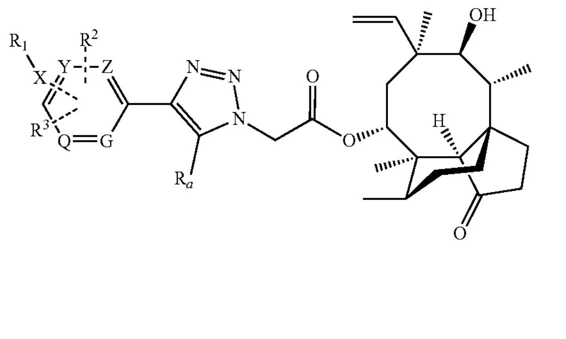

wherein, $R_a$ is selected from the group consisting of hydrogen, hydroxy, hydroxy($C_1$-$C_5$)alkyl, amino, amino($C_1$-$C_5$)alkyl, ($C_1$-$C_5$)alkyl, methoxy, and ethoxy, preferably hydrogen, X is preferably positioned in meta or para and is selected from the group consisting of —O—, —NH—, —S—, optionally substituted ($C_2$-$C_5$)alkenediyl, optionally substituted ($C_2$-$C_5$)alkynediyl, and optionally substituted ($C_1$-$C_5$) alkanediyl, $R^1$ is a radical of an optionally substituted mono- or bicyclic ring system, or $R^1$ is an optionally substituted acyclic system comprising a number of q carbon atoms and q is selected from the group consisting of 0, 1, 2, 3, 4, 5, 6, 7, 8, 9, and 10; or $R^1$—X is cyano;

Y, Z, Q and G are atoms of the aromatic ring and are independently selected from the group consisting of carbon, and nitrogen, $R^2$ and $R^3$ are optional substituents independently selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$) alkoxy, oxo, cyano, carboxy, carbamoyl, fluoro, chloro, bromo, iodo, and deuterium.

Thus, a particular embodiment of the present invention relates to the compound as described herein, wherein the compound is represented by Formula (2a)

(2a)

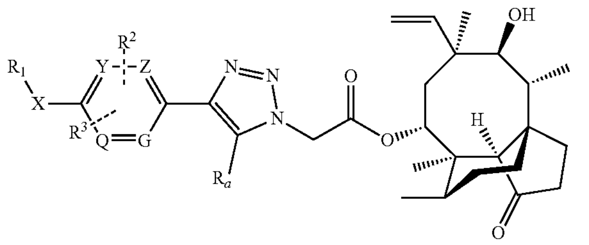

wherein, $R_a$ is selected from the group consisting of hydrogen, hydroxy, hydroxy($C_1$-$C_5$)alkyl, amino, amino($C_1$-$C_5$)alkyl, ($C_1$-$C_5$)alkyl, methoxy, and ethoxy, preferably hydrogen, X is selected from the group consisting of —O—, —NH—, —S—, optionally substituted ($C_2$-$C_5$)alkenediyl, optionally substituted ($C_2$-$C_5$)alkynediyl, and optionally substituted ($C_1$-$C_5$)alkanediyl, $R^1$ is a radical of an optionally substituted mono- or bicyclic ring system, or $R^1$ is an optionally substituted acyclic system comprising a number of q carbon atoms and q is selected from the group consisting of 0, 1, 2, 3, 4, 5, 6, 7, 8, 9, and 10; or $R^1$—X is cyano;

Y, Z, Q and G are atoms of the aromatic ring and are independently selected from the group consisting of carbon, and nitrogen, $R^2$ and $R^3$ are optional substituents independently selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$) alkoxy, oxo, cyano, carboxy, carbamoyl, fluoro, chloro, bromo, iodo, and deuterium.

Yet another particular embodiment of the present invention relates to the compound as described herein, wherein the compound is represented by Formula (2b)

(2b)

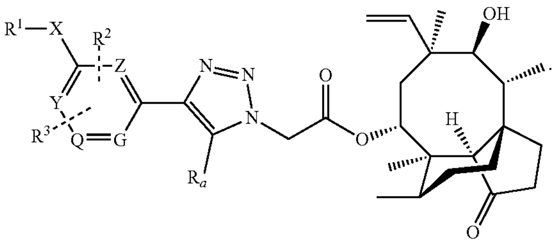

wherein, $R_a$ is selected from the group consisting of hydrogen, hydroxy, hydroxy($C_1$-$C_5$)alkyl, amino, amino($C_1$-$C_5$)alkyl, ($C_1$-$C_5$)alkyl, methoxy, and ethoxy, preferably hydrogen, X is selected from the group consisting of —O—, —NH—, —S—, optionally substituted ($C_2$-$C_5$)alkenediyl, optionally substituted ($C_2$-$C_5$)alkynediyl, and optionally substituted ($C_1$-$C_5$)alkanediyl, $R^1$ is a radical of an optionally substituted mono- or bicyclic ring system, or $R^1$ is an optionally substituted acyclic system comprising a number of q carbon atoms and q is selected from the group consisting of 0, 1, 2, 3, 4, 5, 6, 7, 8, 9, and 10; or $R^1$—X is cyano;

Y, Z, Q and G are atoms of the aromatic ring and are independently selected from the group consisting of carbon, and nitrogen, $R^2$ and $R^3$ are optional substituents independently selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$) alkoxy, oxo, cyano, carboxy, carbamoyl, fluoro, chloro, bromo, iodo, and deuterium.

In this regard, the dotted lines (-----) from the optional substituent groups $R^2$ and $R^3$ each denote a single bond connected to any position of said aromatic ring by substitution of one of the hydrogen atoms of the aromatic ring.

An embodiment of the present invention relates to the compound as described herein, wherein $R^2$ is selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$) alkoxy, oxo, cyano, carboxy, carbamoyl, fluoro, chloro, bromo, iodo, and deuterium.

An embodiment of the present invention relates to the compound as described herein, wherein $R^3$ is selected from the group consisting of ($C_1$-$C_6$)alkyl, ($C_2$-$C_6$)alkenyl, ($C_2$-$C_6$)alkynyl, aryl, cyclo($C_3$-$C_8$)alkyl, amino, ($C_1$-$C_6$)alkylamino, di($C_1$-$C_6$)alkylamino, nitro, hydroxyl, ($C_1$-$C_6$) alkoxy, oxo, cyano, carboxy, carbamoyl, fluoro, chloro, bromo, iodo, and deuterium.

An embodiment of the present invention relates to the compound as described herein, wherein Y is a carbon or nitrogen atom, Z is a carbon or nitrogen atom, Q is a carbon or nitrogen atom, and G is a carbon or nitrogen atom.

The aromatic ring may be formed by carbon atoms, or carbon atoms and heteroatoms. However, a preferred embodiment of the present invention relates to the compound as described herein, wherein Y, Z, Q, and G are carbon atoms and X is an optionally substituted ($C_1$-$C_5$) alkanediyl.

Apart from connecting the aromatic ring to the terminal substituent group, the linker may also bear a number of different substituent groups for the purpose of increasing the physicochemical properties of the compounds. Preferably, but not limited thereto, these are selected from a specific group of substituents which may be particularly relevant for obtaining compounds with the desired properties. An embodiment of the present invention thus, relates to the compound as described herein, wherein the optional substituents of X are selected from the group consisting of fluoro, chloro, bromo, iodo, $(C_1\text{-}C_3)$alkyl, and deuterium.

A number of compounds of particular interest is covered by an embodiment of the present invention and relates to the compound as described herein, wherein the compound is selected from the group consisting of

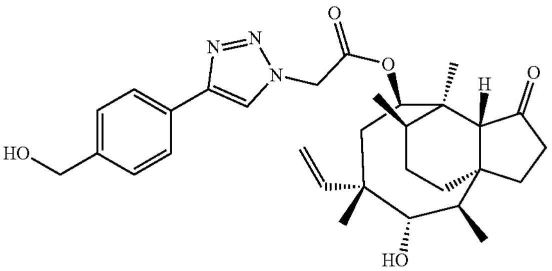

,

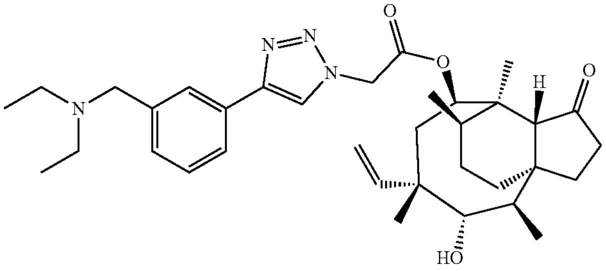

,

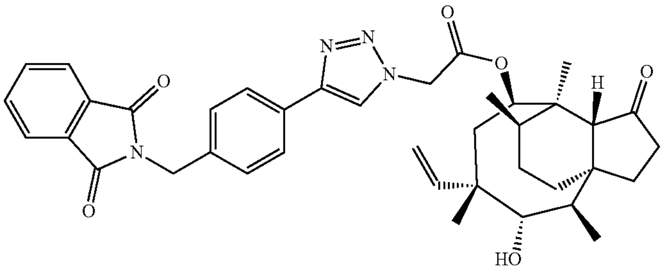

,

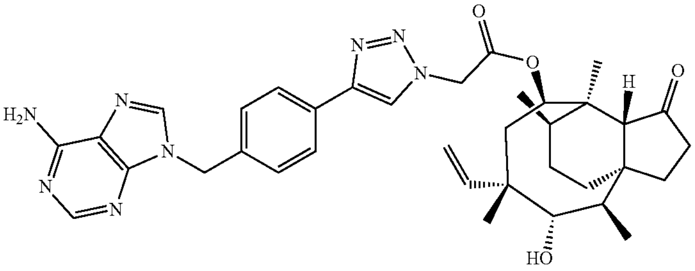

,

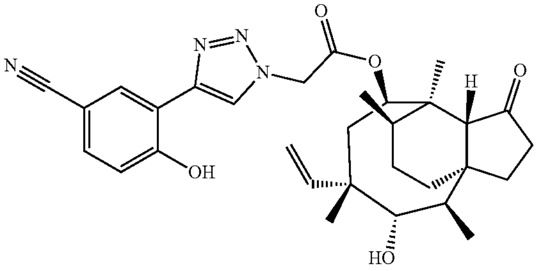

,

-continued
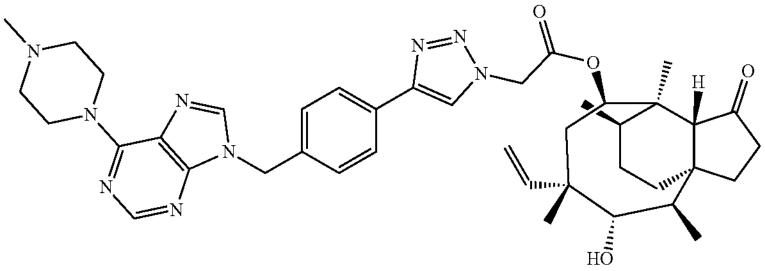
,
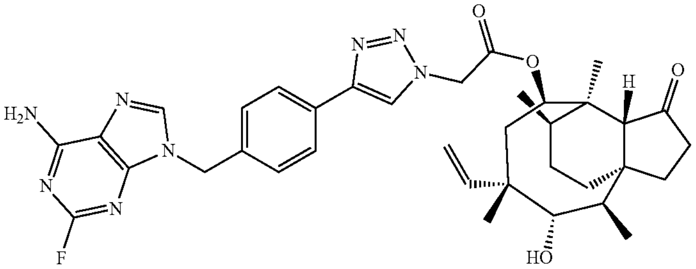
,
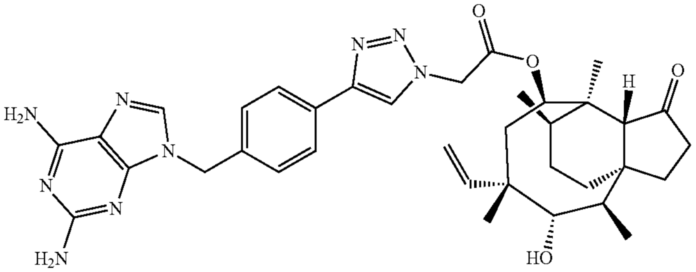
,
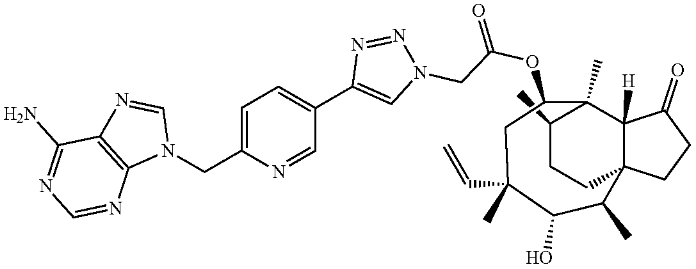
,
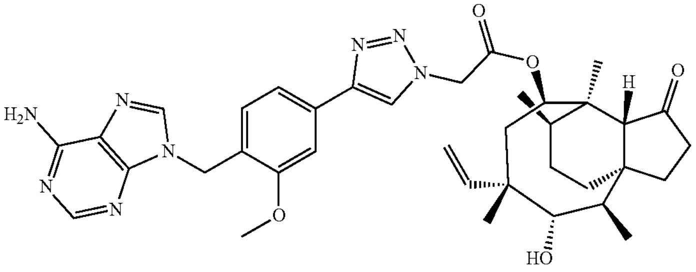
,
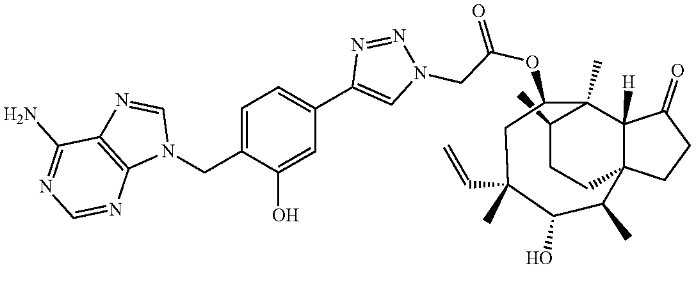
, -continued
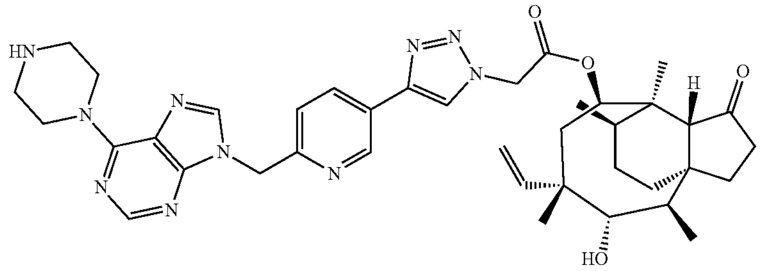
,
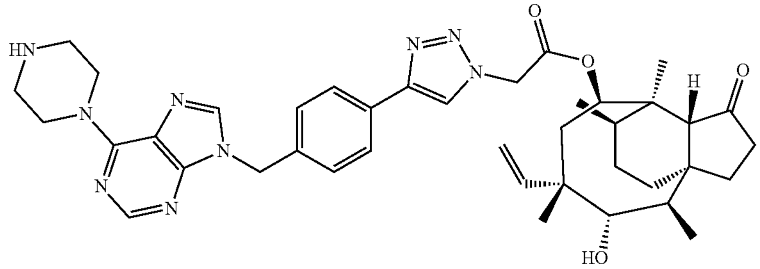
,
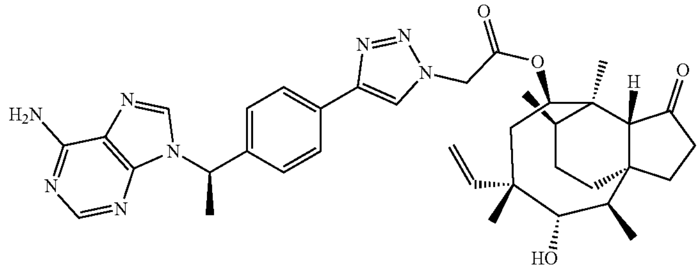
,
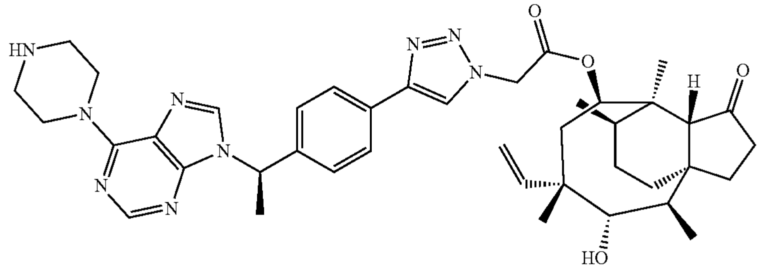
,
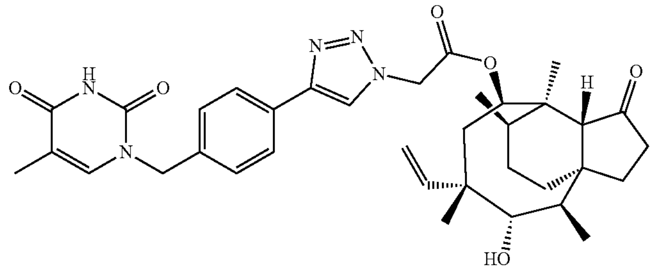
,
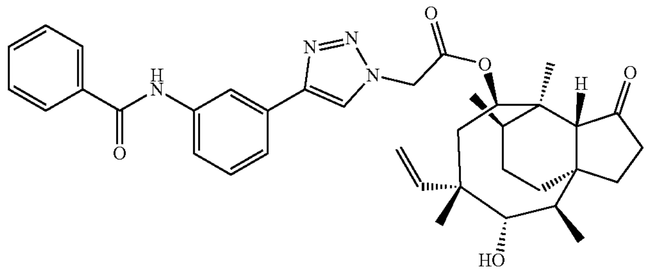
, -continued

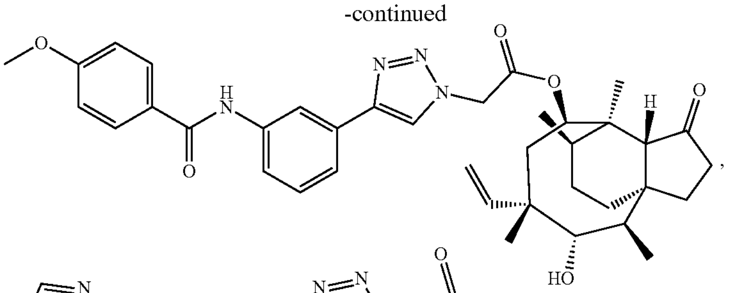

,

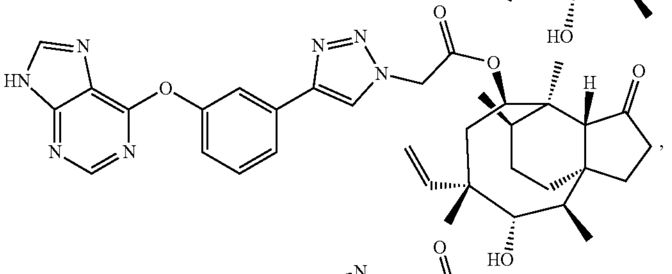

,

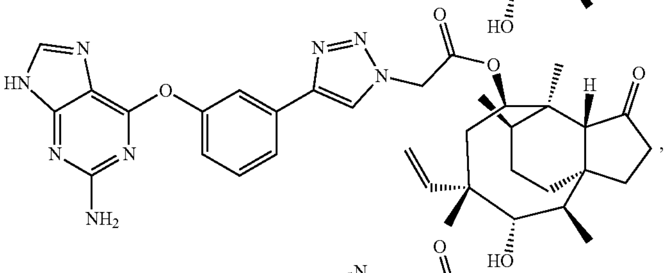

,

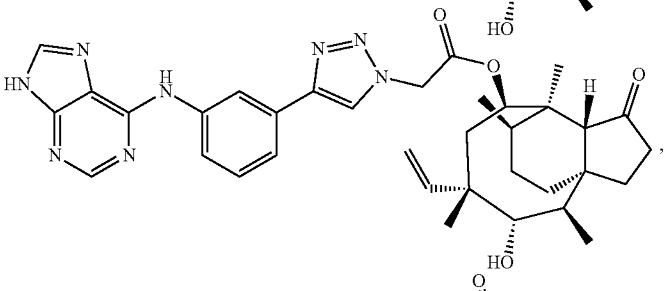

, and

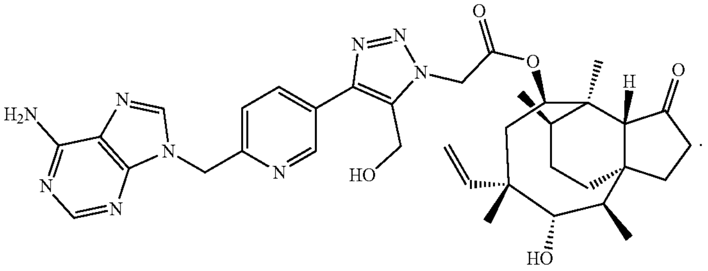

.

The linker is preferably a methylene bridge, i.e. a —$CH_2$— moiety, whereby a particular embodiment of the present invention relates to the compound as described herein, wherein the compound is represented by Formula (3) or (3a)

(3)

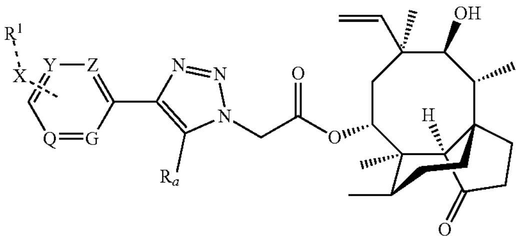

or

-continued (3a)

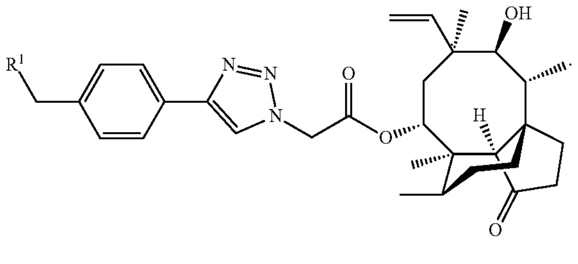

The terminal substituent group is considered a main component for obtaining compounds that are particularly effective at treating bacterial infections and fungal infections. In addition, the inventors were surprised to find that having an alkylene bridge in the para position of the aromatic ring (e.g. the benzene ring in Formula 3) or 3a) in combination with utilization of specific heterocycles at $R^1$, can lead to compounds with increased antibacterial activity compared to commercial drugs.

Thus, a preferred embodiment of the present invention relates to the compound as described herein, wherein $R^1$ is an optionally substituted mono- or bicyclic heterocycle.

An embodiment of the present invention relates to the compound as described herein, wherein $R^1$ is an optionally substituted mono- or bicyclic heterocycle selected from the group consisting of pyrrole, furan, thiophene, pyrrolidine, tetrahydrofuran, tetrahydrothiophene, imidazolidine, pyrazolidine, oxazolidine, isoxazolidine, thiazolidine, isothiazolidine, dioxolane, dithiolane, imidazole, pyrazole, oxazole, isoxazole, thiazole, isothiazole, triazoles, furazan, oxadiazole, thiadiazole, dioxazole, dithiazole, piperidine, tetrahydropyran, thiane, pyridine, pyran, thiopyran, diazinane, morpholine, thiomorpholine, dioxane, diazine, oxazine, thiazine, dioxine, triazinane, trioxane, trithiane, triazine, purine, adenine, guanine, xanthine, hypoxanthine, phthalimide, quinoxaline, phthalazine, quinazoline, naphthyridine, pyridopyrimidine, pyridopyrazine, pteridine, chromene, isochromene, benzooxazine, indoline, indole, isoindole, indazole, benzimidazole, azaindole, azaindazole, benzofuran, isobenzofuran, benzothiophene, benzoisoxazole, benzoisothiazole, benzooxazole, benzothiazole, tetrahydroquinoline, quinoline, isoquinoline, and derivatives thereof.

An embodiment of the present invention relates to the compound as described herein, wherein $R^1$ is an optionally substituted unsaturated mono- or bicyclic heterocycle. A more specific embodiment of the present invention relates the compound as described herein, wherein $R^1$ is an optionally substituted unsaturated mono- or bicyclic heterocycle selected from the group consisting of pyrrole, furan, thiophene, imidazole, pyrazole, oxazole, isoxazole, thiazole, isothiazole, triazoles, furazan, oxadiazole, thiadiazole, dioxazole, dithiazole, pyridine, pyran, thiopyran, diazine, oxazine, thiazine, dioxine, triazine, purine, adenine, guanine, xanthine, hypoxanthine, phthalimide, quinoxaline, phthalazine, quinazoline, naphthyridine, pyridopyrimidine, pyridopyrazine, pteridine, chromene, isochromene, benzooxazine, indoline, indole, isoindole, indazole, benzimidazole, azaindole, azaindazole, benzofuran, isobenzofuran, benzothiophene, benzoisoxazole, benzoisothiazole, benzooxazole, benzothiazole, tetrahydroquinoline, quinoline, isoquinoline, and derivatives thereof.

However, a preferred embodiment of the present invention relates to the compound as described herein, wherein $R^1$ is selected from the group consisting of nucleobases, modified nucleobases, purine, derivatives of purine, pyrimidine, derivatives of pyrimidine, pyridines, derivatives of pyridines, imidazoles, derivatives of imidazoles, pyrazoles, derivatives of pyrazoles, azoles, derivatives of azoles, thiophenes, derivatives of thiophenes, furans, derivatives of furans, diazines, derivatives of diazines, phthalimides, derivatives of phthalimides, piperazines, derivatives of piperazines, triazines, and derivatives of triazines.

In the present context, examples of nucleobases are compounds such as adenine, cytosine, guanine, thymine, uracil, xanthine, hypoxanthine, purine, and derivatives thereof.

A particularly preferred embodiment of the present invention relates to the compound as described herein, wherein $R^1$ is selected from the group consisting of adenine, cytosine, guanine, thymine, uracil, xanthine, hypoxanthine, purine, phthalimide, methylpiperazine, and pyrimidine.

The terminal substituent group may also bear a number of different substituent groups for the purpose of increasing the physicochemical properties and/or potencies of the compounds. Preferably, but not limited thereto, these are selected from a specific group of substituents which may be especially relevant for obtaining such compounds.

Thus, an embodiment of the present invention relates to the compound as described herein, wherein the optional substituents of $R^1$ are selected from the group consisting of fluoro, chloro, bromo, iodo, $(C_1$-$C_6)$alkyl, $(C_2$-$C_6)$alkenyl, $(C_2$-$C_6)$alkynyl, hydroxyl, sulfanyl, formyl, amino, imino, cyano, nitro, oxo, carboxy, carbamoyl, thiocarboxy, sulfo, sulfino, phosphono, $(C_1$-$C_6)$alkyloxycarbonyl, $(C_2$-$C_6)$alkenyloxycarbonyl, $(C_2$-$C_6)$alkynyloxycarbonyl, $(C_1$-$C_6)$alkylamino, di$(C_1$-$C_6)$alkylamino, hydrazinocarbonyl, $(C_1$-$C_6)$alkoxy, $(C_1$-$C_3)$alkylpiperazino, piperazino, amino$(C_1$-$C_6)$alkylamino, guanidino, cyclo$(C_3$-$C_8)$alkyl, aryl, and deuterium. However, a particular embodiment of the present invention relates to the compound as described herein, wherein the optional substituents of $R^1$ are selected from the group consisting of fluoro, chloro, bromo, iodo, $(C_1$-$C_6)$alkyl, hydroxyl, amino, nitro, $(C_1$-$C_6)$alkylamino, di$(C_1$-$C_6)$alkylamino, $(C_1$-$C_6)$alkoxy, $(C_1$-$C_3)$alkylpiperazino, amino$(C_1$-$C_6)$alkylamino, guanidino, and deuterium.

As previously outlined herein, the inventors surprisingly discovered that specific species of compounds of the present invention possess increased antibacterial activity compared to commercial drugs, such as Valnemulin and Retapamulin. An example thereof, is the compound according to Formula 3, wherein the terminal substituent group is an adenine group. A particularly preferred embodiment of the present invention therefore relates to the compound as described herein, wherein the compound is represented by Formula (4)

(4)

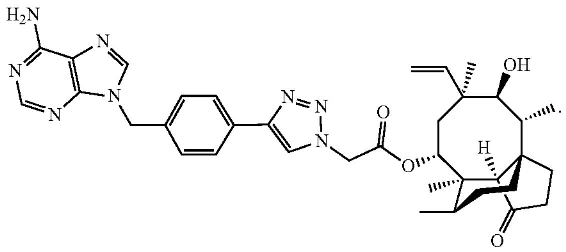

The compounds of the present invention are considered suitable for use in pharmaceutical compositions.

Thus, another aspect of the present invention relates to a pharmaceutical composition comprising a compound as described herein or a pharmaceutically acceptable salt thereof.

An embodiment of the present invention relates to the pharmaceutical composition as described herein, wherein the composition further comprises pharmaceutically acceptable components independently selected from the group consisting of excipients, carriers, diluents and adjuvants. Another embodiment of the present invention relates to the pharmaceutical composition as described herein, wherein the composition further comprises one or more additional therapeutic agents.

Yet, another aspect of the present invention relates to a compound as described herein or a pharmaceutical composition as described herein for use as a medicament.

The compounds of the present invention inhibit bacterial and fungal infections. Diseases and conditions caused by bacteria alone, or fungi alone, or simultaneous infections of both bacteria and fungi together, may therefore be treated or prevented by administering one of the compounds or pharmaceutical compositions comprising one of the compounds, to a subject in need thereof, such as a human.

Still another aspect of the present invention relates to a compound as described herein or a pharmaceutical composition as described herein for use in the treatment or prevention of a bacterial infection and/or a fungal infection.

Without being restricted to the following groups, certain groups of gram-positive, gram-negative, and other bacteria are considered especially targetable by the compounds of the present invention. Thus, an embodiment of the present invention relates to the compound for use or pharmaceutical composition for use as described herein, wherein the bacterial infection is caused by bacteria selected from the group consisting of *Streptococcus pneumoniae*, alpha-hemolytic *streptococci*, beta-hemolytic *streptococci, Streptococcus aureus*, such as methicillin-resistant *Staphylococcus aureus* (MRSA), *Staphylococcus epidermidis, Staphylococcus haemolyticus, Enterococcus*, such as *Enterococcus faecalis*, vancomycin-resistant *enterococci* (VRE), *Listeria monocytogenes, Cutibacterium acnes*, enterobacteriacae, such as *Escherichia coli, Morganella morganelil, Haemophilus influenza, Mycoplasma* pneumonia, and *Chlamydia trachomatis.*

However, the compounds of the present invention effectively inhibit all types of bacteria, yet gram-positive and gram-negative bacteria are especially relevant. A particular embodiment of the present invention therefore relates to the compound for use or pharmaceutical composition for use as described herein, wherein the bacterial infection is caused by gram-positive and/or gram-negative bacteria.

Furthermore, a preferred embodiment of the present invention relates to the compound for use or pharmaceutical composition for use as described herein, wherein the bacterial infection is caused by gram-positive bacteria. More specifically, an embodiment of the present invention therefore relates to the compound for use or pharmaceutical composition for use as described herein, wherein the bacterial infection is caused by gram-positive bacteria selected from the group consisting of *Streptococcus pneumoniae*, alpha-hemolytic *streptococci*, beta-hemolytic *streptococci, Streptococcus aureus*, such as methicillin-resistant *Staphylococcus aureus* (MRSA), *Staphylococcus epidermidis, Staphylococcus haemolyticus, Enterococcus*, such as *Enterococcus faecalis*, vancomycin-resistant enterococci (VRE), *Listeria monocytogenes*, and *Cutibacterium acnes.*

In an even more preferred embodiment, the present invention relates to the compounds for use or pharmaceudical composition for use as described herein, wherein the bacterial infection is caused by bacteria selected form the group consisting of *Streptococcus pneumonia*, methicillin-resistant *Staphylococcus aureus* (MRSA), *Enterococcus faecalis* and vancomycin-resistant enterococci (VRE).

Without being restricted to the following groups, certain groups of fungi are considered especially targetable by the compounds of the present invention. Thus, an embodiment of the present invention relates to the compound for use or pharmaceutical composition for use as described herein, wherein the fungal infection is caused by fungi selected from the group consisting of *Candida* species, such as *Candida albicans, Candida glabrata, Candida rugosa, Candida parapsilosis, Candida tropicalis, Candida dubliniensis*, and *Candida auris.*

The compounds are considered potent against bacteria that have developed resistance to common antibiotic agents, such as methicillin, oxacillin, and vancomycin. An embodiment of the present invention therefore relates to the compound for use or pharmaceutical composition for use as described herein, wherein the bacterial infection is caused by multidrug-resistant bacteria.

Thus, a particular embodiment of the present invention relates to the compound for use or pharmaceutical composition for use as described herein, wherein the bacterial infection is caused by bacteria selected from the group consisting of methicillin-resistant *Staphylococcus aureus* (MRSA), and vancomycin-resistant enterococci (VRE). However, a particularly preferred embodiment of the present invention relates to the compound for use or pharmaceutical composition for use as described herein, wherein the bacterial infection is caused by methicillin-resistant *Staphylococcus aureus* (MRSA).

The route of administration may be any conventional route of administration, wherein the route of administration is chosen to fit the specific treatment. Therefore, an embodiment of the present invention relates to the compound or pharmaceutical composition for use as described herein, wherein the compound or pharmaceutical composition is administered by a route selected from the group consisting of orally, parenterally, intravenously, intradermally, subcutaneously, and topically, in liquid or solid form.

The components for the treatment described herein may be provided as a kit for easy application to a subject in need thereof.

Therefore, an additional aspect of the present invention relates to a kit comprising:

i) a compound as described herein or a pharmaceutical composition as described herein, ii) one or more additional therapeutic agents, and iii) optionally, instructions for use.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Synthesis Procedures

Materials

Commercially available solvents and starting materials were used unless otherwise stated. TLC was performed using TLC silica gel 60 F254 plates and visualized at 254 nm or by staining with PMA, ninhydrin or $KMnO_4$ stains. For Flash Chromatography purification, silica gel 60 (0.040-0.063 mm, Merck) was used. $^1H$ and $^{13}C$ spectra were recorded at 400 and 101 MHz respectively, on a Bruker Avance III 400 at 300 K using different types of deuterated solvents, such as deuterated dimethyl sulfoxide (DMSO) and chloroform ($CDCl_3$). Reverse-phase liquid chromatography (RPLC) analysis was performed using a Gemini C18 column (5 μm, 4.6 mm×150 mm); flow, 1 mL/min; 10% acetonitrile (MeCN) in water (0-1 min), 10-100% MeCN in water (1-10 min), 100% MeCN (11-15 min), both solvents with 0.1% trifluoro acetic acid as modifier, UV detection at 254 nm. (+)-Pleuromutilin (A1) was bought form Sigma Aldrich.

General Procedure

General Procedure 1 for Carbonate-Mediated Deprotection of Trimethylsilyl-Acetylenes The trimethylsilyl protected acetylene analogue (B1) (1 eq.) was dissolved in methanol (MeOH, 140 mM) after which $K_2CO_3$ was added (1 eq.). The suspension was stirred for 1 to 24 hours before it was concentrated in vacuo. The residue was diluted with water and extracted with diethyl ether ($Et_2O$). The combined organics were washed with brine, dried over $MgSO_4$ and evaporated in vacuo. The crude was purified by Flash chromatography in ethyl acetate and petroleum ether (EtOAc:PE) unless otherwise stated to yield the deprotected acetylene as an oil or solid.

General Procedure 2 for CuAAC Reaction

A small microwave-vial was charged with 22-azido-22-deoxypleuromutilin (A3) (0.12-0.20 mmol), the appropriate alkyne (0.12-0.20 mmol), sodium ascorbate (0.025-0.040 mmol) and $CuSO_4 \cdot 5H_2O$ (0.012-0.020 mmol) before degassed tert-butanol and water (t-BuOH:$H_2O$) (1:1 v/v, 1.25-14 mL) was added. The vial was sealed and irradiated in a microwave reactor at 110° C. (normal absorption mode) for 30 min. The reaction mixture was concentrated in vacuo and the resulting residue was purified by Flash chromatography in either EtOAc:PE (0-100%), EtOAc:MeOH (0-20%) or MeOH:DCM (0-20%) to afford the product as white crystals/foam.

General Procedure 3 for Nucleophilic Aromatic Substitution of 6-Chloro Purines

In a small microwave vial, the chloro-purin B6 (0.167-0.335 mmol) was suspended in anhydrous ethanol (1.9-3.7 mL) after which the appropriate amine was added (4.eq.). The vial was sealed and stirred at 75° C. for 4 hours. The reaction mixture was concentrated and the resulting residue was purified by Flash chromatography (0-3% MeOH:DCM) or used without further purification.

A: Synthesis of Azido-Pleuromutilin for Click Chemistry

22-O-mesylpleuromutilin A2

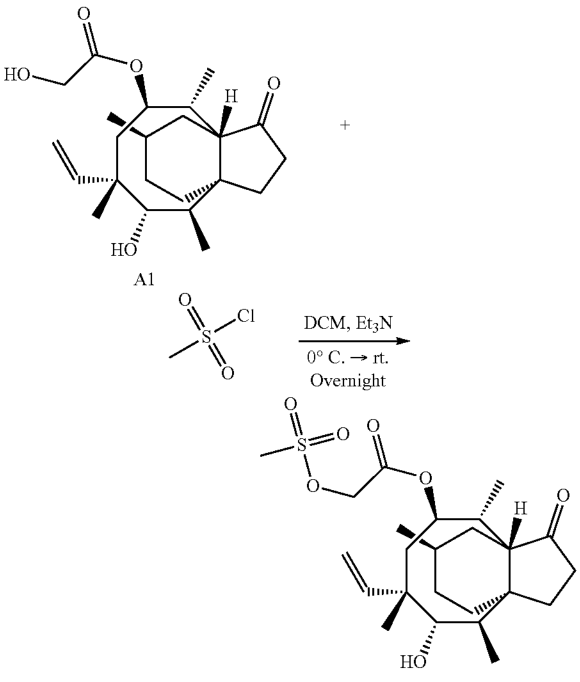

A1

A2

A large dry microwave-vial was charged with (+)-pleuromutilin (A1) (2.00 g, 5.28 mmol) and vac-filled 3× with argon before anhydrous dichloromethane (10.0 mL) and anhydrous triethylamine (0.89 mL, 6.35 mmol) was added. The mixture was cooled to 0° C. followed by dropwise addition of methanesulfonyl chloride (0.41 mL, 5.28 mmol) after which the vial was capped. The mixture was allowed to reach room temperature and stirred overnight resulting in consumption of A1. Saturated ammonium chloride (1.5 mL) was added to quench the reaction and the mixture was separated. The aqueous layer was washed with diethyl ether (3×10 mL). The organic layers were collected and washed with brine, dried over $Na_2SO_4$ and evaporated in vacuo. The resulting residue was purified by Flash chromatography (EtOAc:PE, 5%→10%→20%→50%) to give 1.49 g of 22-O-mesylpleuromutilin (A2) (62%, 3.27 mmol); $^1$H NMR (400 MHz, DMSO) δ 6.14 (dd, J=17.8, 11.2 Hz, 1H), 5.62 (d, J=8.3 Hz, 1H), 5.15-5.03 (m, 2H), 4.89-4.72 (m, 2H), 4.56 (d, J=5.9 Hz, 1H), 3.47-3.39 (m, 1H), 3.24 (s, 3H), 2.47-2.40 (m, 1H), 2.27-2.01 (m, 4H), 1.72-1.57 (m, 2H), 1.56-1.22 (m, 7H), 1.07 (s, 3H), 0.83 (d, J=7.0 Hz, 3H), 0.63 (d, J=6.9 Hz, 3H); $^{13}$C NMR (101 MHz, DMSO) δ 216.99, 170.28, 165.39, 140.73, 115.34, 72.55, 70.38, 65.78, 59.71, 57.16, 44.93, 44.20, 43.18, 41.54, 40.17, 39.96, 39.75, 39.54, 39.33, 39.13, 38.92, 37.59, 36.49, 36.23, 33.97, 30.07, 28.63, 26.55, 24.45, 20.72, 15.91, 14.42, 14.06, 11.51; HRMS (ESI): m/z calculated for $C_{23}H_{36}NaO_7S$ (M+Na+) 479.2074 found 479.2078.

22-azido-22-deoxypleuromutilin A3

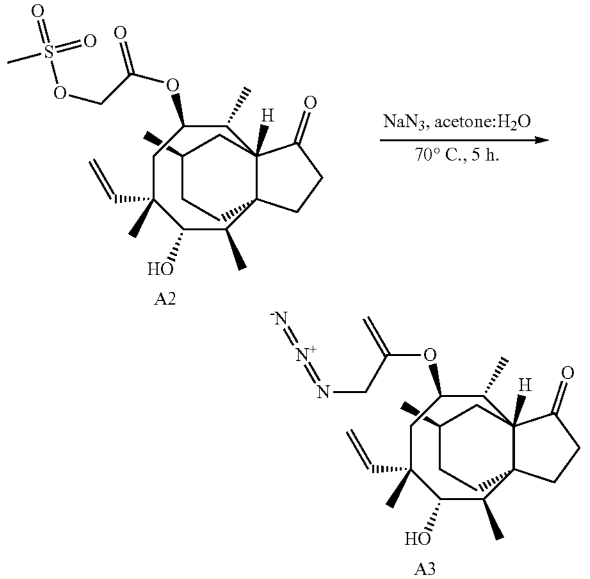

A2

A3

Compound A2 (1.43 g, 3.13 mmol) was dissolved in acetone (14.0 mL) to which a solution of $NaN_3$ (254 mg, 3.91 mmol) in water (5.3 mL) was slowly added. The mixture was refluxed at 70° C. for 5 hours before cooling to room temperature and concentration in vacuo. The residue was dissolved in dichloromethane (50 mL) and washed with water (15 mL), brine (15 mL) and dried over $Na_2SO_4$. The organic layer was evaporated in vacuo before purification by Flash chromatography ($SiO_2$, 34×100 mm, EtOAc:PE, 5%→10%→30%) to yield 1.035 g of 22-azido-22-deoxypleuromutilin (A3) (82%, 2.56 mmol); $^{1}$H NMR (400 MHz, $CDCl_3$) δ 6.49 (dd, J=17.4, 11.0 Hz, 1H, HA), 5.86 (d, J=8.5 Hz, 1H, HB), 5.37 (dd, J=11.0, 1.5 Hz, 1H, HC), 5.22 (dd, J=17.4, 1.6 Hz, 1H, HD), 3.77 (s, 2H, HE), 3.36 (dd, J=10.7, 6.6 Hz, 1H, HF), 2.34 (p, J=7.1 Hz, 1H, HG), 2.30-2.16 (m, 2H, HH), 2.16-2.08 (m, 2H, HI), 1.78 (dq, J=14.5, 3.1 Hz, 1H, HJ), 1.73-1.60 (m, 2H, HK), 1.57 (s, 1H, HL), 1.56-1.48 (m, 1H, HM), 1.47 (s, 3H, HN), 1.44 (d, J=2.2 Hz, 1H, HO), 1.40 (dq, J=11.1, 3.9 Hz, 1H, HP), 1.33 (d, J=16.1 Hz, 1H, HQ), 1.18 (s, 3H, HR), 1.17-1.09 (m, 1H, HS), 0.89 (d, J=7.0 Hz, 3H, HT), 0.73 (d, J=7.0 Hz, 3H, HU); $^{13}$C NMR (101 MHz, $CDCl_3$) δ 216.7 (C3), 167.2 (C21), 138.8 (C19), 117.5 (C20), 74.6 (C11), 70.3 (C14), 58.2 (C4), 51.2 (C22), 45.5 (C9), 44.9 (C13), 44.0 (C12), 41.9 (C5), 36.7 (C6), 36.1 (C10), 34.4 (C2), 30.4 (C8), 26.9 (C7), 26.4 (C18), 24.9 (C1), 16.7 (C16), 14.9 (C15), 11.5 (C17); HRMS (ESI): m/z calculated for $C_{22}H_{33}N_3NO_4$ (M+Na+) 426.2363 found 426.2345.

B: Synthesis of Alkynes for Click Chemistry (4-ethynylphenyl)methanol B2

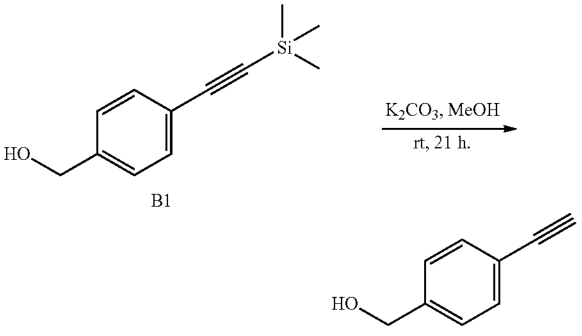

B1

B2

General Procedure 1 was applied with the trimethylsilyl acetylene (1.50 g, 7.34 mmol) dissolved in MeOH (52 mL) after which $K_2CO_3$ was added (1.01 g, 7.34 mmol). The suspension was stirred for 21 h. at rt. before it was concentrated in vacuo. The resulting residue was purified by Flash Chromatography (EtOAc:PE, 5-20%) to afford 782 mg of B2 (81%, 5.92 mmol); $^{1}$H NMR (400 MHz, $CDCl_3$) δ 7.51-7.46 (m, 2H), 7.32 (d, J=8.5 Hz, 2H), 4.70 (s, 2H), 3.07 (s, 1H); $^{13}$C NMR (101 MHz, $CDCl_3$) δ 141.61, 132.34, 126.74, 121.37, 83.49, 77.20, 64.89; EI MS m/z calculated for $C_9H_8O$ (M+) 132.0 found 132.0.

1-(bromomethyl)-4-ethynylbenzene B3

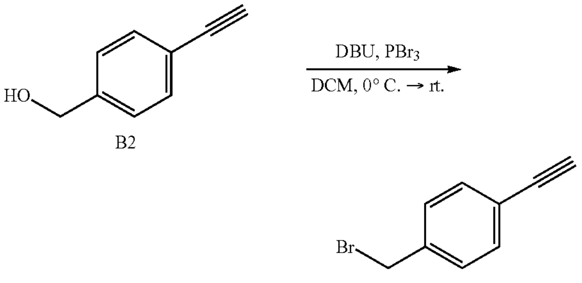

B2

B3

Compound B2 (735 mg, 5.56 mmol) and 1,8-Diazabicyclo(5.4.0)undec-7-ene (DBU, 1.10 g, 7.63 mmol) was dissolved in anhydrous dichloromethane (DCM, 5.6 mL). The vessel was purged with argon and cooled to 0° C. before phosphorous tribromide (0.58 mL, 6.12 mmol) was added dropwise. The mixture was stirred for 19 hours during which it reached room temperature (rt.). The reaction mixture was quenched with ice water (30 mL) before extraction with dichloromethane (3x30 mL). The combined organic layers were washed with 5% $H_2SO_4$ (2x30 mL), saturated $NaHCO_3$ (2x30 mL) and brine (2x30 mL) before being dried over $MgSO_4$. Evaporation in vacuo yielded 938 mg of B3 (87%, 4.81 mmol). No further purification necessary; $^{1}$H NMR (400 MHz, $CDCl_3$) δ 7.49-7.44 (m, 2H), 7.37-7.32 (m, 2H), 4.47 (s, 2H), 3.10 (s, 1H); $^{13}$C NMR (101 MHz, $CDCl_3$) δ 138.40, 132.52, 129.00, 122.29, 83.10, 77.99, 32.68; EI MS m/z calculated for $C_9H_7Br$ (M+) 194.0 found 193.9.

9-(4-ethynylbenzyl)-9H-purin-6-amine B4

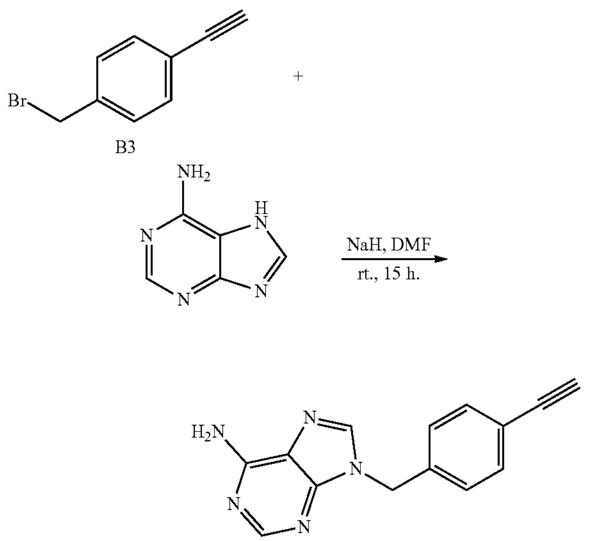

B3

B4

In a small, dry microwave vial, adenine (73 mg, 0.539 mmol) was suspended in anhydrous dimethylformamide (DMF, 2.6 mL) before addition of NaH (60% in paraffin oil, 26 mg, 0.648 mmol). The vial was purged with argon and the suspension stirred for 30 min. before 1-(bromomethyl)-4-ethynylbenzene (B3) (100 mg, 0.513 mmol) was added. The mixture was stirred for additional 15 hours before the solvent was removed in vacuo. The residue was re-dissolved in MeOH and evaporated onto Celite 545 and purified by Flash Chromatography (MeOH:DCM, 1-5%) to yield 62 mg (49%, 0.249 mmol) of (B4); $^{1}$H NMR (400 MHz, DMSO) δ 8.26 (s, 1H, HA), 8.14 (s, 1H, HB), 7.45 (d, J=8.2 Hz, 2H, HC), 7.30 (d, J=8.3 Hz, 2H, HD), 7.25 (s, 2H), 5.39 (s, 2H, HF), 4.18 (s, 1H, HG); $^{13}$C NMR (101 MHz, DMSO) δ 155.9 (C6), 152.6 (C4), 149.4 (C2), 140.7 (C8), 137.9 (C10), 131.9 (C12), 127.7 (C11), 121.0 (C13), 118.6 (C1), 83.0 (C14), 80.9 (C15), 45.7 (C9); HRMS (ESI): m/z calculated for $C_{14}H_{12}N_5$ (M+H+) 250.1087 found 250.1090.

2-(4-ethynylbenzyl)isoindoline-1,3-dione B5

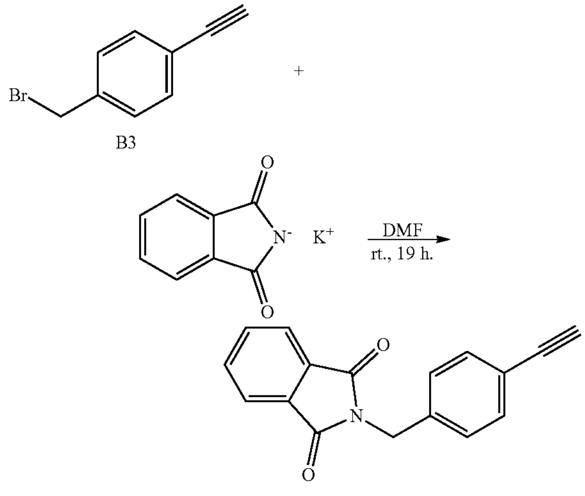

B5

In a small, dry microwave vial, a solution of B3 (200 mg, 1.03 mmol) in anhydrous DMF (0.51 mL) was carefully added potassium phthalimide (218 mg, 1.03 mmol). The vial was sealed and stirred at rt. for 19 hours after which it was diluted with $H_2O$ (10 mL) followed by extraction with DCM (5×10 mL). The combined organic layers were washed with brine (10 mL), dried over $Na_2SO_4$ and evaporated in vacuo. The resulting residue was purified by Flash Chromatography (EtOAc:PE, 5-20%) to afford 215 mg of the title compound B5 (80%, 0.824 mmol); $^{1}$H NMR (400 MHz, $CDCl_3$) δ 7.85 (dd, J=5.5, 3.1 Hz, 2H), 7.75-7.69 (m, 2H), 7.46-7.41 (m, 2H), 7.41-7.36 (m, 2H), 4.84 (s, 2H), 3.05 (s, 1H) (App. 34.A); $^{13}$C NMR (101 MHz, $CDCl_3$) δ 167.92, 137.00, 134.07, 132.44, 132.09, 128.54, 123.42, 121.73, 83.26, 77.46, 41.32; HRMS (ESI): m/z calculated for $C_{17}H_{12}NO_2$ (M+H+) 262.0863 found 262.0966.

6-chloro-9-(4-ethynylbenzyl)-9H-purine B6

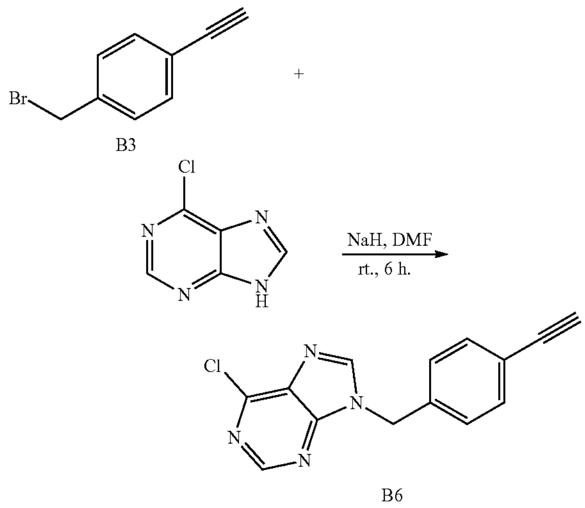

B6

In a small, dry microwave vial, 6-chloro-9H-purine (167 mg, 1.08 mmol) was suspended in anhydrous DMF (5.1 mL) before addition of NaH (60% in paraffin oil, 52 mg, 1.30 mmol). The vial was purged with argon and the suspension stirred for 30 min. before compound B3 (200 mg, 1.03 mmol) was added. The mixture was stirred for additional 6 hours before the solvent was removed in vacuo. The residue was re-dissolved in MeOH and evaporated onto Celite 545 and purified by Flash Chromatography (MeOH:DCM, 1-3%) to yield 150 mg (52%, 0.558 mmol) of B6; $^{1}$H NMR (400 MHz, DMSO) δ 8.85 (s, 1H, HA), 8.79 (s, 1H, HB), 7.46 (d, J=8.3 Hz, 2H, HC), 7.35 (d, J=8.4 Hz, 2H, HD), 5.56 (s, 2H, HE), 4.20 (s, 1H, HF); $^{13}$C NMR (101 MHz, DMSO) δ 151.8 (C2), 151.7 (C4), 149.2 (C6), 147.5 (C8), 136.8 (C10), 132.1 (C12), 130.9 (C1), 127.9 (C11), 121.4 (C13), 83.0 (C14), 81.2 (C15), 46.7 (C9); HRMS (ESI): m/z calculated for $C_{14}H_{10}ClN_4$ (M+H+) 269.0589 found 269.0584.

9-(4-ethynylbenzyl)-6-(4-methylpiperazin-1-yl)-9H-purine B7

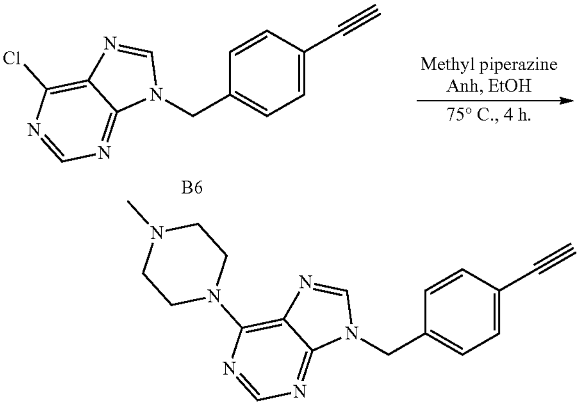

B7

In accordance with general procedure 3, the chloro-purin B6 (45 mg, 0.167 mmol) was suspended in anhydrous ethanol (1.9 mL) after which N-methylpiperazine (0.08 mL, 0.720 mmol) was added. The vial was sealed and stirred at 75° C. for 3.5 hours. Yield: 55 mg (99%, 0.166 mmol); $^{1}$H NMR (400 MHz, $CDCl_3$) δ 8.37 (s, 1H), 7.70 (s, 1H), 7.45 (d, J=8.3 Hz, 2H), 7.20 (d, J=8.4 Hz, 2H), 5.36 (s, 2H), 4.34 (s, 4H), 3.08 (s, 1H), 2.55 (t, J=5.1 Hz, 4H), 2.35 (s, 3H); $^{13}$C NMR (101 MHz, $CDCl_3$) δ 152.95, 151.71, 150.04, 137.00, 135.48, 131.69, 126.50, 121.20, 118.80, 81.94, 76.90, 54.13, 52.39, 45.66, 45.19, 44.04; HRMS (ESI): m/z calculated for $C_{19}H_{21}N_6$ (M+H+) 333.1822 found 333.1834.

9-(4-ethynylbenzyl)-2-fluoro-9H-purin-6-amine B8

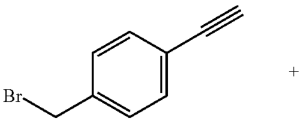

-continued

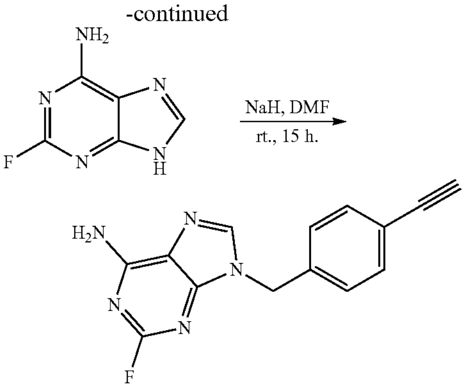

In a small, dry microwave vial, 2-fluoro-adenine (150 mg, 0.980 mmol) was suspended in anhydrous DMF (4.5 mL) before addition of NaH (60% in paraffin oil, 42 mg, 1.06 mmol). The vial was purged with argon and the suspension stirred for 30 min. before compound B3 (206 mg, 1.06 mmol) was added. The mixture was stirred for additional 6 hours before the solvent was removed in vacuo. The residue was re-dissolved in MeOH and evaporated onto Celite 545 and purified by Flash Chromatography (MeOH:DCM, 5%) to yield 135 mg (52%, 0.510 mmol) of B8; $^1$H NMR (400 MHz, DMSO) δ 8.24 (s, 1H), 7.84 (s, 2H), 7.47 (d, J=8.3 Hz, 2H), 7.31-7.27 (m, 2H), 5.34 (s, 2H), 4.20 (s, 1H); $^{13}$C NMR (DMSO, 101 MHz) δ 159.7, 157.7, 157.5, 150.8, 150.6, 141.2, 137.5, 132.0, 127.6, 121.1, 117.0, 83.0, 81.0, 45.9; HRMS (ESI): m/z calculated for $C_{14}H_{11}FN_5$ ($M^+H^+$) 268.0993 found 268.0988.

9-(4-ethynylbenzyl)-9H-purine-2,6-diamine B9

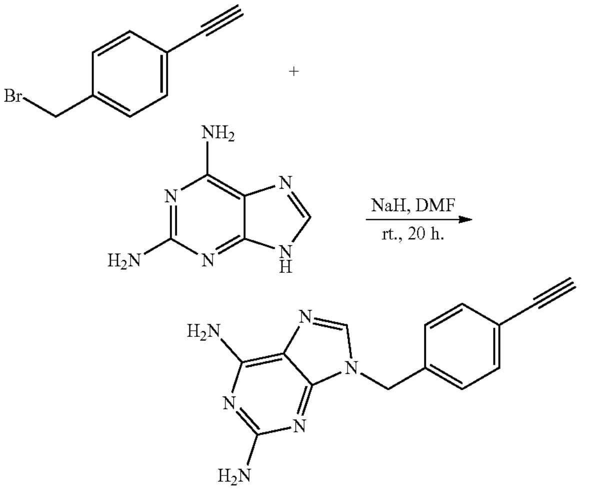

In a small, dry microwave vial, 2,6-diamino-9H-purine (150 mg, 0.999 mmol) was suspended in anhydrous DMF (4.5 mL) before addition of NaH (60% in paraffin oil, 43 mg, 1.08 mmol). The vial was purged with argon and the suspension stirred for 30 min. before compound B3 (211 mg, 1.08 mmol) was added. The mixture was stirred for additional 15 hours before the solvent was removed in vacuo. The residue was re-dissolved in MeOH and evaporated onto Celite 545 and purified by Flash Chromatography (MeOH: DCM, 4-10%) to yield 201 mg (76%, 0.201 mmol) of B9; $^1$H NMR (400 MHz, DMSO) δ 7.79 (s, 1H), 7.44 (d, J=8.3 Hz, 2H), 7.23-7.18 (m, 2H), 6.71 (s, 2H), 5.81 (s, 2H), 5.21 (s, 2H), 4.17 (s, 1H); $^{13}$C NMR (DMSO, 101 MHz) δ 160.4, 156.1, 151.7, 138.4, 137.3, 131.8, 127.2, 120.7, 113.0, 83.1, 80.8, 45.1; HRMS (ESI): m/z calculated for $C_{14}H_{13}N_6$ ($M^+H^+$) 265.1196 found 265.1137.

(5-((trimethylsilyl)ethynyl)pyridin-2-yl)methanol B10

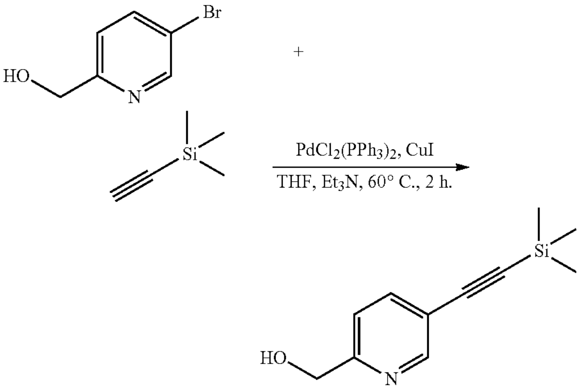

To a large, dry microwave vial, (5-bromopyridin-2-yl) methanol (2.00 g, 10.64 mmol), copper(I) iodide (40.5 mg, 0.213 mmol), bis(triphenylphosphine)-palladium-dichloride (149 mg, 0.213 mmol) were added. The vial was vac-filled with argon (3×) before anhydrous $Et_3N$ (5.9 mL, 42.6 mmol), THF (13.3 mL) and trimethylsilyl acetylene (1.82 mL, 12.8 mmol) was added under the exclusion of oxygen. The vial was sealed and the mixture was stirred at 60° C. for 2 h. before being cooled to room temperature. The reaction mixture was diluted with EtOAc (50 mL) and washed with sat. $NH_4Cl$ (50 mL), 2 M HCl (50 mL) and $H_2O$ (50 mL). The organic layer was dried over $MgSO_4$ and evaporated in vacuo. The resulting residue was purified by Flash Chromatography (MeOH:DCM, 2%) to yield 2.18 g of B10 (100%, 10.64 mmol); $^1$H NMR (400 MHz, $CDCl_3$) δ 8.64 (s, 1H), 7.75 (d, J=7.9 Hz, 1H), 7.27 (s, 1H), 4.77 (s, 2H), 3.83 (s, 1H), 0.27 (s, 9H); $^{13}$C NMR ($CDCl_3$, 101 MHz) δ 148.8, 142.4, 136.1, 135.0, 127.4, 103.8, 95.2, 62.7, 0.0; EI MS not recorded.

(5-ethynylpyridin-2-yl)methanol B11

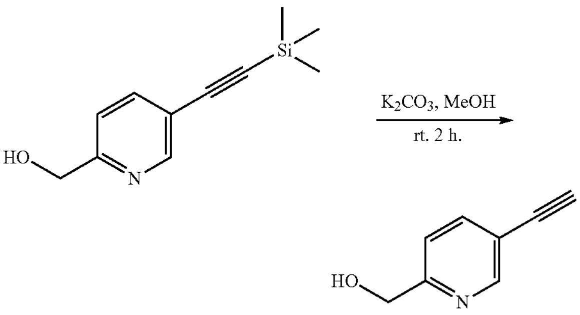

General Procedure 1 was applied with the trimethylsilyl acetylene B10 (2.18 g, 10.64 mmol) dissolved in MeOH (53 mL) after which $K_2CO_3$ was added (1.47 g, 10.64 mmol). The suspension was stirred for 2 h. at rt. before it was concentrated in vacuo. The resulting residue was purified by Flash Chromatography (MeOH:DCM, 5%) to afford 1.10 g of B11 (78%, 8.30 mmol); $^1H$ NMR (400 MHz, $CDCl_3$) δ 8.71-8.62 (m, 1H), 7.78 (dd, J=8.1, 2.1 Hz, 1H), 7.25 (dd, J=8.1, 0.8 Hz, 1H), 4.77 (d, J=4.7 Hz, 2H), 3.62 (t, J=5.1 Hz, 1H), 3.21 (s, 1H); $^{13}C$ NMR ($CDCl_3$, 101 MHz) δ 159.0, 151.7, 139.8, 119.8, 117.9, 80.3, 80.3, 64.2; EI MS not recorded.

(5-ethynylpyridin-2-yl)methyl 4-methylbenzenesulfonate B12

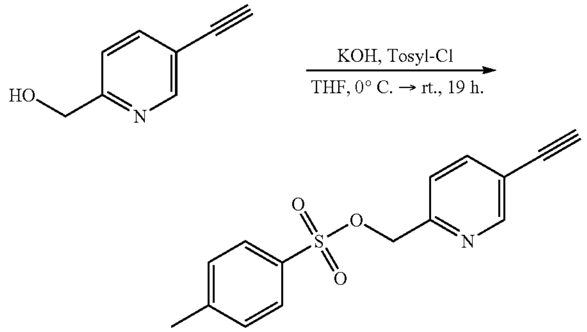

A solution of (5-ethynylpyridin-2-yl)methanol B11 (500 mg, 3.76 mmol) in THF (18.8 mL) was vigorously stirred at 0° C., before powdered potassium hydroxide (316 mg, 5.63 mmol) was added. The suspension was stirred for 15 min. before p-toluenesulfonyl chloride (930 mg, 4.88 mmol) was added. Cooling was removed, and the reaction mixture was stirred at rt. for 19 hours. The reaction mixture was quenched with saturated $NaHCO_3$ and the product was extracted with ethyl acetate (3×10 mL). The combined organics were dried over MgSO4 and concentrated in vacuo. The residue was purified by Flash Chromatography (DCM) to afford 990 mg of B12 (92%, 3.45 mmol); $^1H$ NMR (400 MHz, $CDCl_3$) δ 8.62-8.57 (m, 1H), 7.86-7.79 (m, 2H), 7.77 (dd, J=8.1, 2.1 Hz, 1H), 7.39 (d, J=8.1 Hz, 1H), 7.34 (d, J=8.0 Hz, 2H), 5.14 (s, 2H), 3.22 (s, 1H), 2.45 (s, 3H); $^{13}C$ NMR ($CDCl_3$, 101 MHz) δ 153.5, 152.2, 145.2, 139.9, 132.8, 130.0, 128.1, 121.1, 119.0, 81.1, 79.9, 71.3, 21.6; HRMS (ESI): m/z calculated for $C_{15}H_{13}NNaO_3S$ ($M^+Na^+$) 310.0508 found 310.0503.

9-((5-ethynylpyridin-2-yl)methyl)-9H-purin-6-amine B13

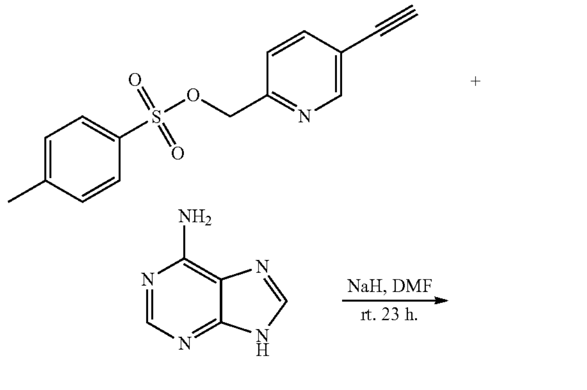

-continued

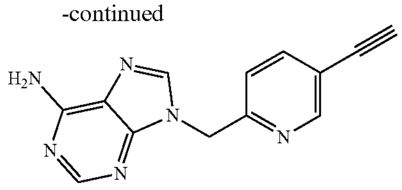

In a small, dry microwave vial, adenine (100 mg, 0.740 mmol) was suspended in anhydrous DMF (4.35 mL) before addition of NaH (50-60% in paraffin oil, 35 mg, 0.799 mmol). The vial was purged with argon and the suspension was stirred for 30 min. before B12 (230 mg, 0.799 mmol) in DMF (1.07 mL) was added. The mixture was stirred for additional 23 h. before the solvent was removed in vacuo. The residue was re-dissolved in MeOH and evaporated onto Celite 545 and purified by Flash Chromatography (MeOH:DCM, 10%) to yield 88 mg of B13 (48%, 0.352 mmol); $^1H$ NMR (400 MHz, DMSO) δ 8.59 (dd, J=2.1, 0.9 Hz, 1H), 8.23 (s, 1H), 8.09 (s, 1H), 7.89 (dd, J=8.1, 2.2 Hz, 1H), 7.35-7.19 (m, 3H), 5.51 (s, 2H), 4.43 (s, 1H); $^{13}C$ NMR (DMSO, 101 MHz) δ 155.9, 155.7, 152.5, 151.6, 149.5, 141.3, 139.8, 121.2, 118.5, 117.6, 84.1, 80.1, 47.4; HRMS (ESI): m/z calculated for $C_{13}H_{11}N_6$ ($M^+H^+$) 251.1040 found 251.1042.

4-((trimethylsilyl)ethynyl)-2-methoxy-benzylalcohol B14

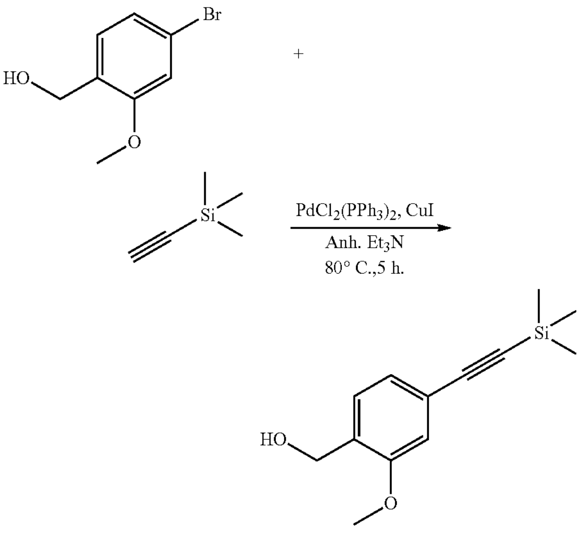

To a large, dry microwave vial, (4-bromo-2-methoxyphenyl)methanol (2.00 g, 9.21 mmol), copper(I) iodide (94 mg, 0.737 mmol), tetrakis(triphenylphosphine)palladium(0) (426 mg, 0.369 mmol) were added. The vial was vac-filled with argon (3×) before anhydrous $Et_3N$ (18 mL) and trimethylsilyl acetylene (2.62 mL, 18.43 mmol) were added under the exclusion of oxygen. The vial was sealed and the mixture stirred at 80° C. for 5 h. before being cooled to room temperature. The reaction mixture was diluted with DCM (50 mL) and washed with sat. $NH_4Cl$ (20 mL), 2 M HCl (20 mL) and $H_2O$ (20 mL). The organic layers was dried over $MgSO_4$ and evaporated in vacuo. The residue was purified by Flash Chromatography (MeOH:DCM, 0-5%) to yield 1.95 g of B14 (90%, 8.32 mmol); $^1H$ NMR (400 MHz, $CDCl_3$) δ 7.21 (d, J=7.6 Hz, 1H), 7.07 (dd, J=7.6, 1.4 Hz, 1H), 6.96 (d, J=1.4 Hz, 1H), 4.66 (d, J=6.5 Hz, 2H), 3.86 (s, 3H), 2.26-2.19 (m, 1H), 0.26 (s, 9H); $^{13}C$ NMR ($CDCl_3$, 101 MHz) δ 157.0, 130.0, 128.4, 124.7, 123.5, 113.5, 105.0, 94.1, 61.8, 55.4; HRMS (ESI) not recorded.

4-ethynyl-2-methoxy-benzylalcohol B15

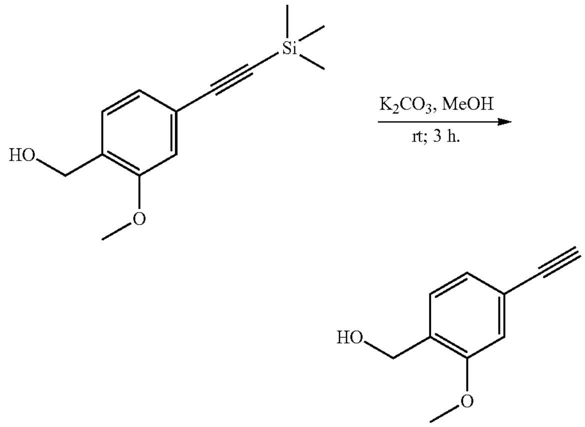

General Procedure 1 was applied with the trimethylsilyl acetylene B14 (2.01 g, 8.26 mmol) dissolved in MeOH (41 mL) after which $K_2CO_3$ was added (1.14 g, 8.23 mmol). The suspension was stirred for 3 h. at rt. before it was concentrated in vacuo. The resulting residue was purified by Flash Chromatography (MeOH:DCM, 5%) to afford 1.08 g of B15 (81%, 6.66 mmol; $^1H$ NMR (400 MHz, $CDCl_3$) δ 7.24 (d, J=7.6 Hz, 1H), 7.11 (dd, J=7.6, 1.4 Hz, 1H), 6.99 (d, J=1.4 Hz, 1H), 4.67 (d, J=6.5 Hz, 2H), 3.86 (s, 3H), 3.08 (s, 1H), 2.23 (t, J=6.5 Hz, 1H); $^{13}C$ NMR ($CDCl_3$, 101 MHz) δ 157.0, 130.3, 128.5, 124.8, 122.4, 113.7, 83.6, 77.1, 61.6, 55.4; EI MS: m/z calculated for $C_{10}H_{10}O_2$ ($M^+$) 162.2 found 162.1

9-(4-ethynyl-2-methoxybenzyl)-9H-purin-6-amine B16

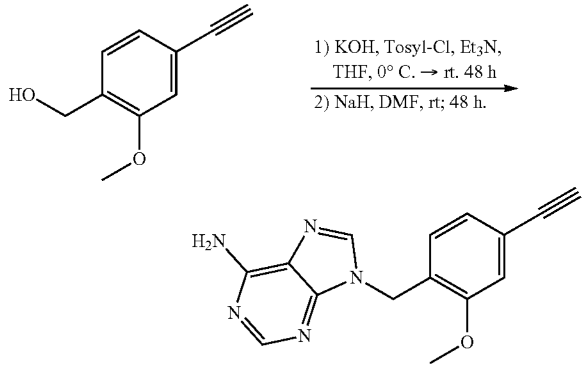

A solution of B15 (500 mg, 3.08 mmol) in THF (15.4 mL) was vigorously stirred at 0° C., before powdered potassium hydroxide (305 mg, 4.62 mmol) and anhydrous $Et_3N$ (0.7 mL, 5.00 mmol) was added. The suspension was stirred for 15 min. before p-toluenesulfonyl chloride (764 mg, 4.01 mmol) was added. Cooling was removed, and the reaction mixture was stirred at rt. for 48 hours before the solvent was removed. The residue was transferred to a large microwave vial, after which adenine (233 mg, 1.72 mmol), anhydrous DMF (4.35 mL) and NaH (50-60% in paraffin oil, 75 mg, 1.72 mmol) was added. The vial was purged with argon and the mixture was stirred for 48 h. before the solvent was removed in vacuo. The residue was re-dissolved in MeOH and evaporated onto Celite 545 and purified by Flash Chromatography (MeOH:DCM, 7%) to yield 84 mg of B16 (10%, 0.301 mmol); $^1H$ NMR (400 MHz, DMSO) δ 8.12 (d, J=3.2 Hz, 2H), 7.24 (s, 2H), 7.12 (d, J=1.5 Hz, 1H), 7.01 (dd, J=7.7, 1.5 Hz, 1H), 6.89 (d, J=7.8 Hz, 1H), 5.31 (s, 2H), 4.21 (s, 1H), 3.87 (s, 3H); $^{13}C$ NMR (DMSO, 101 MHz) δ 156.4, 155.9, 152.5, 149.5, 141.0, 128.6, 125.7, 124.0, 122.4, 118.5, 113.8, 83.2, 80.8, 55.7, 41.5; HRMS (ESI): m/z calculated for $C_{15}H_{14}N_5O$ ($M^+H^+$) 280.1193 found 280.1186.

2-((6-amino-9H-purin-9-yl)methyl)-5-ethynylphenol B17

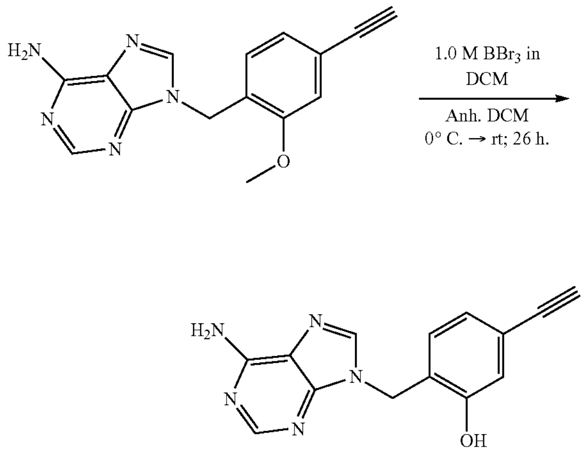

The anisole B16 (55 mg, 0.197 mmol) was dissolved in anhydrous dichloromethane (1.19 ml) and cooled to 0° C. before a solution of boron tribromide ($BBr_3$, 1.0 M in $CH_2Cl_2$, 0.59 mL, 0.59 mmol) was added. The mixture was allowed to reach rt. after which it was stirred for 26 h. The reaction was cooled to 0° C. again and quenched with the slow addition of $Et_2O$ (2 mL) and MeOH (2 mL). The mixture was diluted with water (5 mL), acidified with aqueous HCl, and extracted with EtOAc (5×8 mL). The combined organic layers were dried over $MgSO_4$ and evaporated in vacuo to yield 15 mg of crude B17 (32%, 0.057 mmol); $^1H$ NMR (400 MHz, DMSO) δ 10.24 (s, 1H), 8.14-8.11 (m, 2H), 7.25 (s, 2H), 6.93 (d, J=1.5 Hz, 1H), 6.89 (s, 1H), 6.86 (dd, J=7.8, 1.5 Hz, 1H), 5.28 (s, 2H), 4.12 (s, 1H); $^{13}C$ NMR (DMSO, 101 MHz) δ 155.8, 154.8, 152.3, 149.4, 141.0, 129.2, 124.3, 122.6, 122.0, 117.9, 83.1, 80.3, 41.6, 40.1; HRMS (ESI): m/z calculated for $C_{14}H_{12}N_5O$ ($M^+H^+$) 266.1036 found 266.1041.

6-chloro-9-((5-ethynylpyridin-2-yl)methyl)-9H-purine B18

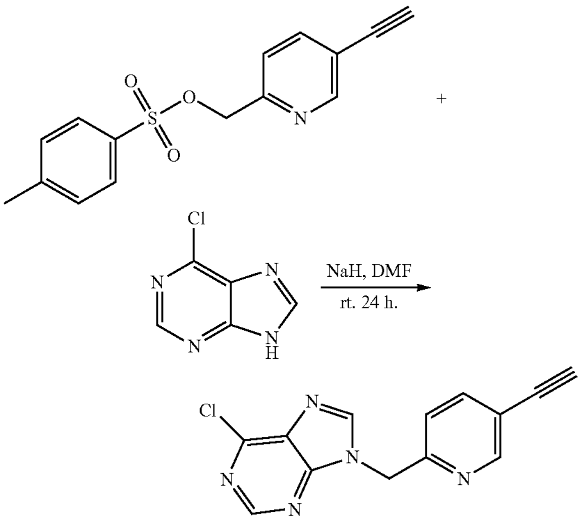

In a small, dry microwave vial, 6-chloro-9H-purine (100 mg, 0.647 mmol) was suspended in anhydrous DMF (1.4 mL) before addition of NaH (50-60% in paraffin oil, 31 mg, 0.699 mmol). The vial was purged with argon and the suspension was stirred for 30 min. before B11 (201 mg, 0.699 mmol) in DMF (0.70 mL) was added. The mixture was stirred for additional 24 h. before the solvent was removed in vacuo. The residue was re-dissolved in MeOH and evaporated onto Celite 545 and purified by Flash Chromatography (MeOH:DCM, 2%) to yield 96 mg of B18 (55%, 0.356 mmol); $^1$H NMR (400 MHz, $CDCl_3$) δ 8.75 (s, 1H), 8.64 (dd, J=2.1, 0.9 Hz, 1H), 8.35 (s, 1H), 7.77 (dd, J=8.0, 2.1 Hz, 1H), 7.32 (dd, J=8.0, 0.9 Hz, 1H), 5.57 (s, 2H), 3.24 (s, 1H); $^{13}$C NMR ($CDCl_3$, 101 MHz) δ 153.3, 153.0, 152.2, 151.9, 151.2, 145.7, 140.3, 131.5, 121.7, 119.3, 81.6, 79.6, 48.8; HRMS (ESI): m/z calculated for $C_{13}H_9ClN_5$ ($M^+H^+$) 270.0541 found 270.0547.

tert-butyl 4-(9-((5-ethynylpyridin-2-yl)methyl)-9H-purin-6-yl)piperazine-1-carboxylate B19

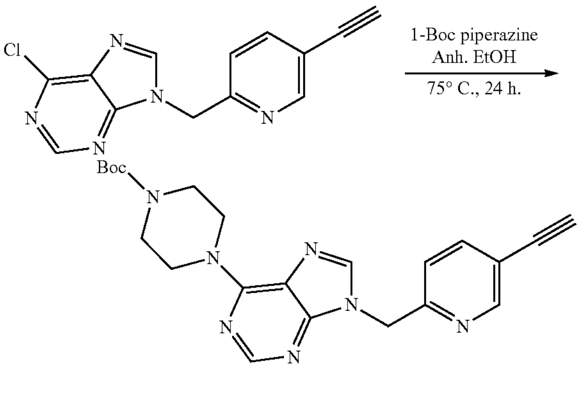

In a small, dry microwave vial, the chloro-purine B18 (45 mg, 0.167 mmol) was suspended in anhydrous ethanol (1.9 mL) after which 1-Boc-piperazine (124 mg, 0.667 mmol) was added. The vial was sealed and the mixture was stirred at 75° C. for 24 h. The reaction mixture was concentrated and the residue was purified by Flash Chromatography (MeOH:DCM, 1-2%) to yield 65 mg of B19 (93%, 0.155 mmol); $^1$H NMR (400 MHz, $CDCl_3$) δ 8.66 (dd, J=2.1, 0.9 Hz, 1H), 8.36 (s, 1H), 7.92 (s, 1H), 7.72 (dd, J=8.1, 2.1 Hz, 1H), 7.19 (dd, J=8.1, 0.9 Hz, 1H), 5.48 (s, 2H), 4.29 (s, 4H), 3.63-3.50 (m, 4H), 3.21 (s, 1H), 1.49 (s, 9H); $^{13}$C NMR ($CDCl_3$, 101 MHz) δ 154.8, 154.8, 154.0, 152.7, 152.7, 151.1, 140.2, 138.9, 121.4, 119.8, 118.8, 81.1, 80.1, 79.9, 48.3, 45.0, 28.4; HRMS (ESI): m/z calculated for $C_{22}H_{25}N_7NaO_2$ ($M^+Na^+$) 442.1962 found 442.1967.

9-((5-ethynylpyridin-2-yl)methyl)-6-(piperazin-1-yl)-9H-purine B20

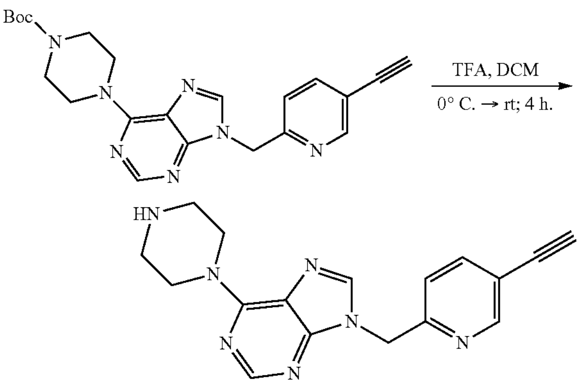

The Boc-protected piperazine B19 (64 mg, 0.153 mmol) was dissolved in anhydrous DCM (0.76 mL) before trifluoroacetic acid (0.14 mL, 1.83 mmol) was added at 0° C., and the mixture was stirred at rt. for 24 h. The reaction mixture was concentrated in vacuo, and the residue resuspended in EtOAc (10 mL) and 10% NaOH (5 mL). After separation, the aqueous layer was reextracted with EtOAc (3×5 mL), before the combined organic layers were washed with brine (5 mL), dried over $Na_2SO_4$ and evaporated in vacuo. which yielded 49 mg of B20 (100%, 0.153 mmol); $^1$H NMR (400 MHz, DMSO) δ 8.58 (dd, J=2.2, 0.9 Hz, 1H), 8.27 (s, 1H), 8.17 (s, 1H), 7.89 (dd, J=8.1, 2.2 Hz, 1H), 7.27 (dd, J=8.2, 0.9 Hz, 1H), 5.53 (s, 2H), 4.43 (s, 1H), 4.16 (s, 4H), 3.53 (s, 2H), 2.81 (t, J=5.1 Hz, 4H); $^{13}$C NMR (DMSO, 101 MHz) δ 155.6, 153.1, 151.8, 151.6, 150.6, 140.3, 139.8, 121.2, 118.7, 117.6, 84.1, 80.1, 47.4, 45.6; HRMS (ESI): m/z calculated for $C_{17}H_{18}N_7$ ($M^+H^+$) 320.1618 found 320.1630.

tert-butyl 4-(9-(4-ethynylbenzyl)-9H-purin-6-yl)piperazine-1-carboxylate B21

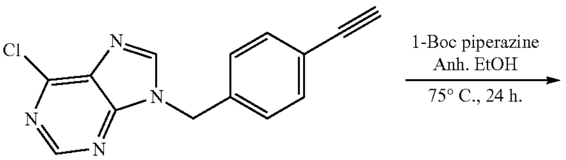

-continued

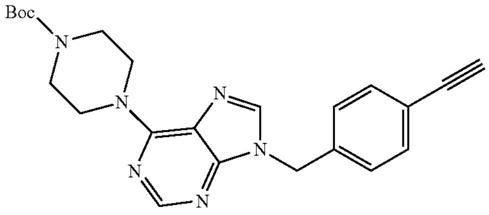

In a small dry microwave vial, the chloro-purine B6 (60 mg, 0.223 mmol) was suspended in anhydrous ethanol (2.48 mL) after which 1-Boc-piperazine (166 mg, 0.893 mmol) was added. The vial was sealed and the mixture was stirred at 75° C. for 24 h. The reaction mixture was concentrated and the residue was purified by Flash Chromatography (MeOH:DCM, 1-2%) to yield 80 mg of B21 (86%, 0.191 mmol); $^1$H NMR (400 MHz, $CDCl_3$) δ 8.38 (s, 1H), 7.72 (s, 1H), 7.46 (d, J=8.3 Hz, 2H), 7.21 (d, J=8.3 Hz, 2H), 5.37 (s, 2H), 4.29 (s, 4H), 3.61-3.52 (m, 4H), 3.08 (s, 1H), 1.49 (s, 9H); $^{13}$C NMR ($CDCl_3$, 101 MHz) δ 154.8, 154.0, 152.7, 151.1, 138.3, 136.4, 132.7, 127.6, 122.3, 119.9, 82.9, 80.1, 77.9, 46.7, 45.0, 28.4; HRMS (ESI): m/z calculated for $C_{23}H_{27}N_6O_2$ ($M^+H^+$) 419.2190 found 419.2201.

9-(4-ethynylbenzyl)-6-(piperazin-1-yl)-9H-purine B22

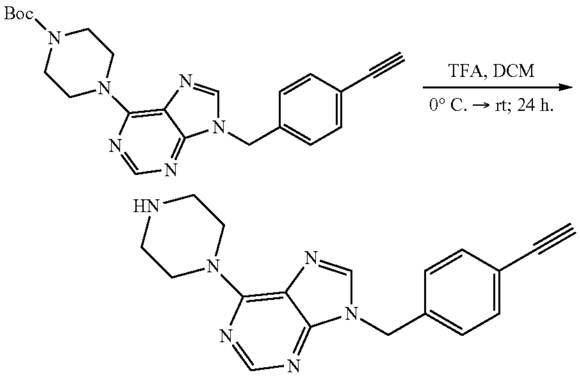

The Boc-protected piperazine B21 (80 mg, 0.191 mmol) was dissolved in anhydrous DCM (0.96 mL) before trifluoroacetic acid (0.19 mL, 2.50 mmol) was added at 0° C., and the mixture was stirred at rt. for 4 h. The reaction mixture was concentrated in vacuo, and the residue resuspended in EtOAc (10 mL) and 10% NaOH (5 mL). After separation, the aqueous layer was reextracted with EtOAc (3x5 mL), before the combined organic layers were washed with brine (5 mL), dried over $Na_2SO_4$ and evaporated in vacuo which yielded 42 mg of B22; $^1$H NMR (400 MHz, DMSO) δ 8.31 (s, 1H), 8.23 (s, 1H), 7.45 (d, J=8.3 Hz, 2H), 7.32-7.26 (d, J=8.3 Hz, 2H), 5.41 (s, 2H), 4.19 (m, 5H), 3.42 (s, 2H), 2.82 (t, J=5.1 Hz, 4H); $^{13}$C NMR (DMSO, 101 MHz) δ 153.1, 151.9, 150.4, 139.7, 137.8, 131.9, 127.6, 121.0, 118.8, 83.0, 80.9, 45.8, 45.5, 26.6; HRMS (ESI): m/z calculated for $C_{18}H_{19}N_6$ ($M^+H^+$) 319.1666 found 319.1682.

(R)-1-(4-((trimethylsilyl)ethynyl)phenyl)ethan-1-ol B23

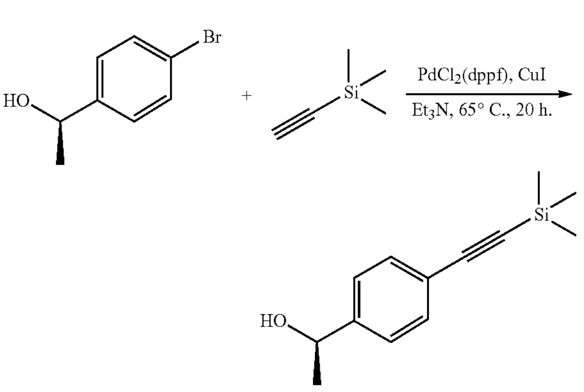

To a large, dry microwave vial, (R)-1-(4-bromophenyl) ethan-1-ol (950 mg, 4.72 mmol), copper(I) iodide (18 mg, 0.095 mmol), [1,1'-Bis(diphenylphosphino)ferrocene]palladium(II) dichloride (138 mg, 0.189 mmol) were added. The vial was vac-filled with argon (3×) before anhydrous $Et_3N$ (16 mL) and trimethylsilyl acetylene (0.81 mL, 5.7 mmol) were added under the exclusion of oxygen. The vial was sealed and the mixture stirred at 65° C. for 20 h. before being cooled to room temperature. The reaction mixture was diluted with $Et_2O$ (50 mL) and washed with sat. $NH_4Cl$ (20 mL), 2 M HCl (20 mL) and $H_2O$ (20 mL). The organic layer was dried over $MgSO_4$ and evaporated in vacuo. The residue was purified by Flash Chromatography (EtOAc:PE, 0-35%) to yield 1.03 g of B23 (100%, 4.72 mmol); $^1$H NMR (400 MHz, $CDCl_3$) δ 7.45 (d, J=8.3 Hz, 2H), 7.30 (d, J=8.2 Hz, 2H), 4.89 (qd, J=6.4, 3.5 Hz, 1H), 1.83 (d, J=3.6 Hz, 1H), 1.47 (d, J=6.5 Hz, 3H), 0.25 (s, 9H); $^{13}$C NMR ($CDCl_3$, 101 MHz) δ 146.2, 132.1, 125.2, 122.2, 105.0, 94.1, 70.1, 25.2, 0.0; HRMS (ESI): m/z calculated for $C_{13}H_{18}NaOSi$ ($M^+Na^+$) 241.1019 found 241.1020.

(R)-1-(4-ethynylphenyl)ethan-1-ol B24

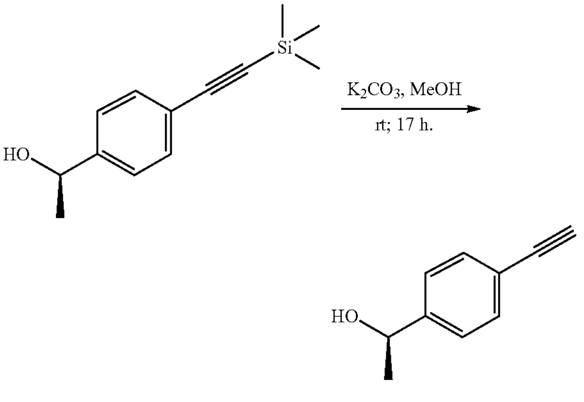

General Procedure 1 was applied with the trimethylsilyl acetylene B23 (1.03 g, 4.72 mmol) dissolved in MeOH (41 mL) after which $K_2CO_3$ was added (651 mg, 4.72 mmol). The suspension was stirred for 17 h. at rt. before it was concentrated in vacuo. The resulting residue was purified by Flash Chromatography (MeOH:DCM, 0-2%) to afford 620 mg of B24 (90%, 4.24 mmol; $^1$H NMR (400 MHz, $CDCl_3$) δ 7.48 (d, J=8.3 Hz, 2H), 7.33 (d, J=8.1 Hz, 2H), 4.90 (qd, J=6.5, 3.2 Hz, 1H), 3.06 (s, 1H), 1.84 (d, J=3.3 Hz, 1H), 1.48 (d, J=6.5 Hz, 3H); $^{13}C$ NMR ($CDCl_3$, 101 MHz) δ 146.5, 132.3, 125.3, 121.2, 83.5, 77.0, 70.1, 25.2; EI MS not recorded.

(S)-1-(1-bromoethyl)-4-ethynylbenzene B25

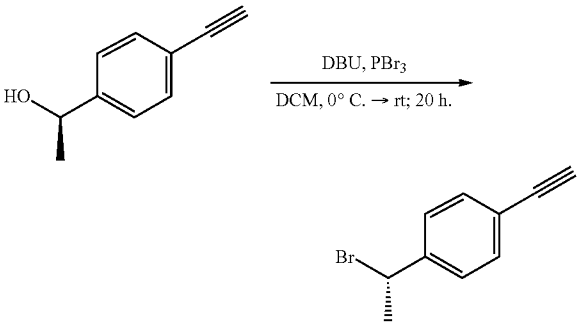

The benzyl alcohol B24 (268 mg, 1.83 mmol) and 1,8-Diazabicyclo(5.4.0)undec-7-ene (DBU, 0.356 ml, 2.38 mmol) was dissolved in anhydrous dichloromethane (1.83 mL). The vessel was purged with argon and cooled to 0° C. before phosphorous tribromide (0.19 mL, 2.0 mmol) was added dropwise. The mixture was stirred for 20 h. during which it reached rt. The reaction mixture was quenched with ice water (30 mL) before extraction with dichloromethane (3×30 mL). The combined organic layers were washed with 5% $H_2SO_4$ (2×30 mL), sat. $NaHCO_3$ (2×30 mL) and brine (2×30 mL) before being dried over $MgSO_4$. Evaporation in vacuo yielded 275 mg of B25 (72%, 1.32 mmol). No further purification necessary; $^1H$ NMR (400 MHz, $CDCl_3$) δ 7.47 (d, J=8.4 Hz, 2H), 7.39 (d, J=8.4 Hz, 2H), 5.18 (q, J=6.9 Hz, 1H), 3.09 (s, 1H), 2.03 (d, J=6.9 Hz, 3H); $^{13}C$ NMR ($CDCl_3$, 101 MHz) δ 143.8, 132.4, 126.8, 122.1, 83.2, 77.8, 48.5, 26.6; HRMS (ESI): m/z calculated for $C_{10}H_9Br$ ($M^+$) 207.9888 mass not found.

(R)-9-(1-(4-ethynylphenyl)ethyl)-9H-purin-6-amine B26

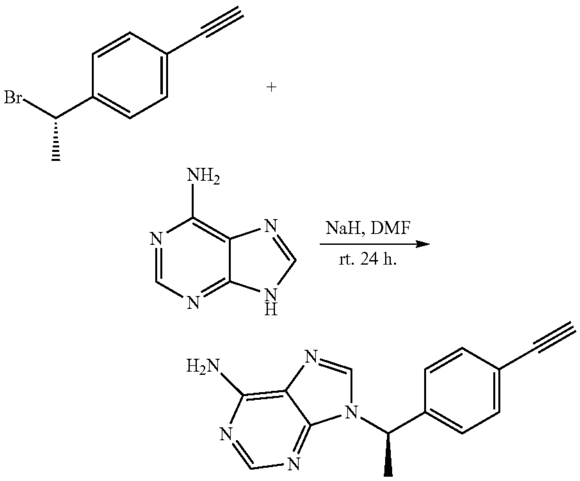

In a large, dry microwave vial, adenine (168 mg, 1.24 mmol) was suspended in anhydrous DMF (7.21 mL) before addition of NaH (50-60% in paraffin oil, 60 mg, 1.37 mmol). The vial was purged with argon and the suspension was stirred for 30 min. before B25 (130 mg, 0.622 mmol) in DMF (0.83 mL) was added. The mixture was stirred for additional 24 h. before the solvent was removed in vacuo. The residue was re-dissolved in MeOH and evaporated onto Celite 545 and purified by Flash Chromatography (MeOH: DCM, 0-3.5%) to yield 42 mg of B26 (26%, 0.352 mmol); $^1H$ NMR (400 MHz, DMSO) δ 8.40 (s, 1H), 8.10 (s, 1H), 7.45 (d, J=8.3 Hz, 2H), 7.34 (d, J=8.2 Hz, 2H), 7.25 (s, 2H), 5.84 (q, J=7.2 Hz, 1H), 4.18 (s, 1H), 1.94 (d, J=7.2 Hz, 3H); $^{13}C$ NMR (DMSO, 101 MHz) δ 155.9, 152.3, 149.2, 142.4, 139.0, 131.9, 126.5, 120.9, 118.9, 83.0, 80.9, 52.8, 20.2; HRMS (ESI): m/z calculated for $C_{15}H_{14}N_5$ ($M^+H^+$) 264.1244 found 264.1252.

Tert-butyl (R)-4-(9-(1-(4-ethynylphenyl)ethyl)-9H-purin-6-yl)piperazine-1-carboxylate B27

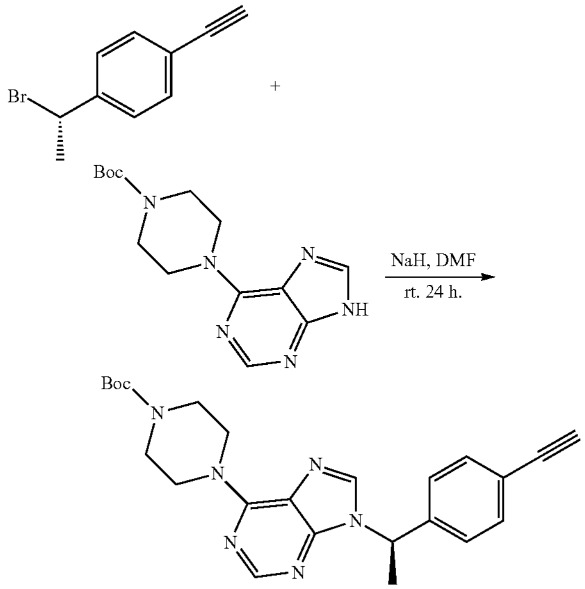

In a large, dry microwave vial, tert-butyl 4-(9H-purin-6-yl)piperazine-1-carboxylate (393 mg, 1.29 mmol) was suspended in anhydrous DMF (7.60 mL) before addition of NaH (50-60% in paraffin oil, 62 mg, 1.37 mmol). The vial was purged with argon and the suspension was stirred for 30 min. before B25 (135 mg, 0.646 mmol) in DMF (0.86 mL) was added. The mixture was stirred for additional 5 h. before the solvent was removed in vacuo. The residue was re-dissolved in MeOH and evaporated onto Celite 545 and purified by Flash Chromatography (MeOH:DCM, 0-3.5%) to yield 138 mg of B27 (49%, 0.319 mmol); $^1H$ NMR (400 MHz, $CDCl_3$) δ 8.35 (s, 1H), 7.75 (s, 1H), 7.50-7.42 (m, 2H), 7.26-7.23 (m, 2H), 5.93 (d, J=7.2 Hz, 1H), 4.28 (s, 4H), 3.67-3.49 (m, 4H), 3.08 (s, 1H), 1.95 (d, J=7.2 Hz, 3H), 1.49 (s, 9H); $^{13}C$ NMR ($CDCl_3$, 101 MHz) δ 154.8, 153.9, 152.5, 150.9, 140.9, 136.4, 132.7, 126.4, 122.1, 120.2, 82.9, 80.1, 77.9, 52.9, 28.4, 20.7; HRMS (ESI): m/z calculated for $C_{24}H_{29}N_6O_2$ ($M^+H^+$) 433.2347 found 433.2359.

(R)-9-(1-(4-ethynylphenyl)ethyl)-6-(piperazin-1-yl)-9H-purine B28

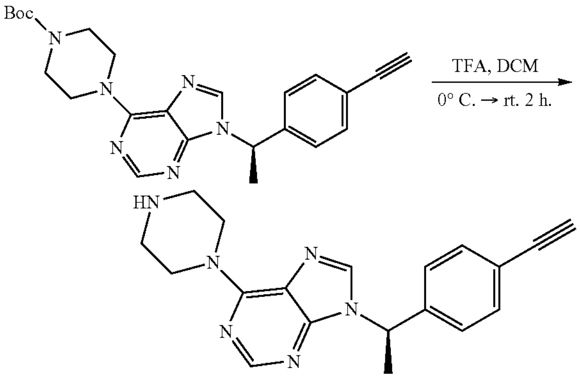

The Boc-protected piperazine B27 (115 mg, 0.266 mmol) was dissolved in anhydrous DCM (1.52 mL) before trifluoroacetic acid (0.27 mL, 3.5 mmol) was added at 0° C., and the mixture was stirred at rt. for 2 h. The reaction mixture was concentrated in vacuo, and the residue resuspended in EtOAc (10 mL) and 10% NaOH (5 mL). After separation, the aqueous layer was reextracted with EtOAc (3x5 mL), before the combined organic layers were washed with brine (5 mL), dried over $Na_2SO_4$ and evaporated in vacuo which yielded 85 mg of B28 (96%, 0.256 mmol); $^1$H NMR (400 MHz, DMSO) δ 8.43 (s, 1H), 8.18 (s, 1H), 7.49-7.38 (m, 2H), 7.37-7.26 (m, 2H), 5.87 (q, J=7.2 Hz, 1H), 4.18 (m, 5H), 3.34 (s, 3H), 2.84-2.72 (m, 4H), 1.93 (d, J=7.3 Hz, 3H); $^{13}$C NMR (DMSO, 101 MHz) δ 153.1, 151.7, 150.2, 142.2, 137.9, 131.9, 126.5, 120.9, 119.1, 83.0, 80.9, 57.6, 52.7, 45.7, 20.1; HRMS (ESI): m/z calculated for $C_{24}H_{29}N_6O_2$ ($M^+H^+$) 333.1822 found 333.1825.

N-(3-ethynylphenyl)benzamide B29

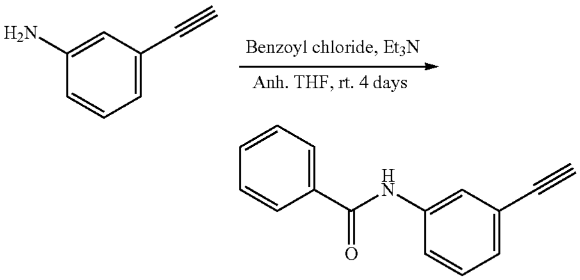

3-Ethynylaniline (0.20 mL, 1.89 mmol) was dissolved in anhydrous THF (20 mL) and placed under a nitrogen atmosphere. Benzoyl chloride (0.23 mL, 1.98 mmol) and $Et_3N$ (1.15 mL, 8.25 mmol) was added to the solution. The reaction mixture was stirred at room temperature for a period of 4 days upon which it was diluted with EtOAc (50 mL) and washed with saturated $NH_4Cl$ (2x30 mL) and brine (2x30 mL). The organic phase was dried with $MgSO_4$ and concentrated in vacuo. The residue was purified by Flash Chromatography (EtOAc:PE, 20-40%) to yield 420.0 mg of B29 (100%); $^1$H NMR (400 MHz, $CDCl_3$): δ 7.94 (s, 1H), 7.87-7.82 (m, 2H), 7.76 (t, J=1.8 Hz, 1H), 7.71-7.66 (m, 1H), 7.58-7.51 (m, 1H), 7.50-7.43 (m, 2H), 7.34-7.24 (m, 2H), 3.08 (s, 1H); $^{13}$C NMR (101 MHz, $CDCl_3$): δ 165.8, 138.0, 134.7, 132.0, 129.1, 128.8, 128.3, 127.1, 123.7, 123.0, 120.8, 83.1, 77.6; HRMS (ESI): m/z calculated for $C_{15}H_{12}NO$ ($M^+H^+$) 222.0913 found 222.0900.

N-(3-ethynylphenyl)-4-methoxybenzamide B30

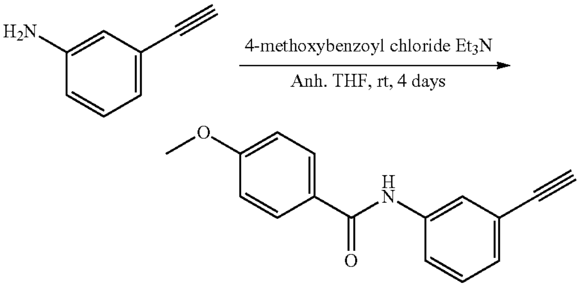

3-Ethynylaniline (0.20 mL, 1.90 mmol) was dissolved in anhydrous THF (20 mL) and placed under a nitrogen atmosphere. 4-methoxybenzoylchloride (420 mg, 2.49 mmol) and $Et_3N$ (1.35 mL, 9.69 mmol) was added to the solution. The reaction mixture was stirred at room temperature for a period of 4 days upon which it was diluted with EtOAc (50 mL) and washed with saturated $NH_4Cl$ (2x30 mL) and brine (2x30 mL). The organic phase was dried with $MgSO_4$ and concentrated in vacuo. The residue was purified by Flash Chromatography (EtOAc:PE, 0-30%) yield 152 mg of B30 (32%, 0.060 mmol); $^1$H NMR (400 MHz, $CDCl_3$): δ 7.91 (s, 1H), 7.85-7.79 (m, 2H), 7.75 (t, J=1.8 Hz, 1H), 7.68 (ddd, J=7.9, 2.3, 1.3 Hz, 1H), 7.34-7.22 (m, 2H), 6.94 (dd, J=8.4, 1.2 Hz, 2H), 3.86 (s, 3H), 3.07 (s, 1H); $^{13}$C NMR (101 MHz, $CDCl_3$): δ 165.3, 162.6, 138.2, 129.1, 129.0, 128.0, 126.9, 123.6, 122.9, 120.8, 114.0, 83.2, 77.5, 55.5; HRMS (ESI): m/z calculated for $C_{16}H_{14}NO_2$ ($M^+H^+$) 252.1019 found 252.1033.

6-(3-Ethynylphenoxy)-9H-purine B31

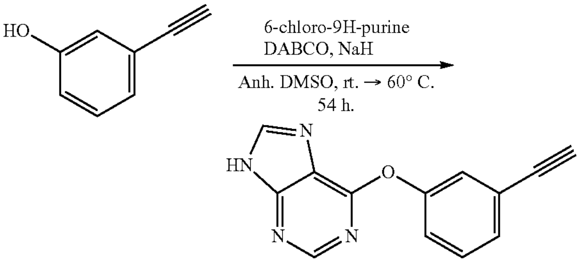

DABCO (1.06 g, 9.41 mmol) was added to a solution of 6-chloropurine (260 mg, 1.68 mmol) in anhydrous DMSO (4 mL) and stirred for 28 h. at rt. after which a solution of 3-ethynylphenol (0.26 mL, 2.38 mmol) and NaH (50-60% in paraffin oil, 50 mg, 1.15 mmol) in DMSO (4 mL) was slowly added. The combined mixtures were stirred at 60° C. for 26 h. Hereafter, water (10 mL) was slowly added and the mixture was extracted with EtOAc (6x20 mL). The combined organic phases were dried with $Na_2SO_4$ and concentrated in vacuo. The residue was purified by Flash Chromatography (MeOH:DCM, 2-5%) to yield 84 mg of B31 (21%, 0.353 mmol); $^1$H NMR (400 MHz, DMSO): δ 13.67 (s, 1H), 8.54 (s, 1H), 8.46 (s, 1H), 7.50 (t, J=7.8 Hz, 1H), 7.46-7.41 (m, 2H), 7.38 (ddd, J=8.0, 2.4, 1.2 Hz, 1H), 4.30 (s, 1H); $^{13}$C NMR (101 MHz, DMSO): δ 152.2, 151.1, 143.8, 130.1, 129.0, 125.0, 123.0, 122.9, 82.6, 81.6; HRMS (ESI): m/z calculated for $C_{13}H_9N_4O$ ($M^+H^+$) 237.0771 found 237.0762.

2-Amino-6-(3-ethynylphenoxy)-9H-purine B32

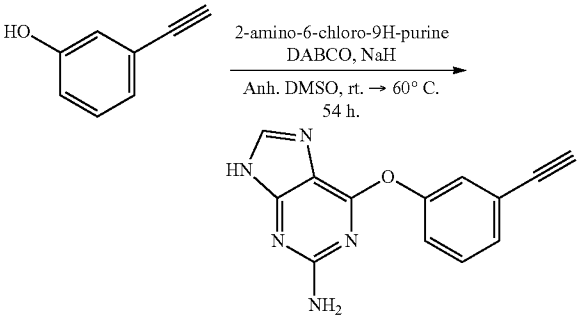

DABCO (0.96 g, 8.55 mmol) was added to a stirred solution of 2-amino-6-chloro-9H-purine (240 mg, 1.44 mmol) in anhydrous DMSO (3 mL). The reaction mixture was stirred for a period of 18 h. at rt. after which a solution of 3-ethynylphenol (0.22 mL, 2.01 mmol) and NaH (50-60% in paraffin oil, 40 mg, 0.920 mmol) in DMSO (3 mL) was slowly added. The combined mixtures were stirred at rt. for 20 h. followed by 24 h. at 60° C. Hereafter, water (10 mL) was slowly added and the mixture was extracted with EtOAc (6×20 mL). The combined organic phases were dried with $Na_2SO_4$ and concentrated in vacuo. The residue was purified by Flash Chromatography (MeOH:DCM, 0-8%) to yield 152.5 mg of B32 (42%, 0.605 mmol); $^1$H NMR (400 MHz, DMSO): δ 12.62 (s, 1H), 7.97 (s, 1H), 7.46 (t, J=8.0 Hz, 1H), 7.39-7.33 (m, 2H), 7.31 (ddd, J=8.1, 2.4, 1.2 Hz, 1H), 6.31 (s, 2H), 4.28 (s, 1H); $^{13}$C NMR (101 MHz, DMSO): δ 159.6, 152.5, 129.9, 128.4, 124.7, 122.8, 122.8, 82.6, 81.4; HRMS (ESI): m/z calculated for $C_{13}H_{10}N_5O$ ($M^+H^+$) 252.0880 found 252.0886.

6-amino-N6-(3-ethynylphenyl)-9H-purine B33

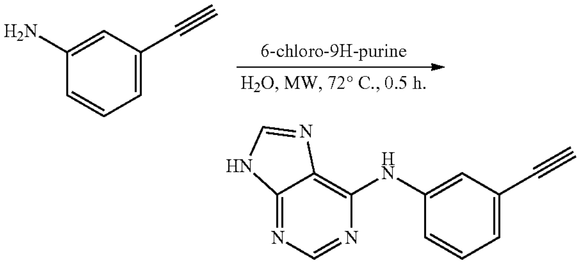

In a microwave vial, 3-ethynylanilin (0.44 mL, 6.4 mmol) was added to a suspension of 6-chloropurin (330 mg, 2.14 mmol) in water (12 mL). The vial was sealed and irradiated in a microwave reactor at 72° C. for 30 min. Upon cooling to rt., the product precipitated. The reaction mixture was filtered, and the precipitate washed with cold water, redissolved in MeOH and concentrated in vacuo. The residue was purified by Flash Chromatography (MeOH:DCM, 2-5%) to yield 378 mg of B33 (74%, 1.58 mmol); $^1$H NMR (400 MHz, DMSO): δ 13.19 (s, 1H), 9.92 (s, 1H), 8.44 (s, 1H), 8.33 (s, 1H), 8.23 (s, 1H), 7.99 (d, J=8.3 Hz, 1H), 7.35 (t, J=8.0 Hz, 1H), 7.14 (d, J=7.7 Hz, 1H), 4.18 (s, 1H); $^{13}$C NMR (101 MHz, DMSO): δ 151.7, 140.1, 128.7, 125.4, 123.0, 121.7, 120.9, 83.8, 80.2; HRMS (ESI): m/z calculated for $C_{13}H_{10}N_5$ ($M^+H^+$) 236.0931 found 236.0925.

2-bromo-4-cyanophenyl acetate B34

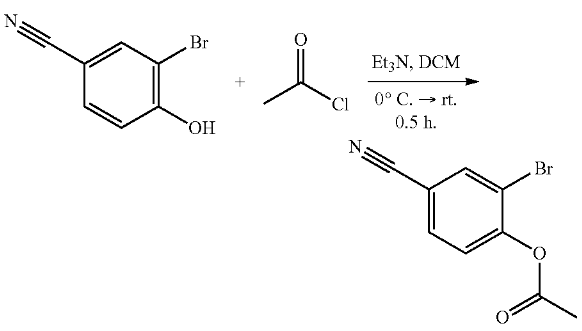

In a large, dry microwave vial, 2-bromo-4-cyanophenol (1.25 g, 6.31 mmol) was dissolved in anhydrous dichloromethane (19.1 mL) and anhydrous $Et_3N$ (1.4 mL). The mixture was cooled to 0° C., at which acetyl chloride (0.59 mL, 8.21 mmol) was slowly added. The mixture was stirred at rt. for 30 min. before it was quenched with $H_2O$ (0.2 mL) and diluted with additional $H_2O$ (10 mL) and separated. The aqueous phase was extracted with DCM (3×10 mL) and the combined organics were dried over $MgSO_4$ and evaporated in vacuo. The resulting residue was purified by Flash Chromatography ($SiO_2$, EtOAc:PE, 0-15%) to yield 1.36 g of B34 (90%, 5.67 mmol); $^1$H NMR (400 MHz, $CDCl_3$) δ 7.92 (d, J=2.0 Hz, 1H), 7.65 (d, J=8.4 Hz, 1H), 7.27 (dt, J=8.3, 1.1 Hz, 1H), 2.39 (d, J=1.2 Hz, 3H); $^{13}$C NMR (101 MHz, $CDCl_3$) δ 167.6, 152.0, 137.0, 132.4, 124.8, 117.4, 116.8, 111.5, 20.7; HRMS (ESI): m/z calculated for $C_9H_7BrNO_2$ (M+H+) mass not detected (App. 48.C).

4-cyano-2-((trimethylsilyl)ethynyl)phenyl acetate B35

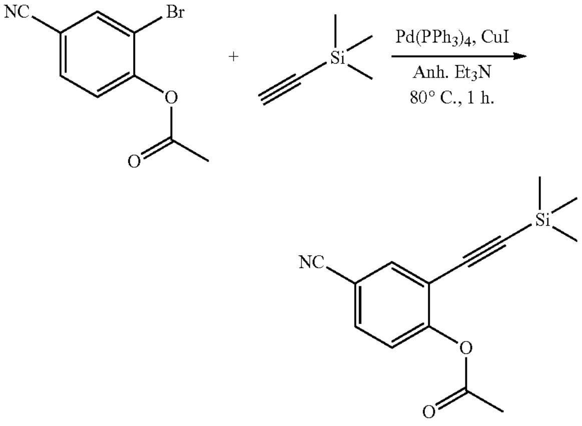

General Procedure 4 was applied with 2-bromo-4-cyanophenyl acetate B34 (1.25 g, 5.21 mmol), Copper(I) iodide (52.9 mg, 0.417 mmol), tetrakis(triphenylphosphine)palladium(0) (241 mg, 0.208 mmol), anhydrous $Et_3N$ (13.0) and trimethylsilyl acetylene (1.48 mL, 10.40 mmol). The reaction mixture was stirred at 80° C. for 1 h. before being cooled to rt. Flash Chromatography (EtOAc:PE, 0-5%) to yield 1.34 g of B35 (100%, 5.21 mmol) as white crystals; $^1H$ NMR (400 MHz, $CDCl_3$) δ 7.80 (d, J=2.0 Hz, 1H), 7.61 (dd, J=8.4, 2.1 Hz, 1H), 7.22 (d, J=8.4 Hz, 1H), 2.35 (s, 3H), 0.26 (s, 9H); $^{13}C$ NMR (101 MHz, $CDCl_3$) δ 168.1, 155.4, 137.4, 133.3, 123.9, 119.6, 117.75, 110.6, 103.3, 97.4, 21.1, 0.00; HRMS (ESI): m/z calculated for $C_{14}H_{15}NO_2Si$ (M+) 257.0872 mass not detected.

3-ethynyl-4-hydroxybenzonitrile B36

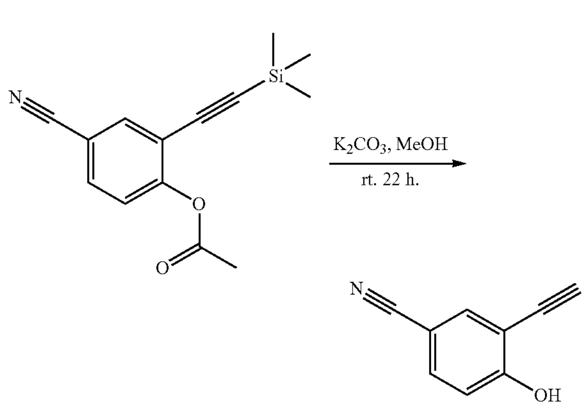

General Procedure 2 was applied with the trimethylsilyl protected acetylene B35 (900 mg, 3.50 mmol) dissolved in MeOH (25.3 mL) after which $K_2CO_3$ was added (1.01 g, 7.34 mmol). The suspension was stirred for 22 h. at rt. before it was concentrated in vacuo. The residue was purified by Flash Chromatography (EtOAc:PE, 0-50%) to yield 320 mg of B36 (64%, 2.24 mmol); $^1H$ NMR (400 MHz, $CDCl_3$) δ 7.72-7.67 (m, 1H), 7.56 (dd, J=8.7, 2.0 Hz, 1H), 7.05 (d, J=8.5 Hz, 1H), 6.29 (s, 1H), 3.57 (s, 1H) (App. 50.A); $^{13}C$ NMR (101 MHz, $CDCl_3$) δ 160.56, 136.35, 134.65, 118.09, 116.16, 109.93, 104.47, 86.49, 75.92 (App. 50.B); EI MS m/z calculated for $C_9H_5NO$ (M+) 143.0 found 143.0 (App. 50.C).

N1-(4-Ethynyl)benzyl thymine B37

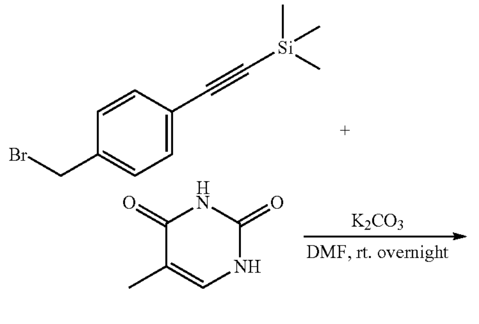

-continued

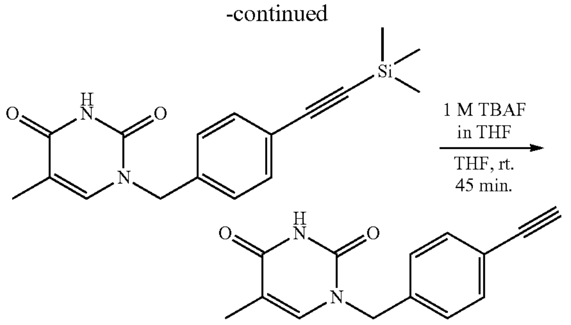

A round bottom flask was vac-filled with argon, before thymine (151 mg, 1.20 mmol), ((4-(bromomethyl)phenyl)ethynyl)trimethylsilane (267 mg, 1.00 mmol) were added and dissolved in 10.0 mL anhydrous dimethylformamide. Then $K_2CO_3$ (484 mg, 3.50 mmol) was added, and the reaction mixture was stirred at room temperature overnight, before it was concentrated in vacuo. The residue was dissolved in 15.0 mL dichloromethane, washed with brine (2×15 mL), dried over $MgSO_4$ and evaporated in vacuo. The resulting residue was purified by Flash chromatography (MeOH:DCM, 0%→1%→2%) to yield 142 mg of B37a (45%, 0.454 mmol); $^1H$-NMR (400 MHz, $CDCl_3$) δ 9.14 (s, 1H), 7.45-7.47 (d, 2H), 7.21-7.23 (d, 2H), 6.92-6.94 (q, 1H), 4.88 (s, 2H), 1.88 (s, 3H), 0.24 (s, 9H); $^{13}C$ NMR (101 MHz, $CDCl_3$) δ 164.1, 151.2, 139.6, 135.8, 132.7, 127.9, 123.6, 111.6, 104.3, 95.4, 50.8, 12.4, 0.1; HRMS (ESI) m/z calculated for $C_{17}H_{21}N_2O_2Si$ ($M+H^+$) 313.1372 found 313.1369. General Procedure 1 was applied with the trimethylsilyl acetylene B37a (138 mg, 0.442 mmol), anhydrous THF (2.0 mL) and 1 M TBAF in THF (0.69 mL, 0.69 mmol). The mixture was stirred at room temperature for 1 h. Purification by Flash chromatography (MeOH:DCM, 0%→1%→2%) yielded 82.0 mg of the alkyne B37 (78%, 0.341 mmol); $^1H$ NMR (400 MHz, $CDCl_3$) δ 8.85 (s, 1H), 7.50 (d, J=8.3 Hz, 2H), 7.25 (d, J=8.3 Hz, 2H), 6.96 (d, J=1.3 Hz, 1H), 4.89 (s, 2H), 3.11 (s, 1H), 1.89 (d, J=1.3 Hz, 3H); $^{13}C$ NMR δ 12.3, 50.7, 78.1, 82.9, 111.5, 123.5, 127.9, 132.8, 136.1, 139.5, 151.0, 163.8; HRMS (ESI) m/z calculated for $C_{14}H_{13}N_2O_2$ ($M+H^+$) 241.0977 found 241.0993.

(5-bromopyridin-2-yl)methyl 4-methylbenzenesulfonate B38

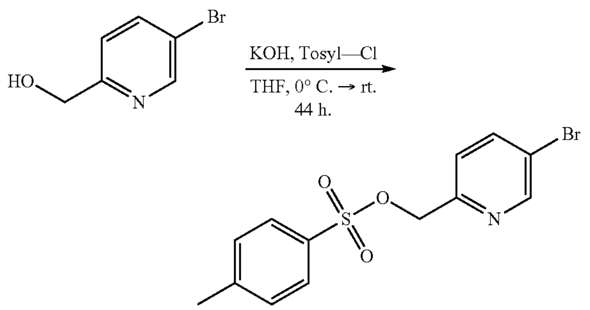

A solution of (500 mg, 2.66 mmol) in THF (13.3 mL) was vigorously stirred at 0° C., before powdered potassium hydroxide (224 mg, 3.99 mmol) was added. The suspension was stirred for 15 min. before p-toluenesulfonyl chloride (659 mg, 3.46 mmol) was added. Cooling was removed, and the reaction mixture was stirred at rt. for 44 hours. The reaction mixture was quenched with saturated $NaHCO_3$ and the product was extracted with ethyl acetate (3×10 mL). The combined organics were dried over MgSO4 and concentrated in vacuo. The residue was purified by Flash Chromatography (DCM) to afford 860 mg of B38 (95%, 2.51 mmol); $^1$H NMR (400 MHz, DMSO) δ 8.65 (dd, J=2.4, 0.7 Hz, 1H), 8.07 (dd, J=8.3, 2.4 Hz, 1H), 7.85-7.77 (m, 2H), 7.50-7.43 (m, 2H), 7.39 (dd, J=8.3, 0.7 Hz, 1H), 5.14 (s, 2H), 2.42 (s, 3H); $^{13}$C NMR (DMSO, 101 MHz) δ 152.0, 150.0, 145.1, 139.6, 132.2, 130.1, 127.6, 124.6, 120.1, 71.4, 21.0; HRMS (ESI): m/z calculated for $C_{13}H_{12}BrNNaO_3S$ ($M^+Na^+$) 363.9613 found 363.9631.

9-((5-bromopyridin-2-yl)methyl)-9H-purin-6-amine B39

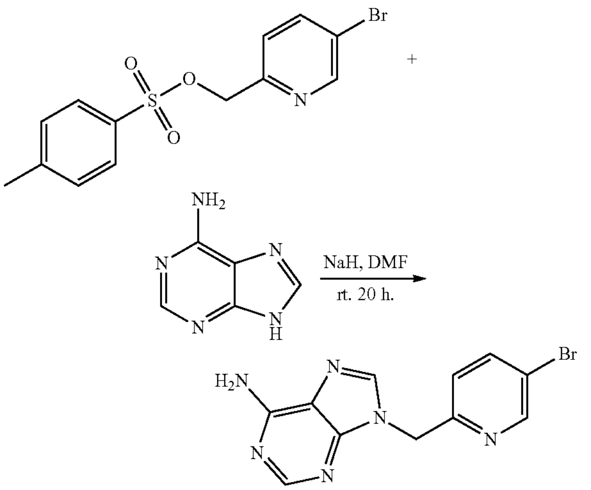

In a large, dry microwave vial, adenine (330 mg, 2.44 mmol) was suspended in anhydrous DMF (14.4 mL) before addition of NaH (50-60% in paraffin oil, 123 mg, 2.81 mmol). The vial was purged with argon and the suspension was stirred for 30 min. before B38 (836 mg, 2.44 mmol) in DMF (1.07 mL) was added. The mixture was stirred for additional 20 h. before the solvent was removed in vacuo. The residue was re-dissolved in MeOH and evaporated onto Celite 545 and purified by Flash Chromatography (MeOH: DCM, 10%) to yield 306 mg of B39 (43%, 1.05 mmol); $^1$H NMR (400 MHz, DMSO) δ 8.66-8.58 (m, 1H), 8.23 (s, 1H), 8.09 (s, 1H), 8.03 (dd, J=8.3, 2.4 Hz, 1H), 7.35-7.18 (m, 3H), 5.47 (s, 2H); $^{13}$C NMR (DMSO, 101 MHz) δ 155.9, 154.8, 152.5, 149.9, 149.5, 141.2, 139.6, 123.4, 119.1, 118.5, 47.0; HRMS (ESI): not recorded.

3-(6-((6-amino-9H-purin-9-yl)methyl)pyridin-3-yl) prop-2-yn-1-ol B40

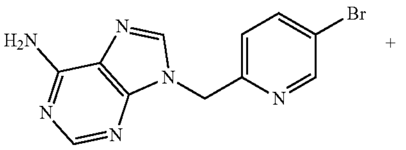

-continued

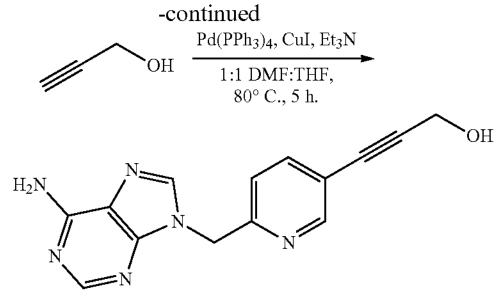

To a small, dry microwave vial, the aryl bromide B39 (100 mg, 0.328 mmol), copper(I) iodide (13 mg, 0.066 mmol), tetrakis(triphenylphosphine)palladium(0) (38 mg, 0.033 mmol) were added. The vial was vac-filled with argon (3×) before anhydrous DMF (1.2 mL), THF (1.2 mL), $Et_3N$ (0.9 mL) and propargyl alcohol (0.19 mL, 3.3 mmol) were added under the exclusion of oxygen. The vial was sealed and the mixture stirred at 80° C. for 5 h. before being cooled to room temperature. The reaction mixture was evaporated in vacuo and the residue purified by Flash Chromatography (MeOH:DCM, 15-20%) to yield 33 mg of B40 (36%, 0.118 mmol); $^1$H NMR (400 MHz, DMSO) δ 8.54 (dd, J=2.2, 0.9 Hz, 1H), 8.24 (s, 1H), 8.09 (s, 1H), 7.84 (dd, J=8.1, 2.2 Hz, 1H), 7.32-7.18 (m, 3H), 5.51 (s, 2H), 5.41 (t, J=6.0 Hz, 1H), 4.31 (d, J=5.9 Hz, 2H); $^{13}$C NMR (DMSO, 101 MHz) δ 156.0, 155.3, 152.6, 151.2, 149.6, 141.4, 139.4, 121.3, 118.6, 118.4, 93.2, 80.2, 49.4, 47.4; HRMS (ESI): m/z calculated for $C_{14}H_{13}N_6O$ ($M^+H^+$) 281.1145 found 281.1142.

C: Synthesis of the Pleuromutilin Derivatives

22-[4-(4-(4-((6-amino-9H-purin-9-yl)methyl)phenyl)-1H-1,2,3-triazol-1-yl]-22-deoxypleuromutilin C1

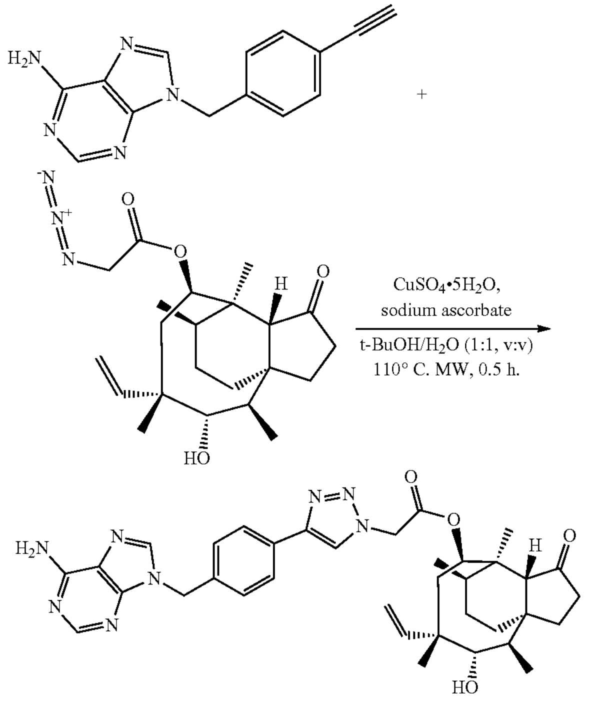

General Procedure 2 was applied with compound A3 (65 mg, 0.161 mmol), the alkyne B4 (40 mg, 0.161 mmol), sodium ascorbate (6.4 mg, 0.032 mmol) and $CuSO_4 \cdot 5H_2O$ (4.0 mg, 0.016 mmol) in degassed t-BuOH:$H_2O$ (1:1 v/v, 2.25 mL). Flash Chromatography (MeOH:DCM, 2-10%). Yield: 84 mg (80%, 0.129 mmol); $^1H$ NMR (400 MHz, $CDCl_3$) δ 8.42 (s, 1H), 7.86 (s, 2H), 7.82 (d, J=7.8 Hz, 2H), 7.35 (d, J=7.8 Hz, 2H), 6.41 (dd, J=17.4, 11.0 Hz, 1H), 5.82 (d, J=8.5 Hz, 3H), 5.40 (s, 2H), 5.33 (d, J=11.1 Hz, 1H), 5.24-5.05 (m, 3H), 3.49 (s, 2H), 3.36 (d, J=6.3 Hz, 1H), 2.23 (ddd, J=30.3, 13.1, 5.0 Hz, 4H), 2.09 (q, J=8.4 Hz, 2H), 1.84-1.37 (m, 9H), 1.34 (s, 4H), 1.32-1.24 (m, 1H), 1.17 (s, 3H), 1.15-1.07 (m, 1H), 0.87 (d, J=6.9 Hz, 3H), 0.72 (d, J=7.0 Hz, 3H); $^{13}C$ NMR (101 MHz, $CDCl_3$) δ 216.47, 165.01, 147.59, 138.62, 135.51, 130.63, 128.40, 126.52, 121.06, 117.60, 77.23, 74.57, 71.17, 58.02, 51.70, 45.43, 44.79, 44.05, 41.89, 36.57, 36.08, 34.39, 30.36, 26.81, 26.42, 24.83, 16.84, 14.65, 11.45; HRMS (ESI): m/z calculated for $C_{36}H_{45}N_8O_4$ (M+H+) 653.3558 found 653.3538; HPLC purity at 254 nm: 96.3%.

22-[4-(4-((N-phthalimide)methyl)phenyl)-1H-1,2,3-triazol-1-yl]-22-deoxypleuromutilin C2

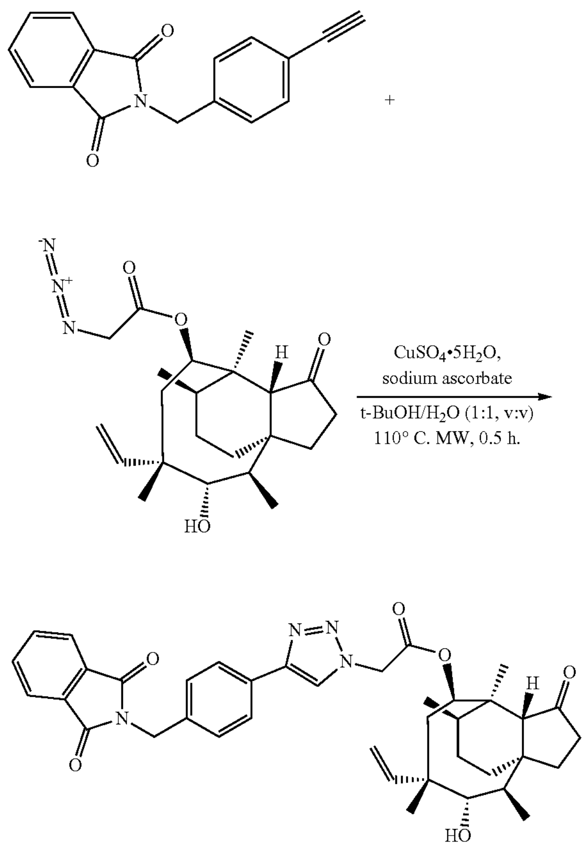

General Procedure 2 was applied with compound A3 (60 mg, 0.149 mmol), the alkyne B5 (38.9 mg, 0.149 mmol), sodium ascorbate (5.9 mg, 0.030 mmol) and $CuSO_4 \cdot 5H_2O$ (3.7 mg, 0.015 mmol) in degassed t-BuOH:$H_2O$ (1:1 v/v, 2.25 mL). Flash Chromatography (30-60% EtOAc:PE). Yield: 98 mg (99%, 0.147 mmol); $^1H$ NMR (400 MHz, $CDCl_3$) δ 7.86 (dd, J=5.5, 3.0 Hz, 2H), 7.83 (s, 1H), 7.80-7.77 (m, 2H), 7.74-7.69 (m, 2H), 7.53-7.47 (m, 2H), 6.41 (dd, J=17.4, 11.0 Hz, 1H), 5.82 (d, J=8.5 Hz, 1H), 5.33 (dd, J=11.0, 1.5 Hz, 1H), 5.21 (dd, J=17.3, 1.5 Hz, 1H), 5.17-5.03 (m, 2H), 4.88 (s, 2H), 3.35 (dd, J=9.9, 6.5 Hz, 1H), 2.34-2.05 (m, 7H), 1.76 (dq, J=14.4, 3.0 Hz, 1H), 1.71-1.59 (m, 3H), 1.57-1.37 (m, 4H), 1.34 (s, 3H), 1.17 (s, 3H), 0.87 (d, J=7.0 Hz, 3H), 0.71 (d, J=7.0 Hz, 3H); $^{13}C$ NMR (101 MHz, $CDCl_3$) δ 216.44, 168.03, 165.03, 147.92, 138.63, 136.49, 134.03, 132.18, 129.95, 129.21, 126.15, 123.42, 120.87, 117.60, 74.56, 71.08, 58.01, 51.67, 45.42, 44.79, 44.04, 41.88, 41.40, 36.57, 36.08, 34.38, 30.36, 26.81, 26.39, 24.82, 16.83, 14.64, 11.45; HRMS (ESI): m/z calculated for $C_{39}H_{45}N_4O_6$ (M+H+) 665.3334 found 665.3301; HPLC purity at 254 nm: 99.3%.

22-[4-(4-(4-((6-(4-methylpiperazin-1-yl)-9H-purin-9-yl)methyl)pheny)-1H-1,2,3-triazol-1-yl]-22-deoxypleuromutilin C3

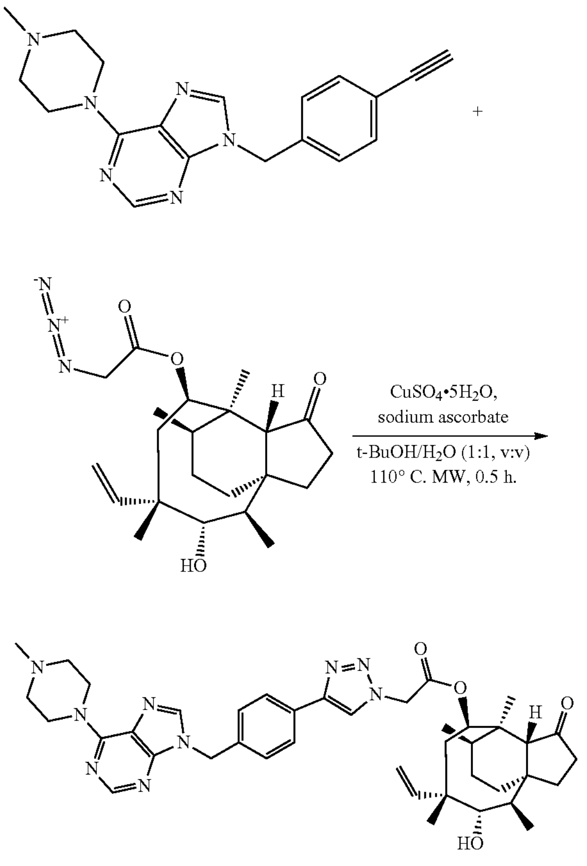

General Procedure 2 was applied with compound A3 (55 mg, 0.136 mmol), the alkyne B7 (45.3 mg, 0.136 mmol), sodium ascorbate (5.4 mg, 0.027 mmol) and $CuSO_4 \cdot 5H_2O$ (3.4 mg, 0.014 mmol) in degassed t-BuOH:$H_2O$ (1:1 v/v, 2.25 mL). Flash Chromatography (MeOH:DCM, 2-10%). Yield: 88 mg (88%, 0.120 mmol); $^1H$ NMR (400 MHz, $CDCl_3$) δ 8.39 (s, 1H), 7.84 (s, 1H), 7.81 (d, J=8.3 Hz, 2H), 7.74 (s, 1H), 7.34 (d, J=8.4 Hz, 2H), 6.41 (dd, J=17.4, 11.0

Hz, 1H), 5.83 (d, J=8.5 Hz, 1H), 5.40 (s, 2H), 5.34 (dd, J=11.0, 1.5 Hz, 1H), 5.21 (dd, J=17.4, 1.5 Hz, 1H), 5.18-5.03 (m, 2H), 4.35 (s, 4H), 3.35 (dd, J=10.0, 6.5 Hz, 1H), 2.56 (t, J=5.1 Hz, 4H), 2.35 (s, 3H), 2.32-2.04 (m, 5H), 1.82-1.72 (m, 2H), 1.65 (dtd, J=13.3, 10.9, 9.7, 6.8 Hz, 2H), 1.52 (s, 1H), 1.49-1.38 (m, 3H), 1.37-1.24 (m, 5H), 1.18 (s, 3H), 1.16-1.07 (m, 1H), 0.87 (d, J=7.0 Hz, 3H), 0.72 (d, J=7.0 Hz, 3H); $^{13}C$ NMR (101 MHz, $CDCl_3$) δ 216.47, 165.02, 154.00, 152.71, 151.13, 147.66, 138.60, 138.16, 135.88, 130.43, 128.25, 126.43, 120.99, 119.90, 117.62, 74.55, 71.13, 58.00, 55.17, 51.67, 46.81, 46.21, 45.41, 45.10, 44.77, 44.04, 41.88, 36.56, 36.07, 34.38, 30.35, 26.80, 26.39, 24.82, 16.84, 14.64, 11.45; HRMS (ESI): m/z calculated for $C_{41}H_{54}N_9O_4$ (M+H+) 736.4293 found 736.4297; HPLC purity at 254 nm: 98.3%.

22-[4-(4-(hydroxymethyl)phenyl)-1H-1,2,3-triazol-1-yl]-22-deoxypleuromutilin C4

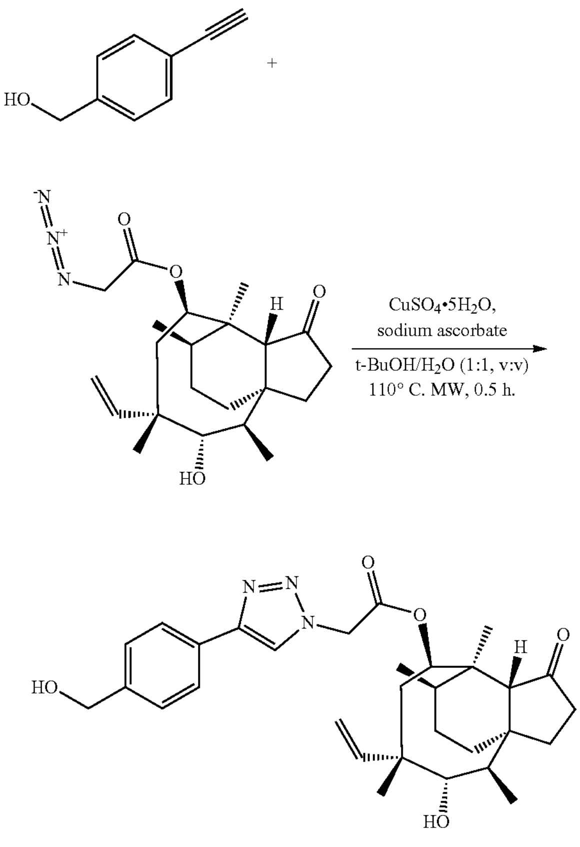

General Procedure 2 was applied with compound A3 (80 mg, 0.198 mmol), the alkyne B2 (26.2 mg, 0.198 mmol), sodium ascorbate (7.9 mg, 0.040 mmol) and $CuSO_4·5H_2O$ (5.0 mg, 0.020 mmol) in degassed t-BuOH:$H_2O$ (1:1 v/v, 2.25 mL). Flash Chromatography (15-100% EtOAc:PE). Yield: 102 mg (96%, 0.191 mmol); $^1H$ NMR (400 MHz, $CDCl_3$) δ 7.86 (s, 1H), 7.85-7.80 (m, 2H), 7.47-7.41 (m, 2H), 6.42 (dd, J=17.4, 11.0 Hz, 1H), 5.84 (d, J=8.5 Hz, 1H), 5.35 (dd, J=11.0, 1.5 Hz, 1H), 5.22 (dd, J=17.3, 1.5 Hz, 1H), 5.19-5.04 (m, 2H), 4.74 (s, 2H), 3.40-3.31 (m, 1H), 2.33-2.04 (m, 5H), 1.77 (dq, J=14.4, 3.1 Hz, 1H), 1.66 (tdd, J=13.8, 10.6, 6.6 Hz, 3H), 1.58-1.39 (m, 4H), 1.36 (s, 4H), 1.32 (s, 1H), 0.88 (d, J=7.0 Hz, 3H), 0.73 (d, J=7.1 Hz, 3H); $^{13}C$ NMR (101 MHz, $CDCl_3$) δ 216.53, 165.09, 148.11, 141.11, 138.63, 129.69, 127.47, 126.05, 120.84, 117.63, 74.56, 71.09, 65.07, 58.02, 51.68, 45.43, 44.78, 44.04, 41.89, 36.58, 36.08, 34.39, 30.36, 26.81, 26.39, 24.82, 16.84, 14.65, 11.46; HRMS (ESI): m/z calculated for $C_{31}H_{42}N_3O_5$ (M+H+) 536.3119 found 536.3100; HPLC purity at 254 nm: 96.6%.

22-[4-(4-((6-Amino-2-fluoro-9H-purin-9-yl)methyl)phenyl)-1H-1,2,3-triazol-1-yl]-22-deoxypleuromutilin C5

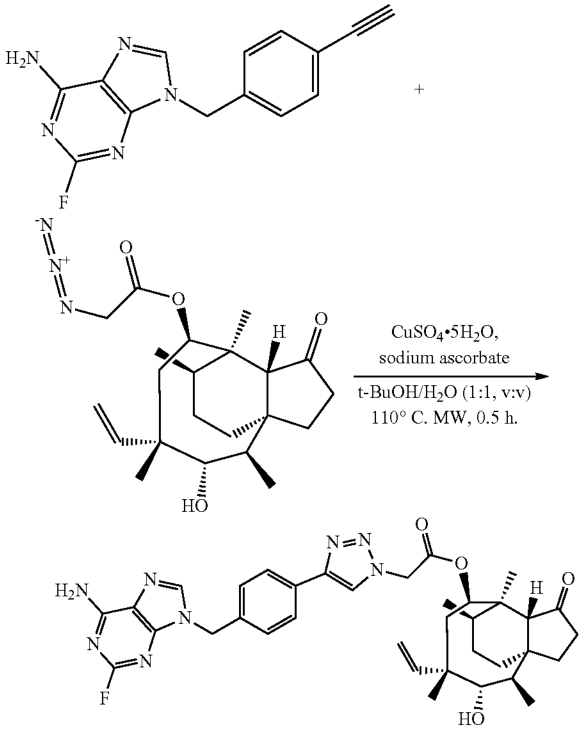

A slightly altered General Procedure 2 was applied with the alkyne B8 (41 mg, 0.153 mmol) as limiting reagent, compound A3 (65 mg, 0.161 mmol), sodium ascorbate (6.4 mg, 0.032 mmol) and $CuSO_4·5H_2O$ (4.0 mg, 0.016 mmol) in degassed t-BuOH:$H_2O$ (1:1 v/v, 2.25 mL). Flash Chromatography (MeOH:DCM, 3-10%). Yield: 100 mg (98%, 0.149 mmol); $^1H$ NMR (400 MHz, DMSO) δ 8.50 (s, 1H), 8.26 (s, 1H), 7.84 (d, J=8.3 Hz, 4H), 7.39 (d, J=8.3 Hz, 2H), 6.13 (dd, J=17.8, 11.2 Hz, 1H), 5.58 (d, J=8.2 Hz, 1H), 5.47-5.25 (m, 4H), 5.19-5.00 (m, 2H), 4.54 (d, J=6.0 Hz, 1H), 3.41 (t, J=6.1 Hz, 1H), 2.40 (s, 1H), 2.27-1.96 (m, 4H), 1.63 (t, J=13.9 Hz, 2H), 1.53-1.43 (m, 1H), 1.42-1.25 (m, 4H), 1.22 (s, 4H), 1.07 (s, 3H), 0.81 (d, J=6.9 Hz, 3H), 0.63 (d, J=6.9 Hz, 3H); $^{13}C$ NMR (DMSO, 101 MHz) δ 216.8, 165.4, 157.7, 157.5, 150.8, 150.8, 150.6, 145.8, 141.1, 140.6, 136.2, 130.0, 128.1, 125.5, 122.8, 115.3, 72.4, 70.6, 57.0, 51.2, 46.0, 44.8, 44.0, 43.3, 41.4, 36.3, 36.1, 33.9, 30.0, 28.4, 26.5, 24.3, 16.0, 14.1, 11.4; HRMS (ESI): m/z calculated for $C_{36}H_{44}FN_8O_4$ ($M^+H^+$) 671.3464 found 671.3438; HPLC purity at 254 nm: 96.3%.

22-[4-(4-((2,6-Diamino-9H-purin-9-yl)methyl)phenyl)-1H-1,2,3-triazol-1-yl]-22-deoxypleuromutilin C6

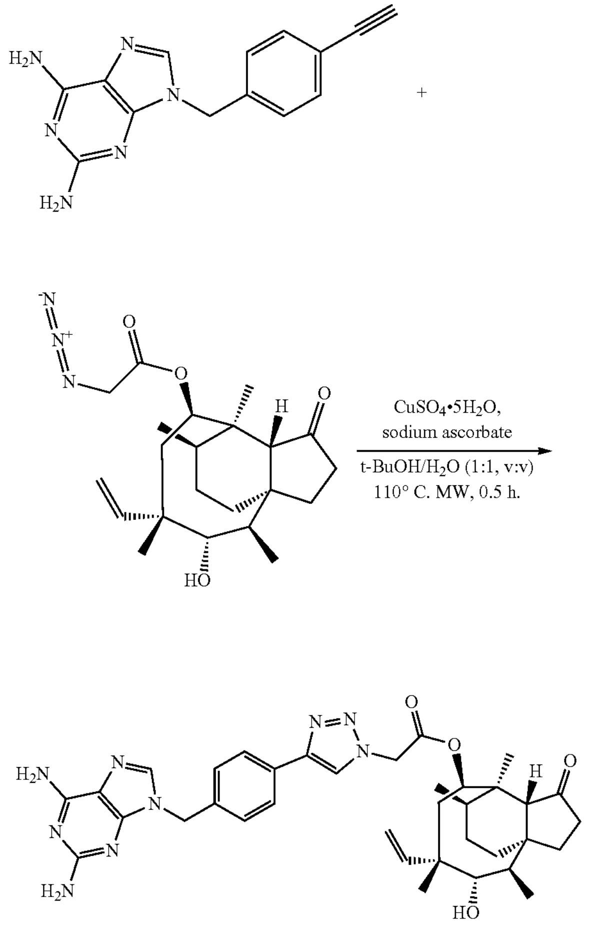

General Procedure 2 was applied with compound A3 (65 mg, 0.161 mmol), the alkyne B9 (42.6 mg, 0.161 mmol), sodium ascorbate (6.4 mg, 0.032 mmol) and $CuSO_4{\cdot}5H_2O$ (4.0 mg, 0.016 mmol) in degassed t-BuOH:$H_2O$ (1:1 v/v, 2.25 mL). Flash Chromatography (MeOH:DCM, 10%). Yield: 75 mg (70%, 0.113 mmol); $^1H$ NMR (400 MHz, DMSO) δ 8.49 (s, 1H), 7.82 (d, J=8.1 Hz, 3H), 7.31 (d, J=8.0 Hz, 2H), 6.71 (s, 2H), 6.13 (dd, J=17.8, 11.2 Hz, 1H), 5.82 (s, 2H), 5.57 (d, J=8.3 Hz, 1H), 5.36 (q, J=17.6 Hz, 2H), 5.23 (s, 2H), 5.18-5.01 (m, 2H), 4.55 (d, J=6.0 Hz, 1H), 3.42 (t, J=6.0 Hz, 1H), 2.44-2.37 (m, 1H), 2.24-1.98 (m, 4H), 1.70-1.18 (m, 10H), 1.07 (s, 3H), 0.99 (td, J=13.9, 4.4 Hz, 1H), 0.80 (d, J=6.9 Hz, 3H), 0.63 (d, J=7.0 Hz, 3H); $^{13}C$ NMR (DMSO, 101 MHz) δ 216.9, 165.4, 160.3, 156.1, 145.9, 140.6, 137.2, 129.7, 127.6, 125.3, 122.7, 115.3, 72.4, 70.6, 57.0, 51.2, 45.2, 44.8, 44.0, 43.3, 41.4, 36.3, 36.1, 33.9, 29.9, 28.4, 26.4, 24.3, 16.0, 14.1, 11.4; HRMS (ESI): m/z calculated for $C_{36}H_{46}N_9O_4$ ($M^+H^+$) 668.3667 found 668.3644; HPLC purity at 254 nm: 99.0%.

22-[4-(6-((6-Amino-9H-purin-9-yl)methyl)pyridin-3-yl)-1H-1,2,3-triazol-1-yl]-22-deoxypleuromutilin C7

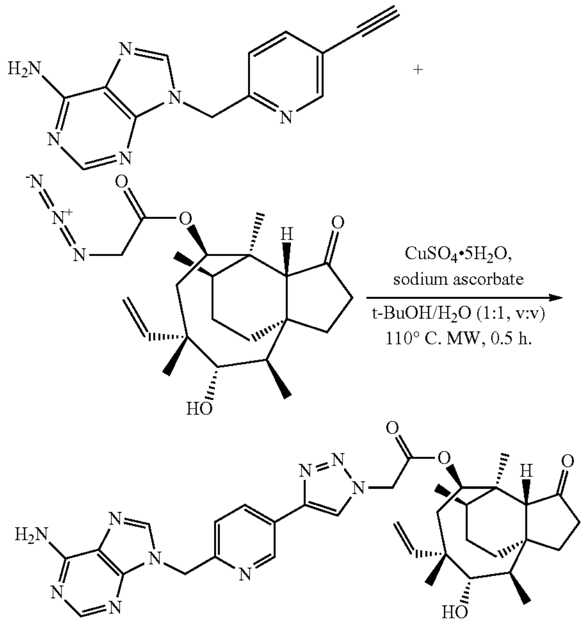

General Procedure 2 was applied with compound A3 (60 mg, 0.149 mmol), the alkyne B13 (37.2 mg, 0.149 mmol), sodium ascorbate (5.9 mg, 0.030 mmol) and $CuSO_4{\cdot}5H_2O$ (3.7 mg, 0.015 mmol) in degassed t-BuOH:$H_2O$ (1:1 v/v, 2.25 mL). Flash Chromatography (MeOH:DCM, 10%). Yield: 81 mg (84%, 0.124 mmol); $^1H$ NMR (400 MHz, DMSO) δ 8.97 (s, 1H), 8.63 (s, 1H), 8.27 (s, 1H), 8.22 (dd, J=8.1, 2.1 Hz, 1H), 8.11 (s, 1H), 7.34 (d, J=8.2 Hz, 1H), 7.25 (s, 2H), 6.12 (dd, J=17.8, 11.2 Hz, 1H), 5.58 (d, J=8.3 Hz, 1H), 5.53 (s, 2H), 5.50-5.32 (m, 2H), 5.16-5.01 (m, 2H), 4.55 (d, J=6.0 Hz, 1H), 3.42 (t, J=6.1 Hz, 1H), 2.40 (s, 1H), 2.26-1.96 (m, 4H), 1.71-1.19 (m, 10H), 1.07 (s, 3H), 0.99 (td, J=13.8, 4.4 Hz, 1H), 0.81 (d, J=6.9 Hz, 3H), 0.63 (d, J=7.0 Hz, 3H); $^{13}C$ NMR (DMSO, 101 MHz) δ 216.8, 165.4, 155.9, 155.2, 152.5, 149.6, 146.0, 143.2, 141.3, 140.6, 133.4, 125.5, 123.4, 121.7, 118.6, 115.3, 72.5, 70.6, 57.0, 51.3, 44.8, 44.0, 43.3, 41.4, 36.3, 36.1, 33.9, 30.0, 28.4, 26.5, 24.3, 16.0, 14.1, 11.4; HRMS (ESI): m/z calculated for $C_{35}H_{44}N_9O_4$ ($M^+H^+$) 654.3511 found 654.3520; HPLC purity at 254 nm: >99.9%.

22-[4-(4-((6-Amino-9H-purin-9-yl)methyl)-3-methoxyphenyl)-1H-1,2,3-triazol-1-yl]-22-deoxypleuromutilin C8

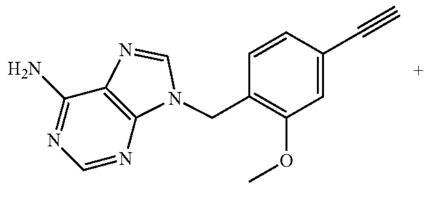

-continued

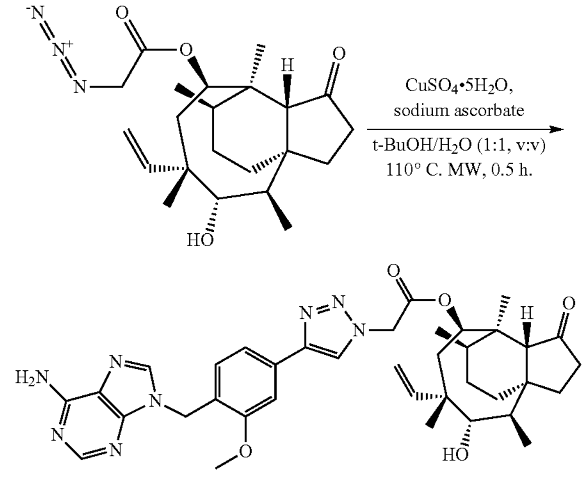

General Procedure 2 was applied with compound A3 (40 mg, 0.099 mmol), the alkyne B16 (27.7 mg, 0.099 mmol), sodium ascorbate (3.9 mg, 0.020 mmol) and $CuSO_4 \cdot 5H_2O$ (2.5 mg, 0.010 mmol) in degassed t-BuOH:$H_2O$ (1:1 v/v, 2.25 mL). Flash Chromatography (MeOH:DCM, 8%). Yield: 67 mg (99%, 0.98 mmol); $^1H$ NMR (400 MHz, DMSO) δ 8.56 (s, 1H), 8.14 (s, 2H), 7.53 (d, J=1.5 Hz, 1H), 7.38 (dd, J=7.7, 1.5 Hz, 1H), 7.22 (s, 2H), 7.03 (d, J=7.8 Hz, 1H), 6.13 (dd, J=17.8, 11.2 Hz, 1H), 5.58 (d, J=8.2 Hz, 1H), 5.49-5.23 (m, 4H), 5.12 (dd, J=17.8, 1.8 Hz, 1H), 5.05 (dd, J=11.2, 1.8 Hz, 1H), 4.55 (d, J=6.1 Hz, 1H), 3.94 (s, 3H), 3.42 (t, J=6.1 Hz, 1H), 2.41 (s, 1H), 2.24-2.00 (m, 4H), 1.68-1.22 (m, 10H), 1.07 (s, 3H), 1.04-0.94 (m, 1H), 0.81 (d, J=6.9 Hz, 3H), 0.64 (d, J=6.9 Hz, 3H); $^{13}C$ NMR (DMSO, 101 MHz) δ 216.8, 165.5, 157.1, 155.9, 152.5, 146.0, 140.7, 131.7, 129.2, 124.1, 123.0, 117.2, 115.3, 107.6, 72.5, 70.6, 57.0, 55.6, 51.2, 44.8, 44.1, 43.3, 41.6, 41.4, 40.1, 36.3, 36.1, 33.9, 30.0, 28.4, 26.5, 24.3, 16.1, 14.1, 11.4; HRMS (ESI): m/z calculated for $C_{37}H_{47}N_8O_5$ ($M^+H^+$) 683.3664 found 683.3652; HPLC purity at 254 nm: 97.4%.

22-[4-(4-((6-amino-9H-purin-9-yl)methyl)-3-hydroxyphenyl)-1H-1,2,3-triazol-1-yl]-22-deoxypleuromutilin C9

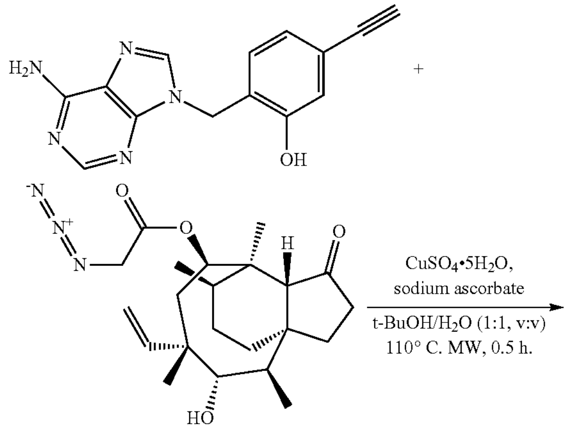

-continued

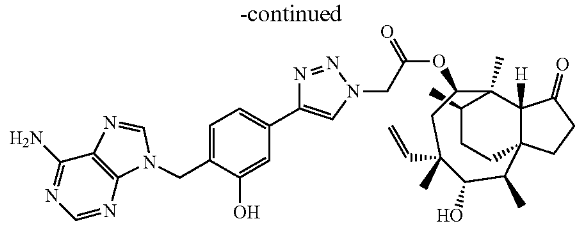

General Procedure 2 was applied with compound A3 (20 mg, 0.050 mmol), the alkyne B17 (13.2 mg, 0.050 mmol), sodium ascorbate (2.0 mg, 0.010 mmol) and $CuSO_4 \cdot 5H_2O$ (1.2 mg, 0.005 mmol) in degassed t-BuOH:$H_2O$ (1:1 v/v, 1.25 mL). Flash Chromatography (MeOH:DCM, 15%). Yield: 10 mg (30%, 0.015 mmol); $^1H$ NMR (400 MHz, DMSO) δ 10.17 (s, 1H), 8.41 (s, 1H), 8.14 (d, J=3.6 Hz, 2H), 7.40 (d, J=1.7 Hz, 1H), 7.23 (s, 2H), 7.18 (dd, J=7.8, 1.6 Hz, 1H), 7.03 (d, J=7.9 Hz, 1H), 6.13 (dd, J=17.7, 11.2 Hz, 1H), 5.57 (d, J=8.2 Hz, 1H), 5.42-5.26 (m, 4H), 5.17-5.01 (m, 2H), 4.55 (d, J=6.0 Hz, 1H), 3.41 (t, J=6.1 Hz, 1H), 2.40 (s, 1H), 2.23-1.98 (m, 4H), 1.61 (q, J=13.2, 10.7 Hz, 2H), 1.52-1.42 (m, 1H), 1.36 (d, J=15.6 Hz, 2H), 1.28-1.23 (m, 2H), 1.21 (s, 3H), 1.07 (s, 3H), 0.99 (td, J=13.9, 4.0 Hz, 1H), 0.81 (d, J=6.9 Hz, 3H), 0.63 (d, J=6.9 Hz, 3H); $^{13}C$ NMR (DMSO, 101 MHz) δ 216.8, 165.4, 155.9, 155.4, 152.4, 149.5, 145.9, 140.9, 140.6, 131.3, 129.7, 122.7, 122.6, 118.5, 116.2, 115.3, 111.8, 72.4, 70.6, 57.0, 51.1, 44.8, 44.0, 43.2, 41.7, 41.4, 36.3, 36.1, 33.9, 29.9, 28.4, 26.5, 24.3, 16.0, 14.1, 11.4; HRMS (ESI): m/z calculated for $C_{35}H_{45}N_8O_5$ ($M^+H^+$) 669.8065 found 669.8051; HPLC purity at 254 nm: 98.0%.

22-[4-(6-((6-(piperazin-1-yl)-9H-purin-9-yl)methyl)pyridin-3-yl)-1H-1,2,3-triazol-1-yl]-22-deoxypleuromutilin C10

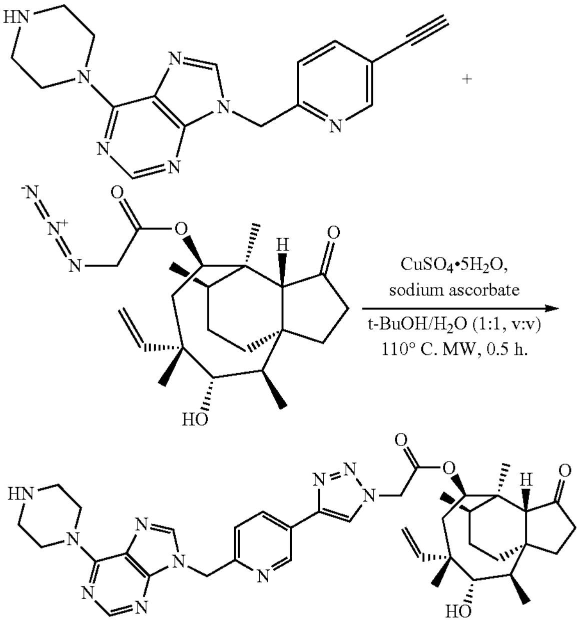

A slightly altered General Procedure 2 was applied with the alkyne B20 (29 mg, 0.091 mmol) as limiting reagent, compound A3 (38.5 mg, 0.095 mmol), sodium ascorbate (3.6 mg, 0.018 mmol) and $CuSO_4 \cdot 5H_2O$ (2.3 mg, 0.016 mmol) in degassed t-BuOH:$H_2O$ (1:1 v/v, 2.25 mL). Flash Chromatography (MeOH:DCM, 2-25%). Yield: 65 mg (99%, 0.090 mmol); $^1H$ NMR (400 MHz, DMSO) δ 8.96 (dd, J=2.3, 0.9 Hz, 1H), 8.63 (s, 1H), 8.31 (s, 1H), 8.22 (dd, J=8.1, 2.3 Hz, 1H), 8.19 (s, 1H), 7.34 (dd, J=8.2, 0.8 Hz, 1H), 6.12 (dd, J=17.8, 11.2 Hz, 1H), 5.56 (d, J=7.1 Hz, 3H), 5.49-5.33 (m, 2H), 5.16-5.00 (m, 2H), 4.57 (s, 1H), 4.16 (s, 4H), 3.41 (s, 1H), 3.32 (s, 2H), 2.81 (t, J=5.1 Hz, 4H), 2.41 (s, 1H), 2.24-1.97 (m, 4H), 1.61 (q, J=12.7, 10.7 Hz, 2H), 1.48 (ddd, J=11.0, 7.0, 3.7 Hz, 1H), 1.36 (dd, J=14.0, 8.7 Hz, 2H), 1.32-1.24 (m, 2H), 1.23 (s, 3H), 1.07 (s, 3H), 0.99 (td, J=13.9, 4.5 Hz, 1H), 0.80 (d, J=7.0 Hz, 3H), 0.63 (d, J=7.0 Hz, 3H); $^{13}C$ NMR (DMSO, 101 MHz) δ 216.8, 165.4, 155.1, 153.2, 151.8, 150.6, 146.0, 143.2, 140.6, 140.3, 133.4, 125.5, 123.4, 121.7, 118.8, 115.3, 72.4, 70.6, 57.0, 51.3, 47.4, 45.7, 44.8, 44.0, 43.2, 41.4, 36.3, 36.1, 33.9, 30.8, 29.9, 28.4, 26.4, 24.3, 16.0, 14.1, 11.4; HRMS (ESI): m/z calculated for $C_{39}H_{51}N_{10}O_4$ ($M^+H^+$) 723.4089 found 723.4080; HPLC purity at 254 nm: 99.4%.

22-[4-(4-((6-(piperazin-1-yl)-9H-purin-9-yl)methyl) phenyl)-1H-1,2,3-triazol-1-yl]-22-deoxypleuromutilin C11

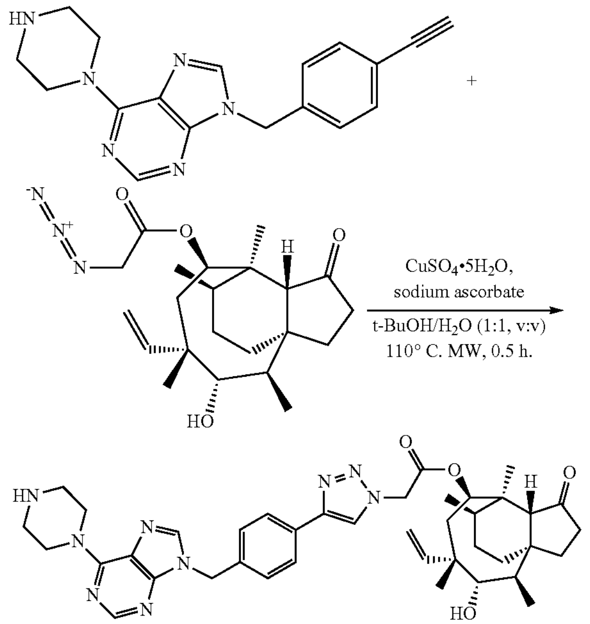

A slightly altered General Procedure 2 was applied with the alkyne B22 (40 mg, 87%, 0.109 mmol) as limiting reagent, compound A3 (48.5 mg, 0.120 mmol), sodium ascorbate (4.3 mg, 0.022 mmol) and $CuSO_4 \cdot 5H_2O$ (2.7 mg, 0.010 mmol) in degassed t-BuOH:$H_2O$ (1:1 v/v, 2.25 mL). Flash Chromatography (MeOH:DCM, 2-25%). Yield: 56 mg (71%, 0.077 mmol); $^1H$ NMR (400 MHz, DMSO) δ 8.50 (s, 1H), 8.32 (d, J=1.4 Hz, 1H), 8.24 (s, 1H), 7.92 (d, J=8.3 Hz, 0H), 7.82 (d, J=8.3 Hz, 2H), 7.39 (d, J=8.4 Hz, 2H), 6.13 (dd, J=17.8, 11.2 Hz, 1H), 5.57 (d, J=8.3 Hz, 1H), 5.45-5.27 (m, 4H), 5.16-5.01 (m, 2H), 4.56 (d, J=5.9 Hz, 1H), 4.15 (s, 4H), 3.41 (d, J=6.0 Hz, 1H), 3.33 (s, 3H), 2.86 (s, 4H), 2.40 (s, 1H), 2.10 (dtd, J=32.0, 16.4, 13.6, 9.2 Hz, 4H), 1.61 (q, J=12.8, 10.6 Hz, 2H), 1.53-1.41 (m, 1H), 1.36 (d, J=15.9 Hz, 2H), 1.27 (t, J=12.6 Hz, 2H), 1.22 (s, 3H), 1.07 (s, 3H), 1.04-0.95 (m, 1H), 0.80 (d, J=6.9 Hz, 3H), 0.63 (d, J=7.0 Hz, 3H); $^{13}C$ NMR (DMSO, 101 MHz) δ 216.8, 165.4, 153.2, 151.9, 150.5, 145.9, 140.6, 139.7, 136.6, 130.0, 128.1, 125.4, 122.7, 118.9, 115.3, 72.4, 70.6, 57.0, 51.2, 48.5, 45.9, 44.8, 44.0, 43.3, 41.4, 36.3, 36.1, 33.9, 29.9, 28.4, 26.6, 26.5, 24.3, 16.0, 14.1, 11.4; HRMS (ESI): m/z calculated for $C_{40}H_{52}N_9O_4$ ($M^+H^+$) 722.4137 found 722.4135; HPLC purity at 254 nm: 98.9%.

22-[4-(4-((R)-1-(6-amino-9H-purin-9-yl)ethyl)phenyl)-1H-1,2,3-triazol-1-yl]-22-deoxypleuromutilin C12

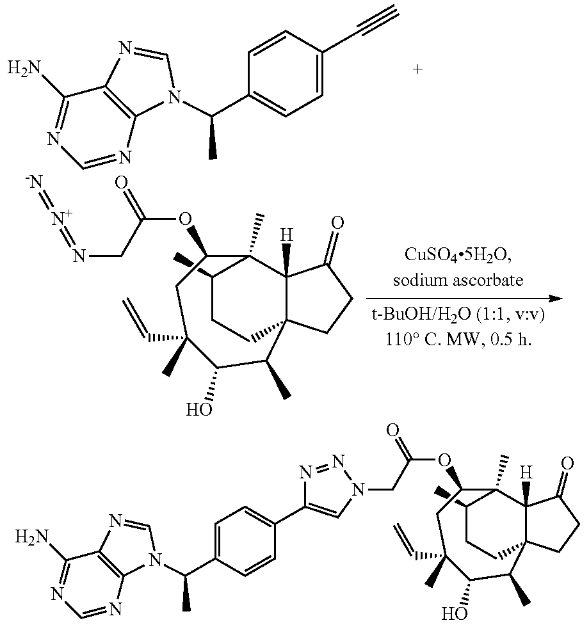

A slightly altered General Procedure 2 was applied with the alkyne B26 (33 mg, 0.125 mmol) as limiting reagent, compound A3 (53 mg, 0.131 mmol), sodium ascorbate (5.0 mg, 0.025 mmol) and $CuSO_4 \cdot 5H_2O$ (3.1 mg, 0.013 mmol) in degassed t-BuOH:$H_2O$ (1:1 v/v, 2.25 mL). Flash Chromatography (MeOH:DCM, 2-10%). Yield: 72 mg (86%, 0.108 mmol); $^1H$ NMR (400 MHz, DMSO) δ 8.50 (s, 1H), 8.43 (s, 1H), 8.13 (s, 1H), 7.89-7.77 (m, 2H), 7.48-7.39 (m, 2H), 7.25 (s, 2H), 6.13 (dd, J=17.8, 11.2 Hz, 1H), 5.86 (q, J=7.1 Hz, 1H), 5.57 (d, J=8.3 Hz, 1H), 5.36 (q, J=17.6 Hz, 2H), 5.19-4.99 (m, 2H), 4.56 (d, J=6.0 Hz, 1H), 3.41 (t, J=6.1 Hz, 1H), 2.40 (s, 1H), 2.23-2.00 (m, 4H), 1.97 (d, J=7.2 Hz, 3H), 1.61 (q, J=13.0, 10.7 Hz, 2H), 1.47 (ddd, J=11.0, 7.0, 3.5 Hz, 1H), 1.36 (d, J=15.9 Hz, 2H), 1.27 (t, J=3.0 Hz, 2H), 1.23-1.20 (m, 3H), 1.07 (s, 3H), 0.99 (td, J=13.8, 4.4 Hz, 1H), 0.80 (d, J=6.9 Hz, 3H), 0.63 (d, J=6.9 Hz, 3H); $^{13}C$ NMR (DMSO, 101 MHz) δ 216.8, 165.4, 155.9, 152.3, 145.8, 141.2, 140.6, 139.1, 139.1, 129.9, 126.8, 125.4, 122.7, 115.3, 72.4, 70.6, 57.0, 54.8, 52.9, 51.2, 44.8, 44.0, 43.3, 41.4, 36.3, 36.1, 33.9, 29.9, 28.4, 26.4, 24.3, 20.3, 16.0, 14.1, 11.4; HRMS (ESI): m/z calculated for $C_{37}H_{47}N_8O_4$ ($M^+H^+$) 667.3715 found 667.3706; HPLC purity at 254 nm: 99.9%.

22-[4-(4-((R)-1-(6-(piperazin-1-yl)-9H-purin-9-yl)ethyl)phenyl)-1H-1,2,3-triazol-1-yl]-22-deoxypleuromutilin C13

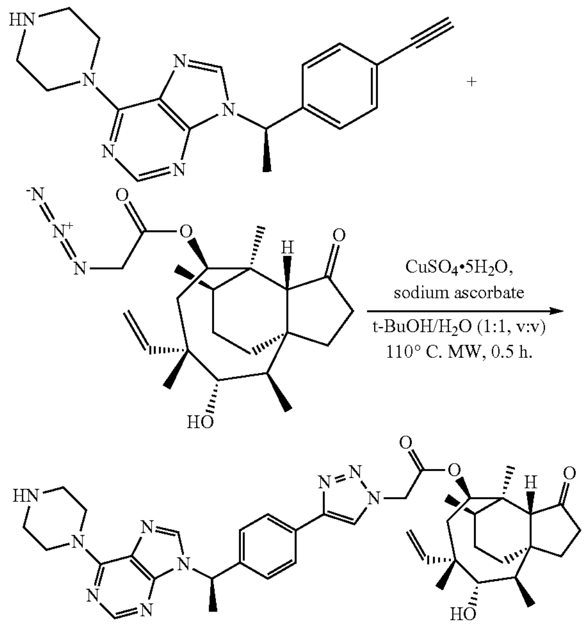

A slightly altered General Procedure 2 was applied with the alkyne B28 (68 mg, 0.205 mmol) as limiting reagent, compound A3 (87 mg, 0.215 mmol), sodium ascorbate (8.1 mg, 0.041 mmol) and $CuSO_4 \cdot 5H_2O$ (5.1 mg, 0.021 mmol) in degassed t-BuOH:$H_2O$ (1:1 v/v, 2.25 mL). Flash Chromatography (MeOH:DCM, 2-25%). Yield: 141 mg (94%, 0.191 mmol); $^1$H NMR (400 MHz, DMSO) δ 8.50 (s, 1H), 8.46 (s, 1H), 8.21 (s, 1H), 7.89-7.75 (m, 2H), 7.51-7.34 (m, 2H), 6.13 (dd, J=17.8, 11.2 Hz, 1H), 5.90 (q, J=7.2 Hz, 1H), 5.57 (d, J=8.3 Hz, 1H), 5.36 (q, J=17.6 Hz, 2H), 5.18-4.99 (m, 2H), 4.57 (d, J=5.8 Hz, 1H), 4.16 (s, 4H), 3.41 (s, 1H), 3.32 (s, 3H), 2.80 (t, J=5.1 Hz, 4H), 2.43-2.37 (m, 1H), 2.24-2.00 (m, 4H), 1.97 (d, J=7.2 Hz, 3H), 1.71-1.54 (m, 2H), 1.47 (ddt, J=11.5, 8.1, 4.1 Hz, 1H), 1.38 (d, J=4.2 Hz, 1H), 1.34 (s, 1H), 1.31-1.23 (m, 2H), 1.22 (s, 3H), 1.07 (s, 3H), 0.99 (td, J=13.8, 4.4 Hz, 1H), 0.80 (d, J=6.9 Hz, 3H), 0.63 (d, J=7.0 Hz, 3H); $^{13}$C NMR (DMSO, 101 MHz) δ 216.8, 165.4, 153.1, 151.7, 150.2, 145.8, 141.0, 140.6, 138.0, 129.9, 126.8, 125.4, 122.8, 119.1, 115.3, 72.4, 70.6, 57.0, 54.8, 52.8, 51.2, 45.6, 44.8, 44.0, 43.3, 41.4, 36.3, 36.1, 33.9, 29.9, 28.4, 26.5, 24.3, 20.3, 16.0, 14.1, 11.4; HRMS (ESI): m/z calculated for $C_{41}H_{54}N_9O_4$ ($M^+H^+$) 736.4291 found 736.4291; HPLC purity at 254 nm: 99.9%.

22-[4-(3-benzamidophenyl)-1,2,3-triazole-1-yl]-22-deoxypleuromutilin C14

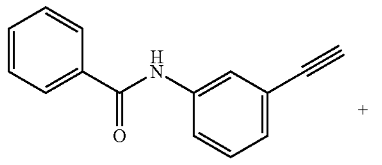

-continued

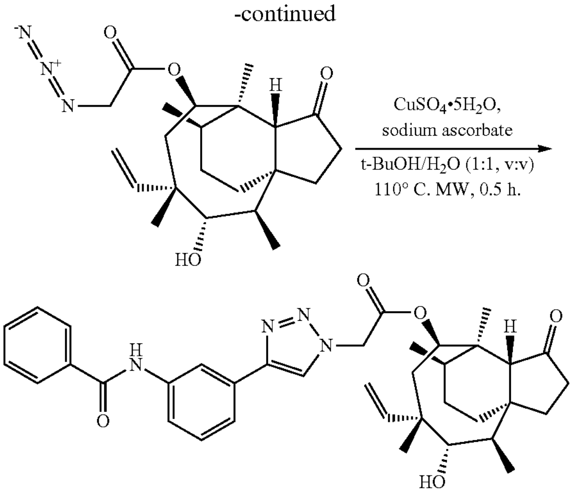

General Procedure 2 was applied with compound A3 (101 mg, 0.250 mmol), the alkyne B29 (62 mg, 0.280 mmol), sodium ascorbate (20.9 mg, 0.100 mmol) and $CuSO_4 \cdot 5H_2O$ (25.2 mg, 0.100 mmol) in degassed t-BuOH:$H_2O$ (1:1 v/v, 12 mL). Flash Chromatography (MeOH:DCM, 3%). Yield: 153 mg (98%, 0.245 mmol); $^1$H NMR (400 MHz, $CDCl_3$): δ 8.11 (t, J=1.9 Hz, 1H), 8.07 (s, 1H), 7.93-7.86, (m, 3H), 7.72 (ddd, J=8.1, 2.2, 1.0 Hz), 7.62 (dt, J=7.8, 1.2 Hz), 7.59-7.53 (m, 1H), 7.53-7.46 (m, 2H), 7.43 (t, J=7.9 Hz), 6.42 (dd, J=17.4, 11.0 Hz), 5.83 (d, J=8.5 Hz), 5.37-5.18 (m, 2H), 5.18-5.02 (m, 2H), 3.36 (dd, J=10.4, 6.4 Hz, 1H), 2.34-2.03 (m, 5H), 1.80-1.06 (m, 15H), 0.87 (d, J=7.0 Hz, 3H), 0.73 (d, J=7.0 Hz, 3H); $^{13}$C NMR (101 MHz, $CDCl_3$): δ 216.6, 165.8, 165.0, 147.9, 138.6, 134.9, 132.0, 131.2, 129.7, 128.8, 127.1, 121.9, 121.3, 112.0, 117.6, 117.4, 74.5, 71.1, 58.0, 51.7, 45.4, 44.7, 44.0, 41.9, 36.6, 36.1, 34.4, 30.3, 26.8, 26.4, 24.8, 16.9, 14.6, 11.5; HRMS (ESI): m/z calculated for $C_{37}H_{45}N_4O_5$ ($M^+H^+$) 625.3384 found 625.3353.

22-[4-(3-(4-methoxybenzamido)phenyl)-1,2,3-triazole-1-yl]-22-deoxypleuromutilin C15

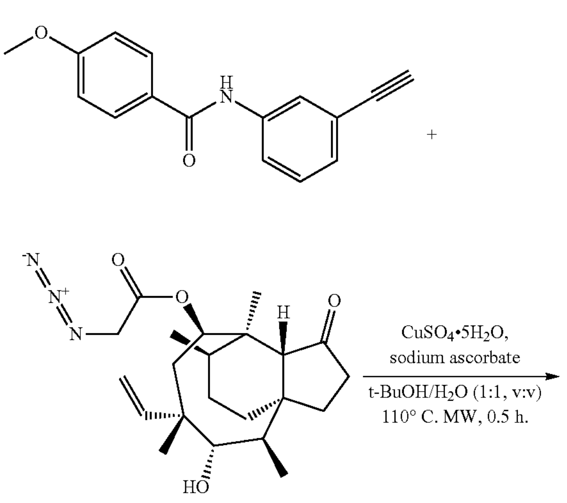

-continued

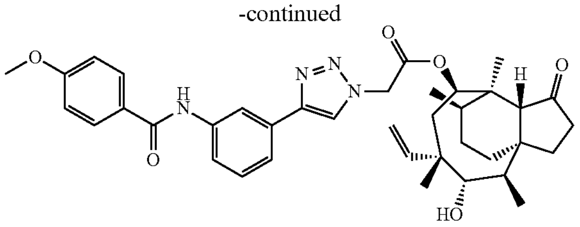

General Procedure 2 was applied with compound A3 (101 mg, 0.250 mmol), the alkyne B30 (68 mg, 0.306 mmol), sodium ascorbate (19 mg, 0.097 mmol) and $CuSO_4 \cdot 5H_2O$ (24.3 mg, 0.097 mmol) in degassed t-BuOH:$H_2O$ (1:1 v/v, 12 mL). Flash Chromatography (MeOH:DCM, 4%). Yield: 157 mg (99%, 0.247 mmol); $^1$H NMR (400 MHz, $CDCl_3$): δ 8.09 (t, J=1.9 Hz, 1H), 8.01 (s, 1H), 7.91 (s, 1H), 7.89-7.83 (m, 2H), 7.71 (ddd, J=8.1, 2.2, 1.0 Hz, 1H), 7.61 (dt, J=7.8, 1.2 Hz, 1H), 7.41 (t, J=8.0 Hz, 1H), 7.00-6.94 (m, 2H), 6.42 (dd, J=17.4, 11.0 Hz, 1H), 5.83 (d, J=8.5 Hz, 1H), 5.37-5.18 (m, 2H), 5.19-5.03 (m, 2H), 2.33-2.02 (m, 5H), 1.81-1.05 (m, 15H), 0.87 (d, J=7.0 Hz, 3H), 0.73 (d, J=7.0 Hz, 3H); $^{13}$C NMR (101 MHz, $CDCl_3$): δ 216.6), 165.3, 165.1, 162.6, 147.9, 138.8, 138.6, 131.1, 129.7, 129.0, 127.0, 121.6, 121.3, 112.0, 117.6, 117.3, 114.0, 74.5, 71.1, 58.0, 55.5, 51.7, 45.4, 44.7, 44.0, 41.9, 36.6, 36.1, 34.4, 30.4, 26.8, 26.4, 24.8, 16.9, 14.6, 11.5; HRMS (ESI): m/z calculated for $C_{38}H_{47}N_4O_6$ ($M^+H^+$) 655.3490 found 625.3353.

22-[4-(3-((9H-purin-6-yl)oxy)phenyl)-1,2,3-triazole-1-yl]-22-deoxypleuromutilin C16

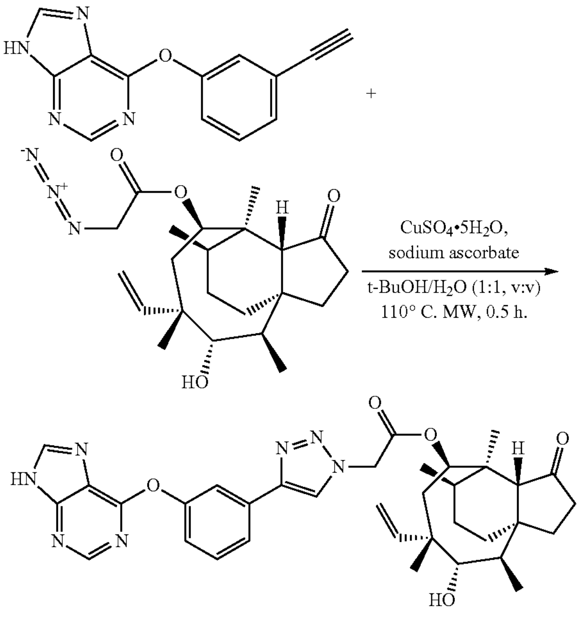

General Procedure 2 was applied with compound A3 (89 mg, 0.221 mmol), the alkyne B31 (58 mg, 0.245 mmol), sodium ascorbate (17.5 mg, 0.088 mmol) and $CuSO_4 \cdot 5H_2O$ (22.0 mg, 0.088 mmol) in degassed t-BuOH:$H_2O$ (1:1 v/v, 12 mL). Flash Chromatography (MeOH:DCM, 4-8%). Yield: 63 mg (44%, 0.097 mmol); $^1$H NMR (400 MHz, $CDCl_3$): δ 13.15 (s, 1H), 8.39 (s, 1H), 8.26 (s, 1H), 7.94 (s, 1H), 7.86 (s, 1H), 7.70 (d, J=7.7 Hz, 1H), 7.50 (t, J=7.9 Hz, 1H), 7.30-7.19 (m, 1H), 6.41 (dd, J=17.4, 11.1 Hz, 1H), 5.82 (d, J=8.4 Hz, 1H), 5.35-5.17 (m, 2H), 5.18-5.04 (m, 2H), 3.37 (s, 1H), 2.33-2.05 (m, 5H), 1.80-1.06 (m, 15H), 0.88 (d, J=6.9 Hz, 3H), 0.72 (d, J=7.0 Hz, 3H). $^{13}$C NMR (101 MHz, $CDCl_3$): δ 216.7 165.0, 151.9, 147.5, 138.6, 131.8, 130.3, 123.3, 121.7, 121.6, 119.4, 117.6, 74.5, 71.2, 58.0, 51.7, 45.4, 44.7, 44.0, 41.9, 36.6, 36.1, 34.4, 30.3, 26.8, 26.4, 24.8, 16.8, 14.7, 11.5; HRMS (ESI): m/z calculated for $C_{35}H_{42}N_7O_5$ ($M^+H^+$) 640.3242 found 640.3223

22-[4-(3-((2-amino-9H-purin-6-yl)oxy)phenyl)-1,2,3-triazole-1-yl]-22-deoxypleuromutilin C17

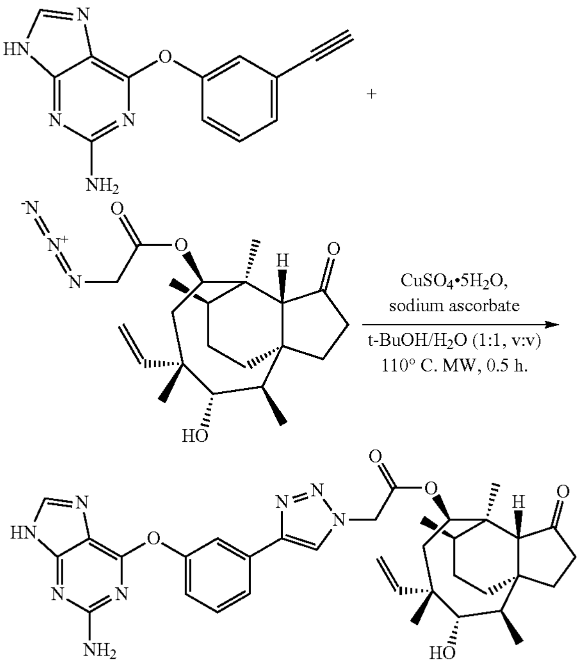

General Procedure 2 was applied with compound A3 (60.3 mg, 0.149 mmol), the alkyne B32 (42.4 mg, 0.169 mmol), sodium ascorbate (12 mg, 0.060 mmol) and $CuSO_4 \cdot 5H_2O$ (15 mg, 0.060 mmol) in degassed t-BuOH:$H_2O$ (1:1 v/v, 14 mL). Flash Chromatography (MeOH:DCM, 4-8%). Yield: 24 mg (25%, 0.037 mmol); $^1$H NMR (400 MHz, $CDCl_3$): δ 12.75 (s, 1H), 8.02-7.75 (m, 3H), 7.54 (d, J=7.7 Hz, 1H), 7.36 (q, J=10.8, 9.4 Hz, 1H), 7.09 (d, J=8.0 Hz, 1H), 6.38 (dd, J=17.3, 11.0 Hz, 1H), 5.78 (d, J=8.2 Hz, 1H), 5.43-5.01 (m, 6H), 3.35 (s, 1H), 2.34-1.00 (m, 20H), 0.86 (d, J=6.7 Hz, 3H), 0.71 (d, J=6.9 Hz, 3H). $^{13}$C NMR (101 MHz, $CDCl^3$): δ 216.6, 165.1, 138.6, 129.9, 122.6, 121.9, 121.4, 119.4, 117.6, 74.5, 71.2, 58.0, 51.7, 45.4, 44.7, 44.0, 41.9, 36.5, 36.0, 34.4, 30.3, 26.8, 26.5, 24.8, 16.9, 14.6, 11.5; HRMS (ESI): m/z calculated for $C_{35}H_{43}N_8O_5$ ($M^+H^+$) 655.3351 found 655.3341

22-[4-(3-((9H-purin-6-yl)amino)phenyl)-1,2,3-triazole-1-yl]-22-deoxypleuromutilin C18

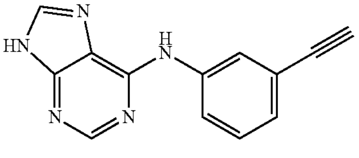

+

-continued

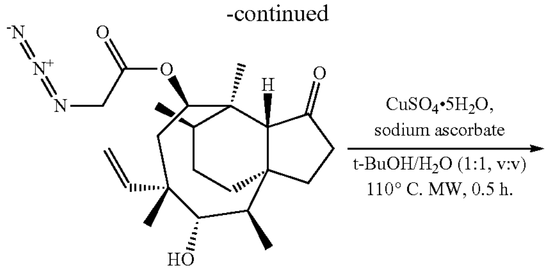

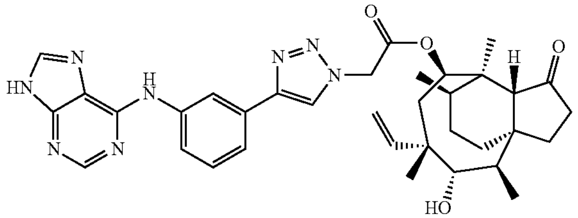

General Procedure 2 was applied with compound A3 (111 mg, 0.275 mmol), the alkyne B33 (73 mg, 0.310 mmol), sodium ascorbate (21.8 mg, 0.110 mmol) and $CuSO_4 \cdot 5H_2O$ (27.5 mg, 0.110 mmol) in degassed t-BuOH:$H_2O$ (1:1 v/v, 12 mL). Flash Chromatography (MeOH:DCM, 3-6%). Yield: 89 mg (51%, 0.140 mmol); $^1H$ NMR (400 MHz, DMSO): δ 13.20 (s, 1H), 9.89 (s, 1H), 8.55-8.38 (m, 3H), 8.30 (s, 1H), 7.98-7.90 (m, 1H), 7.51 (dt, J=7.7, 1.4 Hz, 1H), 7.41 (t, J=7.9 Hz, 1H), 6.15 (dd, J=17.8, 11.2 Hz, 1H), 5.60 (d, J=8.2 Hz, 1H), 5.40 (q, J=17.6 Hz, 2H), 5.23-4.99 (m, 2H), 4.56 (d, J=6.0 Hz, 1H), 3.43 (d, J=12.3 Hz, 1H), 2.24-1.99 (m, 5H), 1.71-0.94 (m, 14H), 0.82 (d, J=6.9 Hz, 3H), 0.67 (d, J=6.9 Hz, 3H). $^{13}C$ NMR (101 MHz, DMSO): δ 216.9, 165.5, 151.71, 146.5, 140.7, 140.3, 128.9, 122.6, 119.4, 117.4, 115.3, 72.5, 70.6, 57.0, 51.2, 44.8, 44.1, 43.3, 41.4, 36.4, 36.2, 33.9, 30.0, 28.5, 26.5, 24.3, 16.1, 14.1, 11.4. HRMS (ESI): m/z calculated for $C_{35}H_{43}N_8O_5$ $(M^+H^+)$ 655.3351 found 639.3376

22-[4-(5-cyano-2-hydroxyphenyl)-1H-1,2,3-triazol-1-yl]-22-deoxypleuromutilin C19

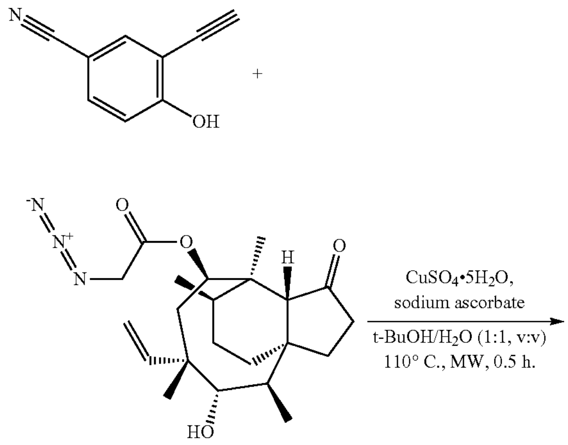

-continued

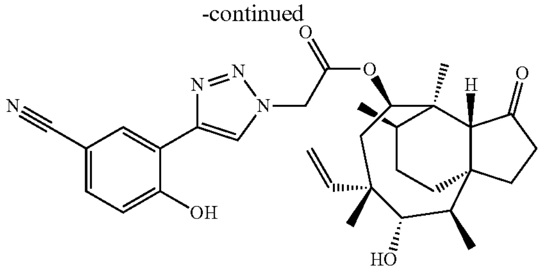

General Procedure 2 was applied with compound A3 (50 mg, 0.124 mmol), the alkyne B36 (20 mg, 0.136 mmol), sodium ascorbate (4.9 mg, 0.025 mmol) and $CuSO_4 \cdot 5H_2O$ (3.0 mg, 0.012 mmol) in degassed t-BuOH:$H_2O$ (1:1 v/v, 2.00 mL). Flash Chromatography (0-50% EtOAc:PE). Yield: 40 mg (59%, 0.073 mmol); $^1H$ NMR (400 MHz, $CDCl_3$) δ 11.41 (s, 1H), 8.04 (s, 1H), 7.77 (d, J=2.0 Hz, 1H), 7.53 (dd, J=8.6, 2.0 Hz, 1H), 7.13 (d, J=8.6 Hz, 1H), 6.41 (dd, J=17.4, 11.0 Hz, 1H), 5.86 (d, J=8.5 Hz, 1H), 5.36 (dd, J=11.0, 1.4 Hz, 1H), 5.28-5.09 (m, 3H), 4.12 (q, J=7.1 Hz, 1H), 3.37 (dd, J=10.5, 6.5 Hz, 1H), 2.34-2.08 (m, 7H), 2.05 (s, 1H), 1.82-1.60 (m, 4H), 1.57 (s, 2H), 1.55-1.41 (m, 4H), 1.40 (s, 3H), 1.36 (d, J=16.1 Hz, 1H), 1.20 (s, 3H), 1.18-1.10 (m, 1H), 0.89 (d, J=7.0 Hz, 3H), 0.75 (d, J=7.1 Hz, 3H) (App. 12.A); $^{13}C$ NMR (101 MHz, $CDCl_3$) δ 216.4, 164.5, 159.6, 146.3, 138.5, 133.5, 130.4, 120.9, 119.1, 119.0, 117.8, 114.9, 103.1, 74.5, 71.7, 60.4, 58.0, 52.0, 45.4, 44.8, 44.1, 41.9, 36.5, 36.1, 34.4, 30.3, 26.8, 26.4, 24.8, 16.9, 14.7, 14.2, 11.5; HRMS (ESI): m/z calculated for $C_{31}H_{43}N_4O_4$ (M+H+) 535.3270 found 535.3289; HPLC purity at 254 nm: 99.6%

22-[4-(4-((Thymine-1-yl)methyl)phenyl)-1,2,3-triazol-1-yl]-22-deoxypleuromutilin C20

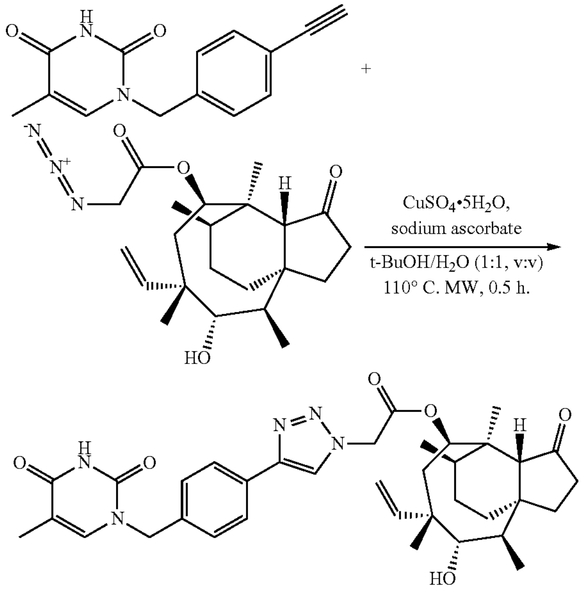

General Procedure 2 was applied with compound 9 (50 mg, 0.124 mmol), the alkyne B37 (31 mg, 0.124 mmol), sodium ascorbate (2.2 mg, 0.013 mmol) and $CuSO_4 \cdot 5H_2O$ (3.3 mg, 0.013 mmol) in degassed t-BuOH:$H_2O$ (1:1 v/v, 2.5 mL). Flash Chromatography ($MeOH:CH_2Cl_2$, 0%→1%→2%→5%). Yield: 82 mg (97%, 0.127 mmol); $^1$H NMR (400 MHz, $CDCl_3$) δ 8.80 (s, 1H), 7.88 (s, 1H), 7.85 (d, J=8.3 Hz, 2H), 7.37 (d, J=8.3 Hz, 2H), 7.01 (d, J=1.3 Hz, 1H), 6.42 (dd, J=17.4, 11.0 Hz, 1H), 5.83 (d, J=8.5 Hz, 1H), 5.34 (dd, J=10.9, 1.5 Hz, 1H), 5.25-5.05 (m, 3H), 4.92 (s, 2H), 3.36 (dd, J=10.5, 6.5 Hz, 1H), 2.33-2.05 (m, 5H), 1.90 (d, J=1.2 Hz, 3H), 1.81-1.59 (m, 4H), 1.54-1.38 (m, 4H), 1.35 (s, 3H), 1.18 (s, 3H), 1.16-1.08 (m, 1H), 0.88 (d, J=7.0 Hz, 3H), 0.72 (d, J=7.1 Hz, 3H); $^{13}$C-NMR (101 MHz, $CDCl_3$) δ 11.4, 12.4, 14.6, 16.8, 24.8, 26.4, 26.8, 30.3, 34.4, 36.1, 36.6, 41.9, 44.0, 44.8, 45.4, 50.8, 51.7, 57.9, 71.1, 74.5, 111.4, 117.5, 121.1, 126.5, 128.5, 130.6, 138.5, 139.6, 147.6, 151.0, 163.8, 165.0, 216.5; HRMS (ESI) m/z calculated for $C_{36}H_{46}N_5O_6$ $(M+H^+)$ 644.3448 found 644.3321; HPLC purity at 254 nm: 97.5%.

22-[4-(6-((6-amino-9H-purin-9-yl)methyl)pyridin-3-yl)-5-(hydroxymethyl)-1H-1,2,3-triazol-1-yl]-22-deoxypleuromutilin trifluoroacetate C21

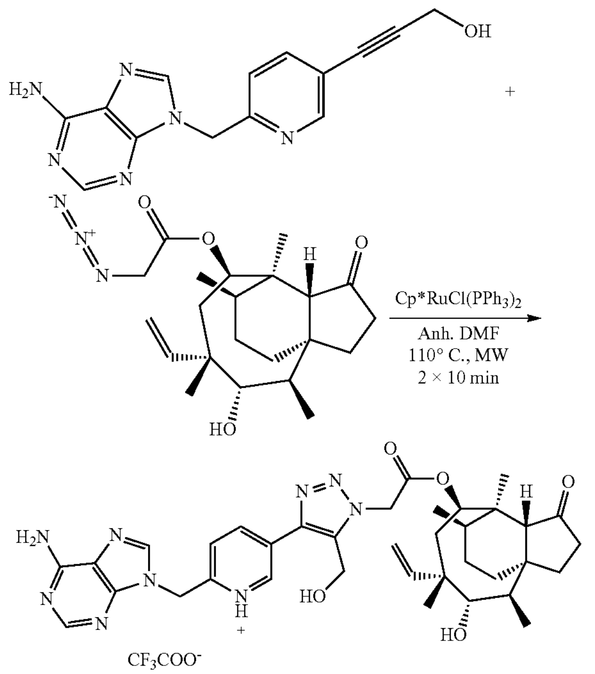

In a small, dry microwave vial, the alkyne B40 (22 mg, 0.079 mmol) and $Cp^*RuCl(PPh_3)_2$ (9.4 mg, 0.012 mmol) was dissolved in anhydrous, degassed (1 h.) DMF (1.96 ml) and stirred for 10 min. under argon, before the azide A3 (38 mg, 0.094 mmol) was added. The vial was sealed and irradiated in a microwave reactor at 110° C. (high absorption mode) for 10 min, before a second portion of $Cp^*RuCl(PPh_3)_2$ (9.4 mg, 0.012 mmol) and the azide A3 (38 mg, 0.094 mmol) was added and then reacted at the same conditions once again. The reaction mixture was concentrated in vacuo and the resulting residue was purified by Flash Chromatography (MeOH:DCM, 7-15%) to afford the crude product followed by Preparative reverse-phase liquid chromatography (RPLC): Gemini NX C18 column (10 μm, 21.2 mm×150 mm); flow, 10 mL/min; 10% acetonitrile (MeCN) in water (0-3 min), 10-100% MeCN in water (3-20 min), 100% MeCN (20-25 min), 100-10% MeCN in water (25-28 min) and 10% acetonitrile (MeCN) in water (28-30 min). Both solvents with 0.1% trifluoro acetic acid as modifier, UV detection at 254 nm. Yield: 15 mg (24%, 0.019 mmol); $^1$H NMR (400 MHz, DMSO) δ 8.83 (bs, 2H), 8.61 (s, 1H), 8.46 (bs, 1H), 8.19 (s, 1H), 7.57 (bs, 2H), 6.10 (dd, J=17.8, 11.3 Hz, 1H), 5.67 (d, J=15.8 Hz, 2H), 5.57 (d, J=8.2 Hz, 1H), 5.51-5.31 (m, 2H), 5.20-4.99 (m, 2H), 4.63 (s, 2H), 3.42 (d, J=5.8 Hz, 1H), 2.41 (s, 1H), 2.25-1.96 (m, 4H), 1.63 (t, J=12.4 Hz, 2H), 1.55-1.18 (m, 8H), 1.07 (s, 3H), 1.00 (td, J=13.6, 13.0, 3.7 Hz, 1H), 0.81 (d, J=6.9 Hz, 3H), 0.64 (d, J=7.0 Hz, 3H); HRMS (ESI): m/z calculated for $C_{36}H_{46}N_9O_5$ $(M^+H^+)$ 684.3616 found 684.3623; HPLC purity at 254 nm: >99.9%.

Example 2—General Procedure for MIC In Vitro Assays

Figure 3:
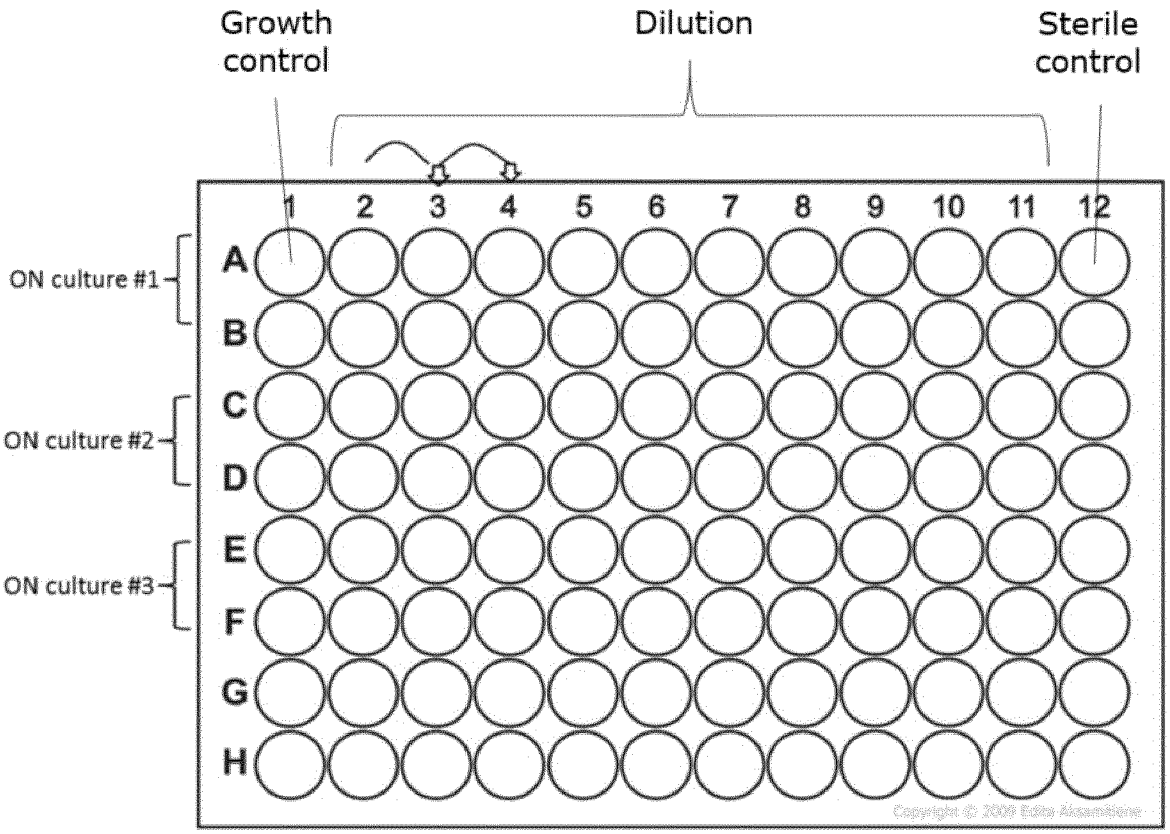
FIG. 3 shows, a 96-well microtiter plate and dilution setup used in the MIC in vitro assays. Column 1 being a growth control, Columns 2 to 11 dilutions of 1×, 2×, 4×, 8×, 16×, 32×, 64×, 128×, 256×, 512× respectively, and column 12 a sterile control. Inoculation involved use of three independent overnight cultures (ON1-ON3) thus giving rise to technical triplicates. Furthermore, each ON was added to two individual dilution rows, giving rise to biological duplicates.

Bacterial susceptibility was established through an in vitro cell-based broth micro-dilution assay. To produce accurate and reproducible MIC-values, a procedure was used which follows the guidelines set by the Clinical and Laboratory Standards Institute (CLSI, USA) and the European Committee on Antimicrobial Susceptibility Testing (EUCAST). The micro-dilutions were carried out in 96-well plates, according to FIG. 3, wherein column 1 is a growth control, Columns 2 to 11 are dilutions of 1×, 2×, 4×, 8×, 16×, 32×, 64×, 128×, 256×, 512× respectively, and column 12 is a sterile control. To further increase the reliability of each susceptibility test, inoculation involved the use of three independent overnight cultures (ON1-ON3) thus giving rise to technical triplicates. Furthermore, each ON was added to two individual dilution rows, giving rise to biological duplicates. The standard inoculum was set to ~$5\cdot10^5$ colony-forming units (CFU) $mL^{-1}$. This was verified by dilution onto agar plates after each overall run.

The applied procedure was:

1.1 MH or BHI agar plates for dilutions were created, 1 plate per overnight (ON) culture and MH or BHI media. 1.2 Day 1: Preparation of ON cultures of the bacterial strain in question, by inoculation of a single colony in 5 mL of MH or BHI media. Then incubation at 37° C. with aeration for approximately 16-20 hours. Biological triplicates were created by inoculation from 3 different colonies per strain.

1.3 Day 2: A 96-well plate with the antibiotic/compound in question was prepared as according to FIG. 3: 1.4 In a 15 mL falcon tube, an appropriate volume of a 1000 μg/mL antibiotic/compound DMSO stock was diluted with MH or BHI media such that a 2× concentration and total volume of 10 mL was achieved. 1.5 A multi-channel pipette was used in the following. 1.6 Column 1 was used for growth control, so no antibiotic/compound was added to that column. 1.7 200 μl of 2× concentration of the antibiotic/compound was added to column 2. Technical duplicates were always created, thus 2 columns per ON culture. 1.8 100 μl of MH or BHI media was added to columns 1, 3-11 and 200 μl of MH or BHI media to column 12. 1.9 100 μl was transferred from column 2 to column 3. The same pipetting tips were used to transfer 100 μL from column 3 to 4. This scheme was repeated until column 11 where 100 μl was discarded after re-suspending. Column 12 was used as a sterile control, so no antibiotic/compound was added to that column. Each transferring involved pipetting up and down 5 to 7 times. 1.10 The plates were fully dried for CFU in the 42° C. incubator, 4× dilutions in triplicates per one plate.

1.11 The optical density of bacterial cells in the ON culture was measured at wavelength 600 nm (OD600).

Then the ON culture was diluted to an OD600=0.1. 1.12 Then the OD600 was re-measured to make certain that it was between 0.08 and 0.13. 1.13 The prepared 0.1 culture of 1.12 was diluted 100× more by transferring of 100 µl thereof, to 10 ml of MH or BHI media (enough for a 96-well plate). 1.14 Then 200 µl of the 100× dilution in 1.13 was transferred to Eppendorf tubes and kept cold until use. 1.15 100 µl of culture with an OD600 on approximately 0.001 was dispensed to each well of columns 1 to 11. 1.16 The plate was closed. Covered with aluminium foil and small holes were created with a 100-200 µL tip.

1.17 The 96-well plate was then incubated at 37° C. with agitation and left for 16-hours.

1.18 Verification of standard inoculum: The 100× diluted culture of 1.13 was used to create $10^{-1}$ to $10^{-4}$ dilutions in PBS/0.9% saline (100 µl sample to 900 µl PBS, mix well and continue until $10^{-4}$). 1.19 10 µl of the $10^{-2}$, $10^{-3}$ and $10^{-4}$ dilutions in 1.18 were spotted onto very dry MH or BHI plates in triplicates. 1.20 Then incubated overnight at 37° C. 1.21 The plates were examined manually or by using the plate reader.

Example 3—Antibacterial Activity of the Compounds Towards MRSA

Multi-resistant *Staphylococcus aureus* (MRSA) USA300 cells (multilocus sequence type 8, clonal complex 8, staphylococcal cassette chromosome mec type IV) were obtained from the American Type Culture Collection, ATCC.

*S. pneumonia* cells, *E. faecalis* cells and vancomycin-resistant *enterococci* (VRE) cells were all obtained from clinical isolates at Rigshospitalet, Copenhagen, Denmark. Both VRE 1 and VRE 5 are ampicillin, ciprofloxacin and vancomycin resistant with the latter, VRE 5, also being linezolid resistant.

The antibacterial activity (the MIC values) of the compounds towards MRSA USA300, *S. pneumonia, E. faecalis*, VRE 1 and VRE 5 are presented in Table 1. Values obtained for the antibiotic drugs Valnemulin, Retapamulin and Lefamulin.Ac, which were bought from a commercial vendor, are provided in the table for comparison, and also values for the prior art compounds 7 and 8 in Ida Dreier et. al., *Bioorg. Med. Chem. Lett.,* 2014, 24, pp. 1044-1045. The values were determined as the lowest concentration of compound to fully inhibit visible growth (OD600) of the bacteria in the in vitro assay.

In conclusion, the antibacterial activity mediated by the compounds of the present invention are considered close to, or even better, than Valnemulin, Retapamulin, Lefamulin.Ac and the prior art compounds 7 and 8. The MRSA USA300 cells were found to be especially susceptible to compound C1 with a MIC value of only 0.03 µg/ml.

TABLE 1 in vitro susceptibility (MIC)

| | MIC [µg mL$^{-1}$] | | | | |
|---|---|---|---|---|---|
| Compound | MRSA USA3000 | S. Pneumonia | E. Faecalis | VRE 1 | VRE 5 |
| 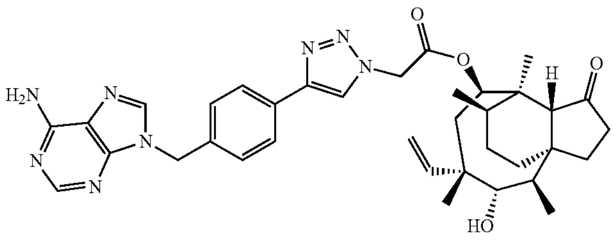 C1 | 0.03 | 0.05 | 0.25 | 0.25 | 0.25 |
| 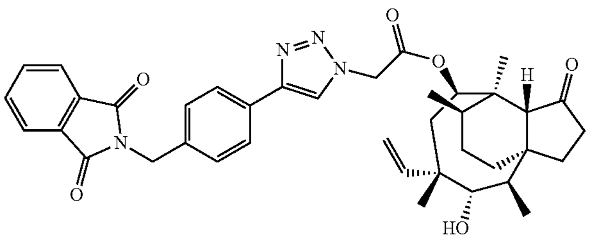 C2 | 0.25 | 4 | 8 | >8 | >8 |
| 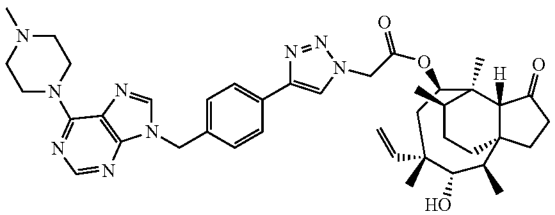 C3 | 0.25 | 0.25 | 0.25 | 0.12-0.25 | 0.12-0.25 |

TABLE 1-continued
in vitro susceptibility (MIC)
| Compound | MIC [μg mL⁻¹] MRSA USA3000 | S. Pneumonia | E. Faecalis | VRE 1 | VRE 5 |
|---|---|---|---|---|---|
| 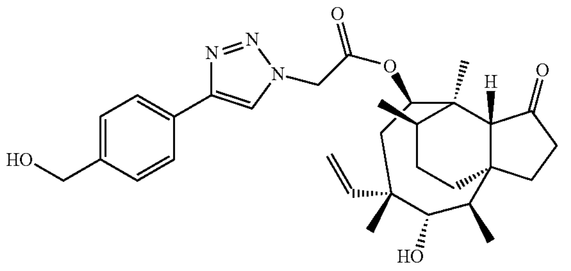 C4 | 0.25 | 4 | 2 | 1.0 | 1 |
| 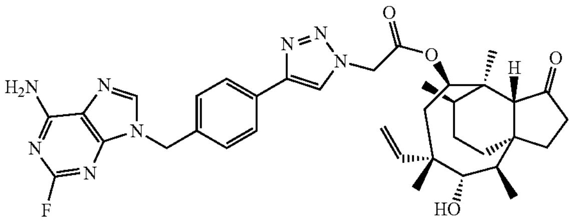 C5 | 0.06 | — | — | — | — |
| 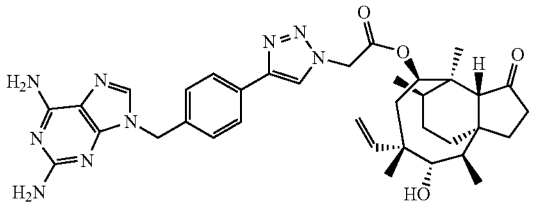 C6 | 0.06 | 0.25 | 0.25 | 0.25 | 0.25 |
| 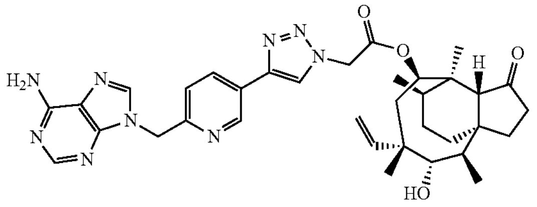 C7 | 0.03 | 0.25 | 0.25 | 0.12 | 0.12 |
| 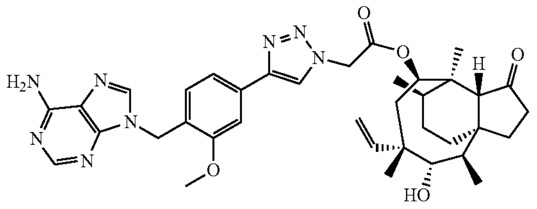 C8 | 0.06 | 0.25 | 0.25 | 0.12 | 0.12 |

TABLE 1-continued
in vitro susceptibility (MIC)
| Compound | MIC [μg mL⁻¹] MRSA USA3000 | S. Pneu-monia | E. Fae-calis | VRE 1 | VRE 5 |
|---|---|---|---|---|---|
| 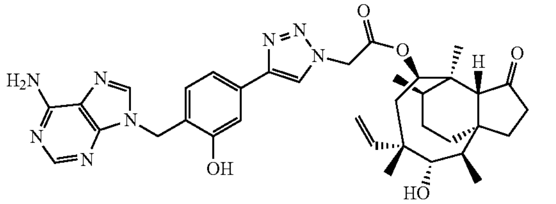 C9 | 0.03 | 0.25 | 0.25 | 0.25 | 0.25 |
| 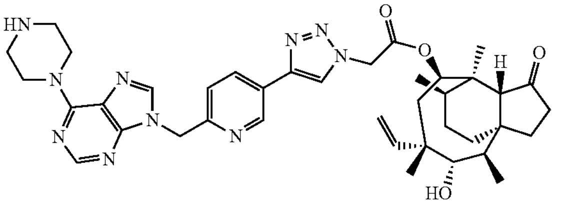 C10 | 0.12-0.25 | 0.03 | 0.03 | 0.03 | 0.12 |
| 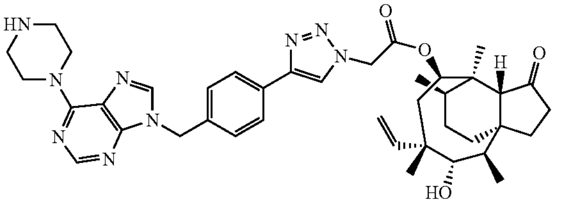 C11 | 0.25 | 0.12 | 0.12 | 0.06 | 0.12 |
| 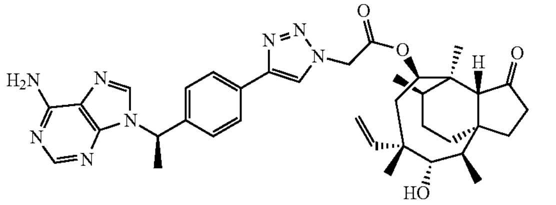 C12 | 0.12 | 0.25 | 0.25 | 0.25 | 0.25 |
| 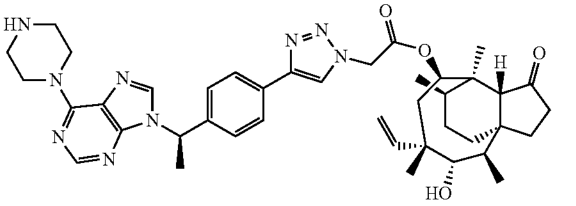 C13 | 0.5 | 0.25 | 0.25 | 0.25 | 0.12-0.25 |
| 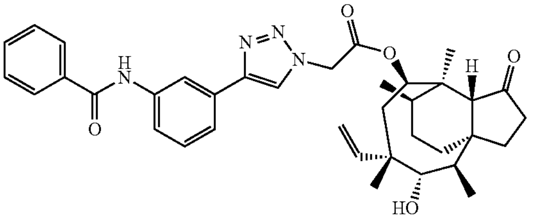 C14 | 0.5 | — | — | — | — |

TABLE 1-continued
| in vitro susceptibility (MIC) | | | | | |
|---|---|---|---|---|---|
| | MIC [μg mL$^{-1}$] | | | | |
| Compound | MRSA USA3000 | S. Pneu-monia | E. Fae-calis | VRE 1 | VRE 5 |
| 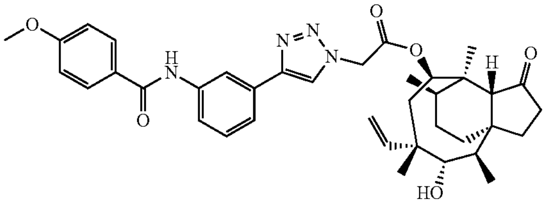 C15 | 0.12 | 0.25 | 0.25 | 0.12 | 0.25 |
| 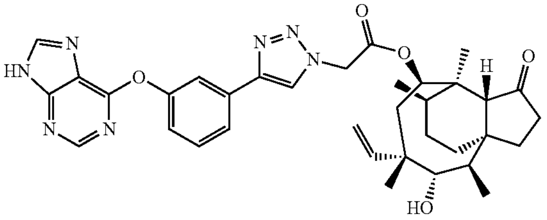 C16 | 0.12 | — | — | — | — |
| 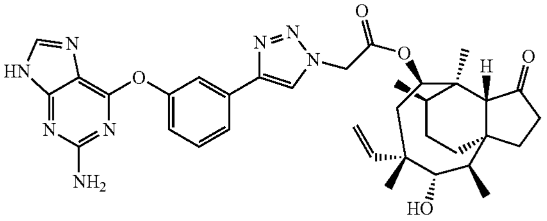 C17 | 0.12 | — | — | — | — |
| 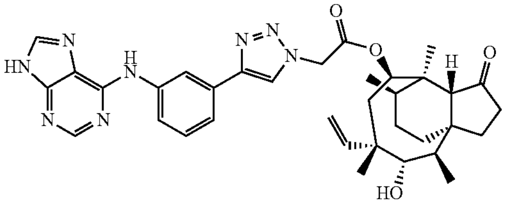 C18 | 0.06 | 0.5 | 0.5 | 0.25 | 0.25 |
| 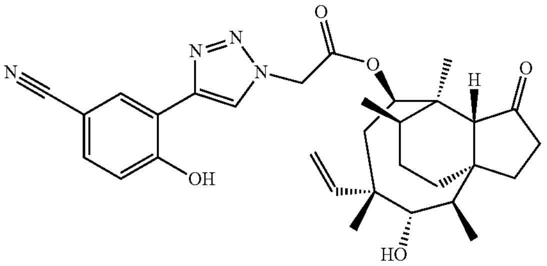 C19 | 0.25 | 4 | 2 | 1 | 1 |

TABLE 1-continued
in vitro susceptibility (MIC)
| Compound | MIC [μg mL⁻¹] MRSA USA3000 | S. Pneumonia | E. Faecalis | VRE 1 | VRE 5 |
|---|---|---|---|---|---|
| 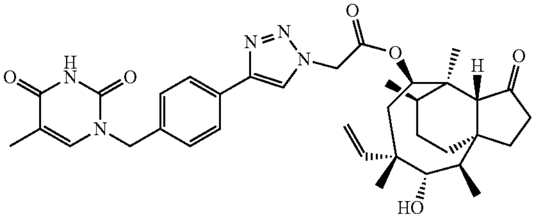 C20 | 0.12 | 1 | 1 | 0.5 | 0.5 |
| 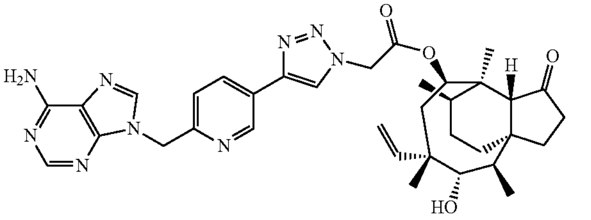 C21 | 0.25 | — | — | — | — |
| 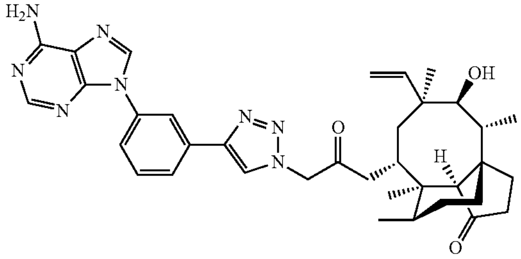 Prior art compound 7 | 0.06 | — | — | — | — |
| 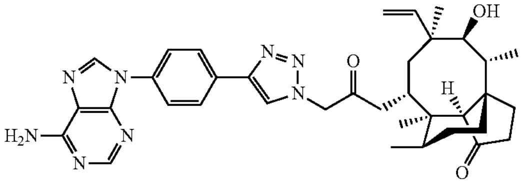 Prior art compound 8 | 0.50 | — | — | — | — |
| 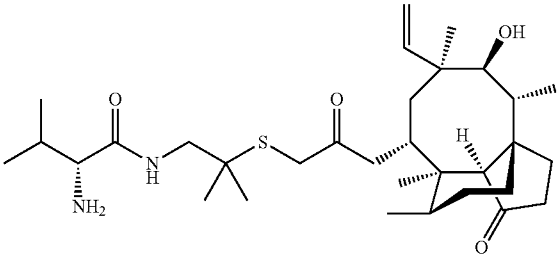 Valnemulin | 0.06 | 0.06-0.12 | 0.03 | 0.03 | 0.015 |

TABLE 1-continued in vitro susceptibility (MIC)

| Compound | MIC [μg mL$^{-1}$] MRSA USA3000 | S. Pneumonia | E. Faecalis | VRE 1 | VRE 5 |
|---|---|---|---|---|---|
| 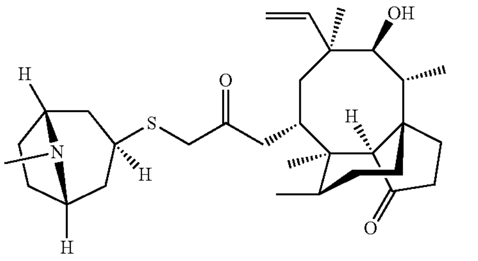 Retapamulin | 0.25 | 0.12 | 0.12 | 0.03 | 0.03 |
| 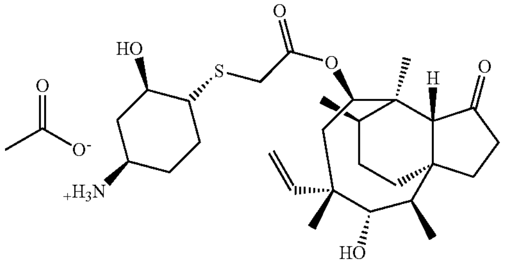 Lefamulin.Ac | — | 0.12 | 0.06 | 0.12 | 0.12 |

REFERENCES

Ida Dreier et. al., *Bioorg. Med. Chem. Lett.,* 2014, 24, 1043-1046.

Ida Dreier et al., *J. Med. Chem.,* 2012, 55, 2067-2077.

Line Lolk et al., *J. Med. Chem.,* 2008, 51, 4957-4967.

WO 00/37074 A1

The invention claimed is:

1. A compound according to Formula (1):

(1)

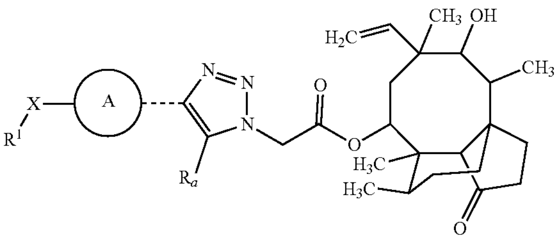

or a pharmaceutically acceptable salt or stereoisomer thereof, wherein:

(i) X is $C_1$-$C_5$alkylene, $C_2$-$C_5$alkenylene, $C_2$-$C_5$alkynylene, —NH—, —O—, or —S—;

wherein the —NH—is optionally substituted with one substituent selected from the group consisting of D and $C_1$-$C_3$alkyl; and wherein the $C_1$-$C_5$alkylene, $C_2$-$C_5$alkenylene, or $C_2$-$C_5$alkynylene is optionally substituted with one or more substituents independently selected from the group consisting of D, F, Cl, Br, and I; and $R^1$ is F, Cl, Br, I, CN, $NO_2$, $C_1$-$C_6$alkyl, $C_2$-$C_6$alkenyl, $C_2$-$C_6$alkynyl, CH(NH), C(O)H, C(O)$NH_2$, C(O)$NHNH_2$, C(O)OH, C(O)O$C_{1\text{-}6}$alkyl, C(O)O$C_{2\text{-}6}$alkenyl, C(O)O$C_{2\text{-}6}$alkynyl, C(O)SH, C(O)phenyl, C(O)aminophenyl, C(O)hydroxyphenyl, C(O)methoxyphenyl, C(O)pyridinyl, C(O)aminopyridinyl, C(O)hydroxypyridinyl, C(O)methoxypyridinyl, C(O)pyridazinyl, C(O)aminopyridazinyl, C(O)hydroxypyridazinyl, C(O)methoxypyridazinyl, C(O)pyrimidinyl, C(O)aminopyrimidinyl, C(O)hydroxypyrimidinyl, C(O)methoxypyrimidinyl, C(O)pyrazinyl, C(O)aminopyrazinyl, C(O)hydroxypyrazinyl, C(O)methoxypyrazinyl, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, SH, S(O)$_2$OH, $C_3$-$C_8$cycloalkyl, heterocyclyl, aryl, or heteroaryl;

wherein the $C_1$-$C_6$alkyl, $C_2$-$C_6$alkenyl, $C_2$-$C_6$alkynyl, or O$C_1$-$C_6$alkyl is optionally substituted with one or more substituents independently selected from the group consisting of D, F, Cl, Br, I, CN, $NO_2$, CH(NH), C(O)H, C(O)$NH_2$, C(O)$NHNH_2$, C(O)OH, C(O)O$C_{1\text{-}6}$alkyl, C(O)O$C_{2\text{-}6}$alkenyl, C(O)O$C_{2\text{-}6}$alkynyl, C(O)SH, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, SH, S(O)$_2$OH, $C_3$-$C_8$cycloalkyl, piperazinyl, aryl, and heteroaryl;

wherein the $C_3$-$C_8$ cycloalkyl or heterocyclyl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, CH(NH), C(O)H, C(O)$NH_2$, C(O)$NHNH_2$, C(O)OH, C(O)O$C_{1-6}$alkyl, C(O)O$C_{2-6}$alkenyl, C(O)O$C_{2-6}$alkynyl, C(O)SH, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, =O, SH, S(O)$_2$OH, $C_3$-$C_8$cycloalkyl, piperazinyl, aryl, and heteroaryl;

wherein the aryl or heteroaryl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, CH(NH), C(O)H, C(O)$NH_2$, C(O)$NHNH_2$, C(O)OH, C(O)O$C_{1-6}$alkyl, C(O)O$C_{2-6}$alkenyl, C(O)O$C_{2-6}$alkynyl, C(O)SH, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, SH, S(O)$_2$OH, $C_3$-$C_8$cycloalkyl, piperazinyl, aryl, and heteroaryl; and wherein each piperazinyl substituent is optionally and independently substituted with one or more independently selected $C_1$-$C_5$alkyl substituents; or (ii) X$R^1$ is CN;

ring A is aryl or heteroaryl, wherein the aryl or heteroaryl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, heterocyclyl, aryl, and heteroaryl;

—is a single bond; and $R_a$ is H, $C_1$-$C_5$alkyl, $C_1$-$C_5$aminoalkyl, $C_1$-$C_5$hydroxyalkyl, $NH_2$, OH, $OCH_3$, or $OCH_2CH_3$.

2. The compound according to claim 1, or a pharmaceutically acceptable salt or stereoisomer thereof, wherein X is $C_1$-$C_5$alkylene, $C_2$-$C_5$alkenylene, $C_2$-$C_5$alkynylene, —NH—, —O—, or —S—;

wherein the —NH— is optionally substituted with one $C_1$-$C_3$alkyl substituent; and wherein the $C_1$-$C_5$alkylene, $C_2$-$C_5$alkenylene, or $C_2$-$C_5$alkynylene is optionally substituted with one or more substituents independently selected from the group consisting of D, F, Cl, Br, and I.

3. The compound according to claim 1, or a pharmaceutically acceptable salt or stereoisomer thereof, wherein:

(a) the $C_1$-$C_6$alkyl, $C_2$-$C_6$alkenyl, $C_2$-$C_6$alkynyl, or O$C_1$-$C_6$alkyl of $R^1$ is optionally substituted with one or more substituents independently selected from the group consisting of D, F, Cl, Br, I, CN, $NO_2$, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, SH, S(O)$_2$OH, $C_3$-$C_6$cycloalkyl, piperazinyl, aryl, and heteroaryl;

(b) the $C_3$-$C_8$cycloalkyl or heterocyclyl of $R^1$ is optionally substituted with one or more substituents independently selected from the group consisting of D, F, Cl, Br, I, CN, $NO_2$, $C_1$-$C_4$alkyl, $C_2$-$C_4$alkenyl, $C_2$-$C_4$alkynyl, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, =O, SH, S(O)$_2$OH, $C_3$-$C_6$cycloalkyl, piperazinyl, aryl, and heteroaryl;

(c) the aryl or heteroaryl of $R^1$ is optionally substituted with one or more substituents independently selected from the group consisting of D, F, Cl, Br, I, CN, $NO_2$, $C_1$-$C_4$alkyl, $C_2$-$C_4$alkenyl, $C_2$-$C_4$alkynyl, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, SH, S(O)$_2$OH, $C_3$-$C_6$cycloalkyl, piperazinyl, aryl, and heteroaryl; and (d) each piperazinyl substituent is optionally and independently substituted with one or more independently selected $C_1$-$C_5$alkyl substituents.

4. The compound according to claim 1, or a pharmaceutically acceptable salt or stereoisomer thereof, wherein $R^1$ is F, Cl, Br, I, CN, $NO_2$, $C_1$-$C_4$alkyl, $C_2$-$C_4$alkenyl, $C_2$-$C_4$alkynyl, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, C(O)phenyl, C(O)aminophenyl, C(O)hydroxyphenyl, C(O)methoxyphenyl, C(O)pyridinyl, C(O)aminopyridinyl, C(O)hydroxypyridinyl, C(O)methoxypyridinyl, C(O)pyridazinyl, C(O)aminopyridazinyl, C(O)hydroxypyridazinyl, C(O)methoxypyridazinyl, C(O)pyrimidinyl, C(O)aminopyrimidinyl, C(O)hydroxypyrimidinyl, C(O)methoxypyrimidinyl, C(O)pyrazinyl, C(O)aminopyrazinyl, C(O)hydroxypyrazinyl, C(O)methoxypyrazinyl, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, SH, S(O)$_2$OH, $C_3$-$C_6$cycloalkyl, heterocyclyl, aryl, or heteroaryl;

wherein the $C_1$-$C_4$alkyl, $C_2$-$C_4$alkenyl, $C_2$-$C_4$alkynyl, or O$C_1$-$C_4$alkyl is optionally substituted with one or more substituents independently selected from the group consisting of D, F, Cl, Br, I, CN, $NO_2$, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, SH, S(O)$_2$OH, $C_3$-$C_6$cycloalkyl, piperazinyl, aryl, and heteroaryl;

wherein the $C_3$-$C_6$cycloalkyl or heterocyclyl is optionally substituted with one or more substituents independently selected from the group consisting of D, F, Cl, Br, I, CN, $NO_2$, $C_1$-$C_4$alkyl, $C_2$-$C_4$alkenyl, $C_2$-$C_4$alkynyl, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_6$aminoalkyl, NHC(NH)$NH_2$, N($C_1$-$C_4$alkyl)$_2$, OH, O$C_1$-$C_4$alkyl, =O, SH, S(O)$_2$OH, $C_3$-$C_6$cycloalkyl, piperazinyl, aryl, and heteroaryl;

wherein the aryl or heteroaryl is optionally substituted with one or more substituents independently selected from the group consisting of D, F, Cl, Br, I, CN, $NO_2$, $C_1$-$C_4$alkyl, $C_2$-$C_4$alkenyl, $C_2$-$C_4$alkynyl, CH(NH), C(O)H, C(O)$NH_2$, C(O)$NHNH_2$, C(O)OH, C(O)O$C_{1-4}$alkyl, C(O)O$C_{2-4}$alkenyl, C(O)O$C_{2-4}$alkynyl, C(O)SH, $NH_2$, NH$C_1$-$C_4$alkyl, NH$C_1$-$C_4$aminoalkyl, NHC(NH)$NH_2$, N($C_1$-$C_4$alkyl)$_2$, OH, O$C_1$-$C_4$alkyl, SH, S(O)$_2$OH, $C_3$-$C_6$cycloalkyl, piperazinyl, aryl, and heteroaryl; and wherein each piperazinyl substituent is optionally and independently substituted with one or more independently selected $C_1$-$C_5$alkyl substituents.

5. The compound according to claim 1, or a pharmaceutically acceptable salt or stereoisomer thereof, wherein $R^1$ is a monocyclic heterocyclyl, bicyclic heterocyclyl, monocyclic heteroaryl, or bicyclic heteroaryl;

wherein the monocyclic heterocyclyl or bicyclic heterocyclyl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, CH(NH), C(O)H, C(O)$NH_2$, C(O)$NHNH_2$, C(O)OH, C(O)O$C_{1-6}$alkyl, C(O)O$C_{2-6}$alkenyl, C(O)O$C_{2-6}$alkynyl, C(O)SH, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, =O, SH, S(O)$_2$OH, $C_3$-$C_8$cycloalkyl, piperazinyl, aryl, and heteroaryl;

wherein the monocyclic heteroaryl or bicyclic heteroaryl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, CH(NH), C(O)H, C(O)$NH_2$, C(O)$NHNH_2$, C(O)OH, C(O)O$C_{1-6}$alkyl, C(O)O$C_{2-6}$alkenyl, C(O)O$C_{2-6}$alkynyl, C(O)SH, $NH_2$, NH$C_1$-$C_6$alkyl, NH$C_1$-$C_6$aminoalkyl, NHC(NH)$NH_2$, N($C_1$-$C_6$alkyl)$_2$, OH, O$C_1$-$C_6$alkyl, SH, S(O)$_2$OH, $C_3$-$C_8$cycloalkyl, piperazinyl, aryl, and heteroaryl; and wherein each piperazinyl substituent is optionally and independently substituted with one or more independently selected $C_1$-$C_5$alkyl substituents.

6. The compound according to claim 5, or a pharmaceutically acceptable salt or stereoisomer thereof, wherein $R^1$ is pyrrolidinyl, tetrahydrofuranyl, tetrahydrothiophenyl, piperidinyl, tetrahydropyranyl, pyranyl, thianyl, thiopyranyl, pyrazolidinyl, imidazolidinyl, isoxazolidinyl, oxazolidinyl, isothiazolidinyl, thiazolidinyl, dioxolanyl, dithiolanyl, dioxazolyl, dithiazolyl, diazinanyl, morpholinyl, oxazinyl, thiomorpholinyl, thiazinyl, dioxanyl, dioxinyl, triazinanyl, trioxanyl, trithianyl, isoindolyl, indolinyl, phthalimidyl, isochromenyl, chromenyl, tetrahydroquinolinyl, benzooxazinyl, pyrrolyl, furanyl, thiophenyl, pyrazolyl, imidazolyl, isoxazolyl, oxazolyl, isothiazolyl, thiazolyl, triazolyl, oxadiazolyl, thiadiazolyl, pyridinyl, diazinyl, triazinyl, indolyl, isobenzofuranyl, benzofuranyl, benzothiophenyl, indazolyl, benzimidazolyl, benzoisoxazolyl, benzooxazolyl, benzoisothiazolyl, benzothiazolyl, isoquinolinyl, quinolinyl, phthalazinyl, quinazolinyl, quinoxalinyl, azaindolyl, azaindazolyl, purinyl, adeninyl, guaninyl, xanthinyl, hypoxanthinyl, naphthyridinyl, pyridopyrimidinyl, pyridopyrazinyl, or pteridinyl.

7. The compound according to claim 1, or a pharmaceutically acceptable salt or stereoisomer thereof, wherein ring A is a 6-membered aryl or 6-membered heteroaryl, wherein the 6-membered aryl or 6-membered heteroaryl is optionally substituted with one or more substituents independently selected from the group consisting of D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, heterocyclyl, aryl, and heteroaryl.

8. The compound according to claim 7, or a pharmaceutically acceptable salt or stereoisomer thereof, wherein the 6-membered aryl or 6-membered heteroaryl is optionally substituted with one or more substituents independently selected from the group consisting of D, F, Cl, Br, I, CN, $NO_2$, $C_1$-$C_4$alkyl, $C_2$-$C_4$alkenyl, $C_2$-$C_4$alkynyl, C(O)$NH_2$, C(O)OH, $NH_2$, NH$C_1$-$C_4$alkyl, N($C_1$-$C_4$alkyl)$_2$, OH, O$C_1$-$C_4$alkyl, $C_3$-$C_6$cycloalkyl, aryl, and heteroaryl.

9. The compound according to claim 1, or a stereoisomer thereof, wherein the stereoisomer of the compound is represented by Formula (2):

(2)

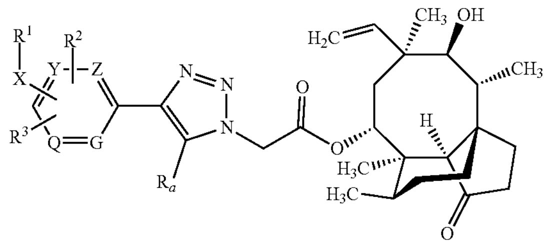

or a pharmaceutically acceptable salt thereof, wherein:

G is CH or N;

Q is CH or N;

Y is CH or N;

Z is CH or N;

$R^2$ is H, D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, aryl, and heteroaryl; and $R^3$ is H, D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, aryl, and heteroaryl;

with the proviso that X is bonded to the meta or para position.

10. The compound according to claim 1, or a stereoisomer thereof, wherein the stereoisomer of the compound is represented by Formula (2a):

(2a)

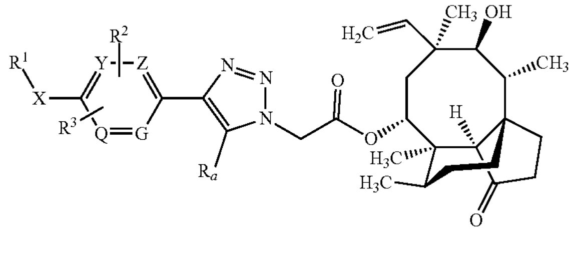

or a pharmaceutically acceptable salt thereof, wherein:

G is CH or N;

Q is CH or N;

Y is CH or N;

Z is CH or N;

$R^2$ is H, D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, aryl, and heteroaryl; and $R^3$ is H, D, F, Cl, Br, I, CN, $NO_2$, $C_1$-$C_6$alkyl, $C_2$-$C_6$alkenyl, $C_2$-$C_6$alkynyl, C(O)$NH_2$, C(O)OH, $NH_2$, NH$C_1$-$C_6$alkyl, N($C_1$-$C_6$alkyl)$_2$, OH, O$C_1$-$C_6$alkyl, $C_3$-$C_8$cycloalkyl, aryl, and heteroaryl.

11. The compound according to claim 1, or a stereoisomer thereof, wherein the stereoisomer of the compound is represented by Formula (2b):

(2b)

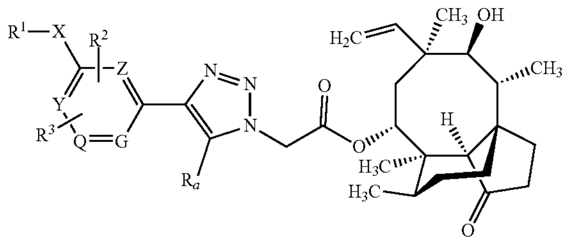

or a pharmaceutically acceptable salt thereof, wherein:

G is CH or N;

Q is CH or N;

Y is CH or N;

Z is CH or N;

$R^2$ is H, D, F, Cl, Br, I, CN, $NO_2$, $C_1$-$C_6$alkyl, $C_2$-$C_6$alkenyl, $C_2$-$C_6$alkynyl, $C(O)NH_2$, C(O)OH, $NH_2$, $NHC_1$-$C_6$alkyl, $N(C_1$-$C_6alkyl)_2$, OH, $OC_1$-$C_6$alkyl, $C_3$-$C_8$cycloalkyl, aryl, and heteroaryl; and $R^3$ is H, D, F, Cl, Br, I, CN, $NO_2$, $C_1$-$C_6$alkyl, $C_2$-$C_6$alkenyl, $C_2$-$C_6$alkynyl, $C(O)NH_2$, C(O)OH, $NH_2$, $NHC_1$-$C_6$alkyl, $N(C_1$-$C_6alkyl)_2$, OH, $OC_1$-$C_6$alkyl, $C_3$-$C_8$cycloalkyl, aryl, and heteroaryl.

12. The compound according to claim 1, or a stereoisomer thereof, wherein the compound, or stereoisomer thereof, is selected from the group consisting of:

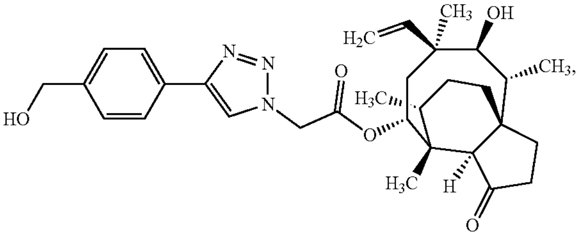

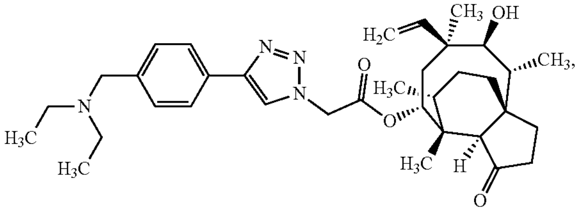

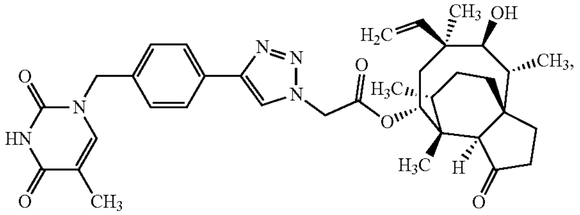

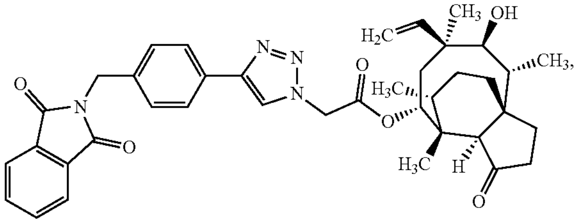

-continued

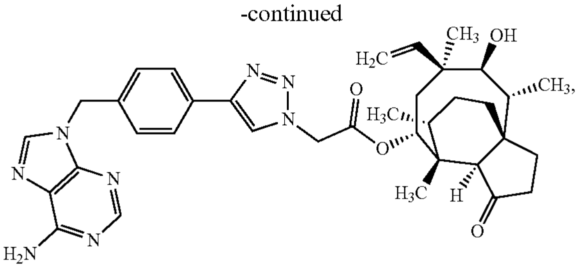

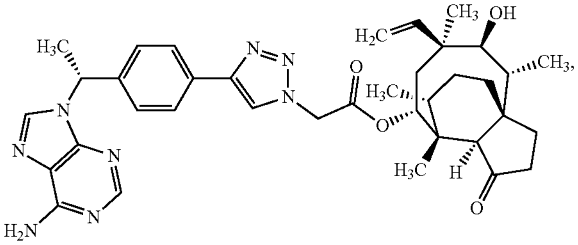

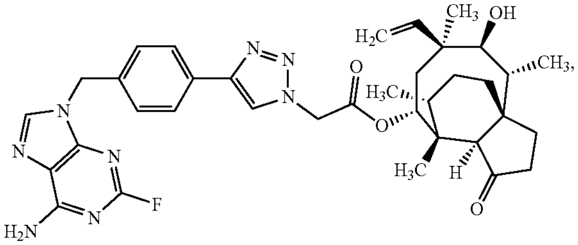

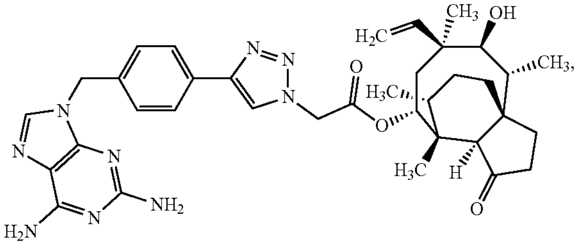

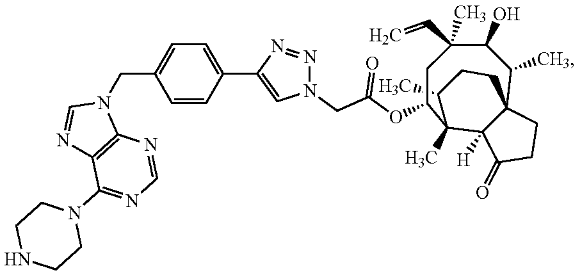

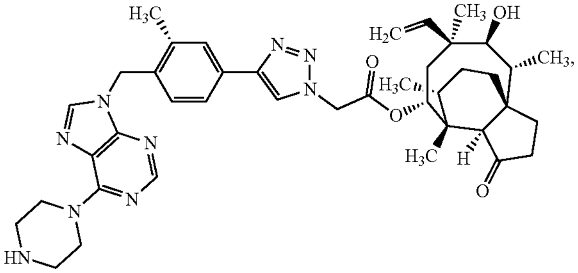

-continued

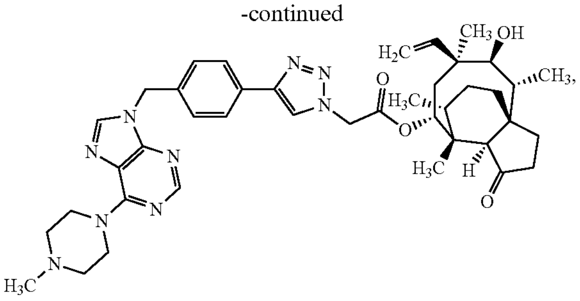

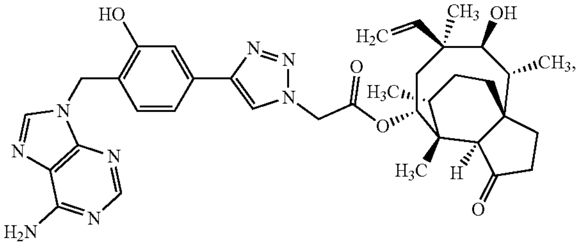

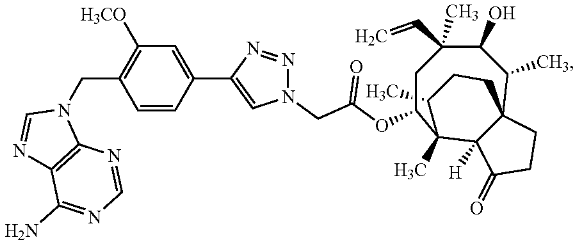

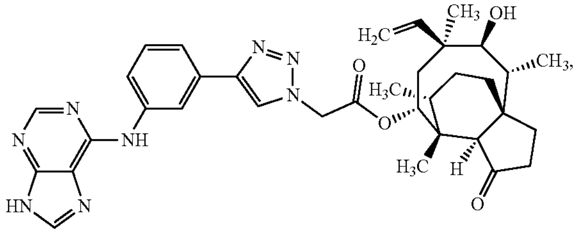

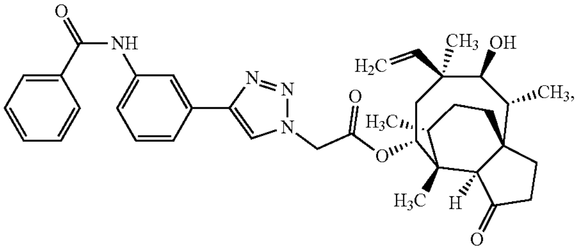

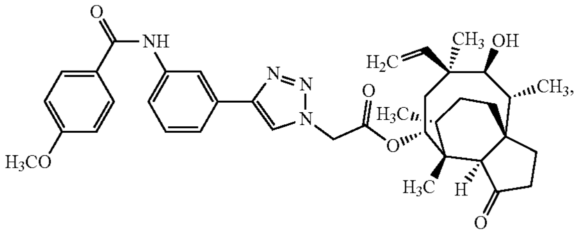

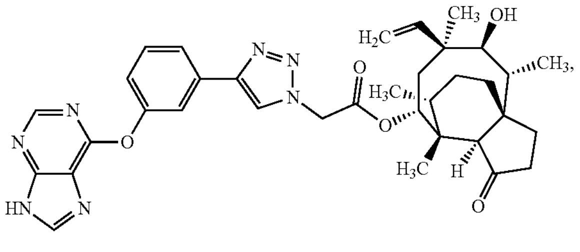

-continued

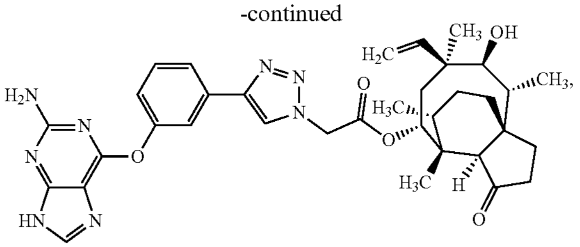

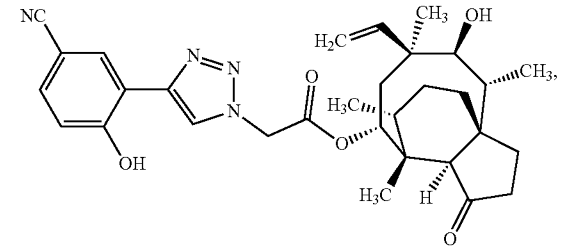

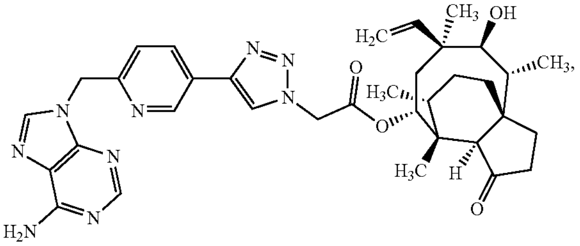

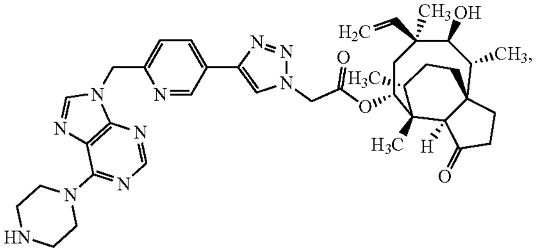

and

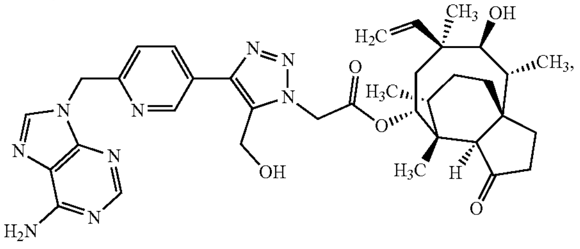

or a pharmaceutically acceptable salt thereof.

13. A pharmaceutical composition comprising at least one carrier, diluent, or excipient and a compound according to claim 1, or a pharmaceutically acceptable salt or stereoisomer thereof.

14. The pharmaceutical composition according to claim 13, wherein the pharmaceutical composition further comprises at least one adjuvant.

15. A kit comprising:

(i) a compound according to claim 1, or a pharmaceutically acceptable salt or stereoisomer thereof, or a pharmaceutical composition according to claim 13;

(ii) at least one additional therapeutic agent; and optionally, (iii) instructions for use.

16. A method for treating a bacterial infection in a subject, wherein the method comprises administering to the subject in need thereof a therapeutically effective amount of a compound according to claim 1, or a pharmaceutically acceptable salt or stereoisomer thereof.

17. The method according to claim 16, wherein the bacterial infection is caused by a bacterium or bacteria selected from the group consisting of *Chlamydia trachomatis, Cutibacterium acnes*, an *enterobacteriaceae*, an *enterococcus, Haemophilus influenza, Listeria monocytogenes, Morganella morganii, Mycoplasma pneumonia*, methicillin-resistant *Staphylococcus aureus* (MRSA), *Staphylococcus epidermidis, Staphylococcus haemolyticus*, an alpha-hemolytic *streptococcus*, and a beta-hemolytic *streptococcus.*

18. The method according to claim 17, wherein the bacterial infection is caused by a bacterium or bacteria selected from the group consisting of *Enterococcus faecalis*, a vancomycin-resistant *enterococcus* (VRE), methicillin-resistant *Staphylococcus aureus* (MRSA), and *Streptococcus pneumoniae.*

19. The method according to claim 17, wherein the *enterobacteriaceae* is *Escherichia coli.*

20. The method according to claim 17, wherein the *enterococcus* is *Enterococcus faecalis* or a vancomycin-resistant *enterococcus* (VRE).

21. The method according to claim 17, wherein the alpha-hemolytic *streptococcus* or beta-hemolytic *streptococcus* is *Streptococcus aureus* or *Streptococcus pneumoniae.*

22. A method for treating a bacterial infection in a subject, wherein the method comprises administering to the subject in need thereof a therapeutically effective amount of the pharmaceutical composition according to claim 13.

23. The method according to claim 22, wherein the bacterial infection is caused by a bacterium or bacteria selected from the group consisting of *Chlamydia trachomatis, Cutibacterium acnes*, an *enterobacteriaceae*, an *enterococcus, Haemophilus influenza, Listeria monocytogenes, Morganella morganii, Mycoplasma pneumonia*, methicillin-resistant *Staphylococcus aureus* (MRSA), *Staphylococcus epidermidis, Staphylococcus haemolyticus*, an alpha-hemolytic *streptococcus*, and a beta-hemolytic *streptococcus.*

24. The method according to claim 23, wherein the bacterial infection is caused by a bacterium or bacteria selected from the group consisting of *Enterococcus faecalis*, a vancomycin-resistant *enterococcus* (VRE), methicillin-resistant *Staphylococcus aureus* (MRSA), and *Streptococcus pneumoniae.*

25. The method according to claim 23, wherein the *enterobacteriaceae* is *Escherichia coli.*

26. The method according to claim 23, wherein the *enterococcus* is *Enterococcus faecalis* or a vancomycin-resistant *enterococcus* (VRE).

27. The method according to claim 23, wherein the alpha-hemolytic *streptococcus* or beta-hemolytic *streptococcus* is *Streptococcus aureus* or *Streptococcus pneumoniae.*

28. A method for treating a fungal infection in a subject, wherein the method comprises administering to the subject in need thereof a therapeutically effective amount of a compound according to claim 1, or a pharmaceutically acceptable salt or stereoisomer thereof.

29. A method for treating a fungal infection in a subject, wherein the method comprises administering to the subject in need thereof a therapeutically effective amount of the pharmaceutical composition according to claim 13.

* * * * *